US009376681B2

(12) United States Patent
Montgomery et al.

(10) Patent No.: US 9,376,681 B2
(45) Date of Patent: Jun. 28, 2016

(54) MIR-29 MIMICS AND USES THEREOF

(71) Applicant: MiRagen Therapeutics, Inc., Boulder, CO (US)

(72) Inventors: Rusty L. Montgomery, Boulder, CO (US); Christina M. Dalby, Boulder, CO (US); Eva Van Rooij, Utrecht (NL); Corrie Gallant-Behm, Boulder, CO (US)

(73) Assignee: miRagen Therapeutics, Inc., Boulder, CO (US)

( * ) Notice: Subject to any disclaimer, the term of this patent is extended or adjusted under 35 U.S.C. 154(b) by 0 days.

(21) Appl. No.: 14/848,085

(22) Filed: Sep. 8, 2015

(65) Prior Publication Data

US 2016/0068842 A1 Mar. 10, 2016

Related U.S. Application Data

(60) Provisional application No. 62/047,562, filed on Sep. 8, 2014.

(51) Int. Cl.

*C12N 15/113* (2010.01)
*A61K 31/713* (2006.01)
*A61K 9/00* (2006.01)

(52) U.S. Cl.

CPC ............ *C12N 15/113* (2013.01); *A61K 9/0073* (2013.01); *A61K 31/713* (2013.01); *C12N 2310/113* (2013.01); *C12N 2310/141* (2013.01); *C12N 2310/315* (2013.01); *C12N 2310/3231* (2013.01); *C12N 2310/343* (2013.01); *C12N 2310/346* (2013.01); *C12N 2320/51* (2013.01)

(58) Field of Classification Search

CPC ........... C12N 15/113; C12N 2310/141; C12N 2310/113; A61K 31/713

See application file for complete search history.

(56) References Cited

U.S. PATENT DOCUMENTS

| | | | |
|---|---|---|---|
| 8,188,060 | B2 | 5/2012 | Khvorova et al. |
| 8,415,466 | B2 | 4/2013 | Khvorova et al. |
| 8,440,636 | B2 | 5/2013 | Olson et al. |
| 8,940,711 | B2 | 1/2015 | Olson et al. |
| 8,940,712 | B2 | 1/2015 | Olson et al. |
| 8,940,713 | B2 | 1/2015 | Olson et al. |
| 9,139,832 | B2 | 9/2015 | Lollo et al. |
| 2005/0059005 | A1 | 3/2005 | Tuschl et al. |
| 2010/0184209 | A1 | 7/2010 | Vermeulen et al. |
| 2010/0285073 | A1 | 11/2010 | Olson et al. |
| 2012/0022143 | A1 | 1/2012 | Jadhav et al. |
| 2013/0195891 | A1 | 8/2013 | Olson et al. |
| 2013/0259908 | A1 | 10/2013 | Olson et al. |
| 2013/0261169 | A1 | 10/2013 | Olson et al. |

OTHER PUBLICATIONS

Montgomery et al. "MicroRNA mimicry blocks pulmonary fibrosis," EMBO Molecular Medicine, Sep. 19, 2014, vol. 6, pp. 1347-1356.

Van Rooij et al. "Dysregulation of microRNAs after myocardial infarction reveals a role of miR-29 in cardiac fibrosis," Proceedings of the National Academy of Sciences, Sep. 2, 2008, vol. 105, pp. 13027-13032.

Van Rooij et al. "Development of microRNA therapeutics is coming of age," EMBO Molecular Medicine, Jun. 16, 2014, vol. 6, pp. 851-864.

Declaration of Dr. Eva van Rooij, filed with USPTO on Oct. 9, 2012, in prosecution of U.S. Appl. No. 12/671,445, now U.S. Pat. No. 8,440,636.

Ye et al. "Downregulation of microRNA-29 by antisense inhibitors and a PPAR-y agonist protects against myocardial ischaemia-reperfusion injury," Cardiovascular Research, Feb. 17, 2010, vol. 87, pp. 535-544.

International Search Report and Written Opinion issued for PCT/US2015/049018 mailed on Jan. 20, 2016.

*Primary Examiner* — Jon E Angell

(74) *Attorney, Agent, or Firm* — Cooley LLP

(57) ABSTRACT

The present invention relates to synthetic oligonucleotide mimetics of miRNAs. In particular, the present invention provides double-stranded, chemically-modified oligonucleotide mimetics of miR-29. Pharmaceutical compositions comprising the mimetics and their use in treating or preventing conditions associated with dysregulation of extracellular matrix genes, such as tissue fibrotic conditions, are also described.

12 Claims, 17 Drawing Sheets

SEQUENCE LISTING

```
<160> NUMBER OF SEQ ID NOS: 42

<210> SEQ ID NO 1
<211> LENGTH: 23
<212> TYPE: RNA
<213> ORGANISM: Artificial Sequence
<220> FEATURE:
<223> OTHER INFORMATION: miR-29b mimic second-sense-passenger strand
<220> FEATURE:
<221> NAME/KEY: MOD_RES
<222> LOCATION: (1)..(1)
<223> OTHER INFORMATION: May be O-methyl adenosine
<220> FEATURE:
<221> NAME/KEY: MOD_RES
<222> LOCATION: (2)..(2)
<223> OTHER INFORMATION: May be O-methyl adenosine
<220> FEATURE:
<221> NAME/KEY: MOD_RES
<222> LOCATION: (3)..(3)
<223> OTHER INFORMATION: May be O-methyl cytidine
<220> FEATURE:
<221> NAME/KEY: MOD_RES
<222> LOCATION: (5)..(5)
<223> OTHER INFORMATION: May be O-methyl cytidine
<220> FEATURE:
<221> NAME/KEY: MOD_RES
<222> LOCATION: (6)..(6)
<223> OTHER INFORMATION: May be O-methyl uridine
<220> FEATURE:
<221> NAME/KEY: MOD_RES
<222> LOCATION: (8)..(8)
<223> OTHER INFORMATION: May be O-methyl uridine
<220> FEATURE:
<221> NAME/KEY: MOD_RES
<222> LOCATION: (9)..(9)
<223> OTHER INFORMATION: May be O-methyl uridine
<220> FEATURE:
<221> NAME/KEY: MOD_RES
<222> LOCATION: (10)..(10)
<223> OTHER INFORMATION: May be O-methyl uridine
<220> FEATURE:
<221> NAME/KEY: MOD_RES
```

-continued

<222> LOCATION: (12)..(12)
<223> OTHER INFORMATION: May be O-methyl cytidine
<220> FEATURE:
<221> NAME/KEY: MOD_RES
<222> LOCATION: (16)..(16)
<223> OTHER INFORMATION: May be O-methyl uridine
<220> FEATURE:
<221> NAME/KEY: MOD_RES
<222> LOCATION: (19)..(19)
<223> OTHER INFORMATION: May be O-methyl uridine
<220> FEATURE:
<221> NAME/KEY: MOD_RES
<222> LOCATION: (20)..(20)
<223> OTHER INFORMATION: May be O-methyl cytidine
<220> FEATURE:
<221> NAME/KEY: MOD_RES
<222> LOCATION: (21)..(21)
<223> OTHER INFORMATION: May be O-methyl cytidine
<220> FEATURE:
<221> NAME/KEY: MOD_RES
<222> LOCATION: (22)..(22)
<223> OTHER INFORMATION: May be O-methyl uridine
<220> FEATURE:
<221> NAME/KEY: MISC_FEATURE
<222> LOCATION: (23)..(23)
<223> OTHER INFORMATION: May be modified with a cholesterol conjugate
with a 6 carbon linker

<400> SEQUENCE: 1
aacacuguuu acaaaugguc cua 23

<210> SEQ ID NO 2
<211> LENGTH: 25
<212> TYPE: RNA
<213> ORGANISM: Artificial Sequence
<220> FEATURE:
<223> OTHER INFORMATION: miR-29b mimic first-antisense-guide strand
<220> FEATURE:
<221> NAME/KEY: MISC_FEATURE
<222> LOCATION: (1)..(1)
<223> OTHER INFORMATION: May be modified with a monophosphate moiety
<220> FEATURE:
<221> NAME/KEY: MOD_RES
<222> LOCATION: (1)..(1)
<223> OTHER INFORMATION: May be fluoro uridine
<220> FEATURE:
<221> NAME/KEY: MOD_RES
<222> LOCATION: (4)..(4)
<223> OTHER INFORMATION: May be fluoro cytidine
<220> FEATURE:
<221> NAME/KEY: MOD_RES
<222> LOCATION: (6)..(6)
<223> OTHER INFORMATION: May be fluoro cytidine
<220> FEATURE:
<221> NAME/KEY: MOD_RES
<222> LOCATION: (7)..(7)
<223> OTHER INFORMATION: May be fluoro cytidine
<220> FEATURE:
<221> NAME/KEY: MOD_RES
<222> LOCATION: (9)..(9)
<223> OTHER INFORMATION: May be fluoro uridine
<220> FEATURE:
<221> NAME/KEY: MOD_RES
<222> LOCATION: (10)..(10)
<223> OTHER INFORMATION: May be fluoro uridine
<220> FEATURE:
<221> NAME/KEY: MOD_RES
<222> LOCATION: (11)..(11)
<223> OTHER INFORMATION: May be fluoro uridine
<220> FEATURE:
<221> NAME/KEY: MOD_RES
<222> LOCATION: (16)..(16)
<223> OTHER INFORMATION: May be fluoro uridine
<220> FEATURE:
<221> NAME/KEY: MOD_RES
<222> LOCATION: (17)..(17)
<223> OTHER INFORMATION: May be fluoro cytidine -continued
<220> FEATURE:
<221> NAME/KEY: MOD_RES
<222> LOCATION: (20)..(20)
<223> OTHER INFORMATION: May be fluoro uridine
<220> FEATURE:
<221> NAME/KEY: MOD_RES
<222> LOCATION: (22)..(22)
<223> OTHER INFORMATION: May be fluoro uridine
<220> FEATURE:
<221> NAME/KEY: MOD_RES
<222> LOCATION: (23)..(23)
<223> OTHER INFORMATION: May be fluoro uridine
<220> FEATURE:
<221> NAME/KEY: MISC_FEATURE
<222> LOCATION: (23)..(25)
<223> OTHER INFORMATION: May be joined through phosphorothioate bonds

<400> SEQUENCE: 2
uagcaccauu ugaaaucagu guuuu 25

<210> SEQ ID NO 3
<211> LENGTH: 24
<212> TYPE: RNA
<213> ORGANISM: Artificial Sequence
<220> FEATURE:
<223> OTHER INFORMATION: miR-29a mimic second-sense-passenger strand
<220> FEATURE:
<221> NAME/KEY: MOD_RES
<222> LOCATION: (1)..(1)
<223> OTHER INFORMATION: May be O-methyl uridine
<220> FEATURE:
<221> NAME/KEY: MOD_RES
<222> LOCATION: (2)..(2)
<223> OTHER INFORMATION: May be O-methyl adenosine

<400> SEQUENCE: 3
uaaccgauuu cagauggugc uauu 24

<210> SEQ ID NO 4
<211> LENGTH: 22
<212> TYPE: RNA
<213> ORGANISM: Artificial Sequence
<220> FEATURE:
<223> OTHER INFORMATION: miR-29a mimic second-sense-passenger strand
<220> FEATURE:
<221> NAME/KEY: MOD_RES
<222> LOCATION: (1)..(1)
<223> OTHER INFORMATION: May be O-methyl uridine
<220> FEATURE:
<221> NAME/KEY: MOD_RES
<222> LOCATION: (2)..(2)
<223> OTHER INFORMATION: May be O-methyl adenosine
<220> FEATURE:
<221> NAME/KEY: MOD_RES
<222> LOCATION: (4)..(4)
<223> OTHER INFORMATION: May be O-methyl cytidine
<220> FEATURE:
<221> NAME/KEY: MOD_RES
<222> LOCATION: (5)..(5)
<223> OTHER INFORMATION: May be O-methyl cytidine
<220> FEATURE:
<221> NAME/KEY: MOD_RES
<222> LOCATION: (7)..(7)
<223> OTHER INFORMATION: May be O-methyl uridine
<220> FEATURE:
<221> NAME/KEY: MOD_RES
<222> LOCATION: (8)..(8)
<223> OTHER INFORMATION: May be O-methyl uridine
<220> FEATURE:
<221> NAME/KEY: MOD_RES
<222> LOCATION: (9)..(9)
<223> OTHER INFORMATION: May be O-methyl uridine
<220> FEATURE:
<221> NAME/KEY: MOD_RES
<222> LOCATION: (11)..(11)

-continued

<223> OTHER INFORMATION: May be O-methyl cytidine
<220> FEATURE:
<221> NAME/KEY: MOD_RES
<222> LOCATION: (15)..(15)
<223> OTHER INFORMATION: May be O-methyl uridine
<220> FEATURE:
<221> NAME/KEY: MOD_RES
<222> LOCATION: (18)..(18)
<223> OTHER INFORMATION: May be O-methyl uridine
<220> FEATURE:
<221> NAME/KEY: MOD_RES
<222> LOCATION: (19)..(19)
<223> OTHER INFORMATION: May be O-methyl cytidine
<220> FEATURE:
<221> NAME/KEY: MOD_RES
<222> LOCATION: (20)..(20)
<223> OTHER INFORMATION: May be O-methyl cytidine
<220> FEATURE:
<221> NAME/KEY: MOD_RES
<222> LOCATION: (21)..(21)
<223> OTHER INFORMATION: May be O-methyl uridine

<400> SEQUENCE: 4
uaaccguuua cagauggucc ua 22

<210> SEQ ID NO 5
<211> LENGTH: 22
<212> TYPE: RNA
<213> ORGANISM: Artificial Sequence
<220> FEATURE:
<223> OTHER INFORMATION: miR-29a mimic second-sense-passenger strand
<220> FEATURE:
<221> NAME/KEY: MOD_RES
<222> LOCATION: (1)..(1)
<223> OTHER INFORMATION: May be O-methyl uridine
<220> FEATURE:
<221> NAME/KEY: MOD_RES
<222> LOCATION: (2)..(2)
<223> OTHER INFORMATION: May be O-methyl adenosine
<220> FEATURE:
<221> NAME/KEY: MOD_RES
<222> LOCATION: (4)..(4)
<223> OTHER INFORMATION: May be O-methyl cytidine
<220> FEATURE:
<221> NAME/KEY: MOD_RES
<222> LOCATION: (5)..(5)
<223> OTHER INFORMATION: May be O-methyl cytidine
<220> FEATURE:
<221> NAME/KEY: MOD_RES
<222> LOCATION: (7)..(7)
<223> OTHER INFORMATION: May be O-methyl uridine
<220> FEATURE:
<221> NAME/KEY: MOD_RES
<222> LOCATION: (8)..(8)
<223> OTHER INFORMATION: May be O-methyl uridine
<220> FEATURE:
<221> NAME/KEY: MOD_RES
<222> LOCATION: (9)..(9)
<223> OTHER INFORMATION: May be O-methyl uridine
<220> FEATURE:
<221> NAME/KEY: MOD_RES
<222> LOCATION: (11)..(11)
<223> OTHER INFORMATION: May be O-methyl cytidine
<220> FEATURE:
<221> NAME/KEY: MOD_RES
<222> LOCATION: (15)..(15)
<223> OTHER INFORMATION: May be O-methyl uridine
<220> FEATURE:
<221> NAME/KEY: MOD_RES
<222> LOCATION: (18)..(18)
<223> OTHER INFORMATION: May be O-methyl uridine
<220> FEATURE:
<221> NAME/KEY: MOD_RES
<222> LOCATION: (19)..(19)
<223> OTHER INFORMATION: May be O-methyl cytidine
<220> FEATURE:
<221> NAME/KEY: MOD_RES -continued
<222> LOCATION: (20)..(20)
<223> OTHER INFORMATION: May be O-methyl cytidine
<220> FEATURE:
<221> NAME/KEY: MOD_RES
<222> LOCATION: (21)..(21)
<223> OTHER INFORMATION: May be O-methyl uridine
<220> FEATURE:
<221> NAME/KEY: MISC_FEATURE
<222> LOCATION: (22)..(22)
<223> OTHER INFORMATION: May be modified with a cholesterol conjugate
with a 6 carbon linker

<400> SEQUENCE: 5
uaaccguuua cagauggucc ua 22

<210> SEQ ID NO 6
<211> LENGTH: 24
<212> TYPE: RNA
<213> ORGANISM: Artificial Sequence
<220> FEATURE:
<223> OTHER INFORMATION: miR-29a mimic first-antisense-guide strand
<220> FEATURE:
<221> NAME/KEY: MISC_FEATURE
<222> LOCATION: (1)..(1)
<223> OTHER INFORMATION: May be modified with a monophosphate moiety

<400> SEQUENCE: 6
uagcaccauc ugaaaucggu uauu 24

<210> SEQ ID NO 7
<211> LENGTH: 24
<212> TYPE: RNA
<213> ORGANISM: Artificial Sequence
<220> FEATURE:
<223> OTHER INFORMATION: miR-29a mimic first-antisense-guide strand
<220> FEATURE:
<221> NAME/KEY: MISC_FEATURE
<222> LOCATION: (1)..(1)
<223> OTHER INFORMATION: May be modified with a monophosphate moiety
<220> FEATURE:
<221> NAME/KEY: MOD_RES
<222> LOCATION: (1)..(1)
<223> OTHER INFORMATION: May be fluoro uridine
<220> FEATURE:
<221> NAME/KEY: MOD_RES
<222> LOCATION: (4)..(4)
<223> OTHER INFORMATION: May be fluoro cytidine
<220> FEATURE:
<221> NAME/KEY: MOD_RES
<222> LOCATION: (6)..(6)
<223> OTHER INFORMATION: May be fluoro cytidine
<220> FEATURE:
<221> NAME/KEY: MOD_RES
<222> LOCATION: (7)..(7)
<223> OTHER INFORMATION: May be fluoro cytidine
<220> FEATURE:
<221> NAME/KEY: MOD_RES
<222> LOCATION: (9)..(9)
<223> OTHER INFORMATION: May be fluoro uridine
<220> FEATURE:
<221> NAME/KEY: MOD_RES
<222> LOCATION: (10)..(10)
<223> OTHER INFORMATION: May be fluoro cytidine
<220> FEATURE:
<221> NAME/KEY: MOD_RES
<222> LOCATION: (11)..(11)
<223> OTHER INFORMATION: May be fluoro uridine
<220> FEATURE:
<221> NAME/KEY: MOD_RES
<222> LOCATION: (16)..(16)
<223> OTHER INFORMATION: May be fluoro uridine
<220> FEATURE:
<221> NAME/KEY: MOD_RES
<222> LOCATION: (17)..(17)
<223> OTHER INFORMATION: May be fluoro cytidine -continued
<220> FEATURE:
<221> NAME/KEY: MOD_RES
<222> LOCATION: (20)..(20)
<223> OTHER INFORMATION: May be fluoro uridine
<220> FEATURE:
<221> NAME/KEY: MOD_RES
<222> LOCATION: (21)..(21)
<223> OTHER INFORMATION: May be fluoro uridine
<220> FEATURE:
<221> NAME/KEY: MISC_FEATURE
<222> LOCATION: (22)..(24)
<223> OTHER INFORMATION: May be joined through phosphorothioate bonds

<400> SEQUENCE: 7
uagcaccauc ugaaaucggu uauu 24

<210> SEQ ID NO 8
<211> LENGTH: 25
<212> TYPE: RNA
<213> ORGANISM: Artificial Sequence
<220> FEATURE:
<223> OTHER INFORMATION: miR-29b mimic second-sense-passenger strand
<220> FEATURE:
<221> NAME/KEY: MOD_RES
<222> LOCATION: (1)..(1)
<223> OTHER INFORMATION: May be O-methyl adenosine
<220> FEATURE:
<221> NAME/KEY: MOD_RES
<222> LOCATION: (2)..(2)
<223> OTHER INFORMATION: May be O-methyl adenosine

<400> SEQUENCE: 8
aacacugauu ucaaauggug cuauu 25

<210> SEQ ID NO 9
<211> LENGTH: 23
<212> TYPE: RNA
<213> ORGANISM: Artificial Sequence
<220> FEATURE:
<223> OTHER INFORMATION: miR-29b mimic second-sense-passenger strand
<220> FEATURE:
<221> NAME/KEY: MOD_RES
<222> LOCATION: (1)..(1)
<223> OTHER INFORMATION: May be O-methyl adenosine
<220> FEATURE:
<221> NAME/KEY: MOD_RES
<222> LOCATION: (2)..(2)
<223> OTHER INFORMATION: May be O-methyl adenosine
<220> FEATURE:
<221> NAME/KEY: MOD_RES
<222> LOCATION: (3)..(3)
<223> OTHER INFORMATION: May be O-methyl cytidine
<220> FEATURE:
<221> NAME/KEY: MOD_RES
<222> LOCATION: (5)..(5)
<223> OTHER INFORMATION: May be O-methyl cytidine
<220> FEATURE:
<221> NAME/KEY: MOD_RES
<222> LOCATION: (6)..(6)
<223> OTHER INFORMATION: May be O-methyl uridine
<220> FEATURE:
<221> NAME/KEY: MOD_RES
<222> LOCATION: (9)..(9)
<223> OTHER INFORMATION: May be O-methyl uridine
<220> FEATURE:
<221> NAME/KEY: MOD_RES
<222> LOCATION: (10)..(10)
<223> OTHER INFORMATION: May be O-methyl uridine
<220> FEATURE:
<221> NAME/KEY: MOD_RES
<222> LOCATION: (11)..(11)
<223> OTHER INFORMATION: May be O-methyl uridine
<220> FEATURE:
<221> NAME/KEY: MOD_RES
<222> LOCATION: (12)..(12)

-continued

<223> OTHER INFORMATION: May be O-methyl cytidine
<220> FEATURE:
<221> NAME/KEY: MOD_RES
<222> LOCATION: (16)..(16)
<223> OTHER INFORMATION: May be O-methyl uridine
<220> FEATURE:
<221> NAME/KEY: MOD_RES
<222> LOCATION: (19)..(19)
<223> OTHER INFORMATION: May be O-methyl uridine
<220> FEATURE:
<221> NAME/KEY: MOD_RES
<222> LOCATION: (21)..(21)
<223> OTHER INFORMATION: May be O-methyl cytidine
<220> FEATURE:
<221> NAME/KEY: MOD_RES
<222> LOCATION: (22)..(22)
<223> OTHER INFORMATION: May be O-methyl uridine
<220> FEATURE:
<221> NAME/KEY: MISC_FEATURE
<222> LOCATION: (23)..(23)
<223> OTHER INFORMATION: May be modified with a cholesterol conjugate
with a 6 carbon linker

<400> SEQUENCE: 9
aacacugauu ucaaauggug cua 23

<210> SEQ ID NO 10
<211> LENGTH: 25
<212> TYPE: RNA
<213> ORGANISM: Artificial Sequence
<220> FEATURE:
<223> OTHER INFORMATION: miR-29b mimic second-sense-passenger strand
<220> FEATURE:
<221> NAME/KEY: MOD_RES
<222> LOCATION: (1)..(1)
<223> OTHER INFORMATION: May be O-methyl adenosine
<220> FEATURE:
<221> NAME/KEY: MOD_RES
<222> LOCATION: (2)..(2)
<223> OTHER INFORMATION: May be O-methyl adenosine
<220> FEATURE:
<221> NAME/KEY: MISC_FEATURE
<222> LOCATION: (23)..(25)
<223> OTHER INFORMATION: May be joined through phosphorothioate bonds
<220> FEATURE:
<221> NAME/KEY: MISC_FEATURE
<222> LOCATION: (25)..(25)
<223> OTHER INFORMATION: May be modified with a cholesterol conjugate
with a 6 carbon linker

<400> SEQUENCE: 10
aacacugauu ucaaauggug cuauu 25

<210> SEQ ID NO 11
<211> LENGTH: 24
<212> TYPE: RNA
<213> ORGANISM: Artificial Sequence
<220> FEATURE:
<223> OTHER INFORMATION: miR-29a mimic second-sense-passenger strand
<220> FEATURE:
<221> NAME/KEY: MOD_RES
<222> LOCATION: (1)..(1)
<223> OTHER INFORMATION: May be O-methyl uridine
<220> FEATURE:
<221> NAME/KEY: MOD_RES
<222> LOCATION: (2)..(2)
<223> OTHER INFORMATION: May be O-methyl adenosine
<220> FEATURE:
<221> NAME/KEY: MISC_FEATURE
<222> LOCATION: (22)..(24)
<223> OTHER INFORMATION: May be joined through phosphorothioate bonds
<220> FEATURE:
<221> NAME/KEY: MISC_FEATURE
<222> LOCATION: (24)..(24)
<223> OTHER INFORMATION: May be modified with a cholesterol conjugate

```
      with a 6 carbon linker

<400> SEQUENCE: 11

uaaccgauuu cagauggugc uauu                                            24


<210> SEQ ID NO 12
<211> LENGTH: 24
<212> TYPE: RNA
<213> ORGANISM: Artificial Sequence
<220> FEATURE:
<223> OTHER INFORMATION: miR-29c mimic second-sense-passenger strand
<220> FEATURE:
<221> NAME/KEY: MOD_RES
<222> LOCATION: (1)..(1)
<223> OTHER INFORMATION: May be O-methyl uridine
<220> FEATURE:
<221> NAME/KEY: MOD_RES
<222> LOCATION: (2)..(2)
<223> OTHER INFORMATION: May be O-methyl adenosine
<220> FEATURE:
<221> NAME/KEY: MISC_FEATURE
<222> LOCATION: (22)..(24)
<223> OTHER INFORMATION: May be joined through phosphorothioate bonds
<220> FEATURE:
<221> NAME/KEY: MISC_FEATURE
<222> LOCATION: (24)..(24)
<223> OTHER INFORMATION: May be modified with a cholesterol conjugate
      with a 6 carbon linker

<400> SEQUENCE: 12

uaaccgauuu caaauggugc uauu                                            24


<210> SEQ ID NO 13
<211> LENGTH: 23
<212> TYPE: RNA
<213> ORGANISM: Artificial Sequence
<220> FEATURE:
<223> OTHER INFORMATION: miR-29b mimic second-sense-passenger strand
<220> FEATURE:
<221> NAME/KEY: MOD_RES
<222> LOCATION: (1)..(1)
<223> OTHER INFORMATION: May be O-methyl adenosine
<220> FEATURE:
<221> NAME/KEY: MOD_RES
<222> LOCATION: (2)..(2)
<223> OTHER INFORMATION: May be O-methyl adenosine
<220> FEATURE:
<221> NAME/KEY: MOD_RES
<222> LOCATION: (3)..(3)
<223> OTHER INFORMATION: May be O-methyl cytidine
<220> FEATURE:
<221> NAME/KEY: MOD_RES
<222> LOCATION: (5)..(5)
<223> OTHER INFORMATION: May be O-methyl cytidine
<220> FEATURE:
<221> NAME/KEY: MOD_RES
<222> LOCATION: (6)..(6)
<223> OTHER INFORMATION: May be O-methyl uridine
<220> FEATURE:
<221> NAME/KEY: MOD_RES
<222> LOCATION: (8)..(8)
<223> OTHER INFORMATION: May be O-methyl uridine
<220> FEATURE:
<221> NAME/KEY: MOD_RES
<222> LOCATION: (9)..(9)
<223> OTHER INFORMATION: May be O-methyl uridine
<220> FEATURE:
<221> NAME/KEY: MOD_RES
<222> LOCATION: (10)..(10)
<223> OTHER INFORMATION: May be O-methyl uridine
<220> FEATURE:
<221> NAME/KEY: MOD_RES
<222> LOCATION: (12)..(12)
<223> OTHER INFORMATION: May be O-methyl cytidine
<220> FEATURE:
```

-continued

<221> NAME/KEY: MOD_RES
<222> LOCATION: (16)..(16)
<223> OTHER INFORMATION: May be O-methyl uridine
<220> FEATURE:
<221> NAME/KEY: MOD_RES
<222> LOCATION: (19)..(19)
<223> OTHER INFORMATION: May be O-methyl uridine
<220> FEATURE:
<221> NAME/KEY: MOD_RES
<222> LOCATION: (20)..(20)
<223> OTHER INFORMATION: May be O-methyl cytidine
<220> FEATURE:
<221> NAME/KEY: MOD_RES
<222> LOCATION: (21)..(21)
<223> OTHER INFORMATION: May be O-methyl cytidine
<220> FEATURE:
<221> NAME/KEY: MOD_RES
<222> LOCATION: (22)..(22)
<223> OTHER INFORMATION: May be O-methyl uridine

<400> SEQUENCE: 13
aacacuguuu acggguggnc cua 23

<210> SEQ ID NO 14
<211> LENGTH: 23
<212> TYPE: RNA
<213> ORGANISM: Artificial Sequence
<220> FEATURE:
<223> OTHER INFORMATION: miR-29b mimic second-sense-passenger strand
<220> FEATURE:
<221> NAME/KEY: MOD_RES
<222> LOCATION: (1)..(1)
<223> OTHER INFORMATION: May be O-methyl adenosine
<220> FEATURE:
<221> NAME/KEY: MOD_RES
<222> LOCATION: (2)..(2)
<223> OTHER INFORMATION: May be O-methyl adenosine
<220> FEATURE:
<221> NAME/KEY: MOD_RES
<222> LOCATION: (3)..(3)
<223> OTHER INFORMATION: May be O-methyl cytidine
<220> FEATURE:
<221> NAME/KEY: MOD_RES
<222> LOCATION: (5)..(5)
<223> OTHER INFORMATION: May be O-methyl cytidine
<220> FEATURE:
<221> NAME/KEY: MOD_RES
<222> LOCATION: (6)..(6)
<223> OTHER INFORMATION: May be O-methyl uridine
<220> FEATURE:
<221> NAME/KEY: MOD_RES
<222> LOCATION: (8)..(8)
<223> OTHER INFORMATION: May be O-methyl uridine
<220> FEATURE:
<221> NAME/KEY: MOD_RES
<222> LOCATION: (9)..(9)
<223> OTHER INFORMATION: May be O-methyl uridine
<220> FEATURE:
<221> NAME/KEY: MOD_RES
<222> LOCATION: (10)..(10)
<223> OTHER INFORMATION: May be O-methyl uridine
<220> FEATURE:
<221> NAME/KEY: MOD_RES
<222> LOCATION: (12)..(12)
<223> OTHER INFORMATION: May be O-methyl cytidine
<220> FEATURE:
<221> NAME/KEY: MOD_RES
<222> LOCATION: (16)..(16)
<223> OTHER INFORMATION: May be O-methyl uridine
<220> FEATURE:
<221> NAME/KEY: MOD_RES
<222> LOCATION: (19)..(19)
<223> OTHER INFORMATION: May be O-methyl uridine
<220> FEATURE:
<221> NAME/KEY: MOD_RES
<222> LOCATION: (20)..(20)
<223> OTHER INFORMATION: May be O-methyl cytidine -continued
<220> FEATURE:
<221> NAME/KEY: MOD_RES
<222> LOCATION: (21)..(21)
<223> OTHER INFORMATION: May be O-methyl cytidine
<220> FEATURE:
<221> NAME/KEY: MOD_RES
<222> LOCATION: (22)..(22)
<223> OTHER INFORMATION: May be O-methyl uridine
<220> FEATURE:
<221> NAME/KEY: MISC_FEATURE
<222> LOCATION: (23)..(23)
<223> OTHER INFORMATION: May be modified with a cholesterol conjugate
with a 6 carbon linker

<400> SEQUENCE: 14
aacacuguuu acgggugguc cua 23

<210> SEQ ID NO 15
<211> LENGTH: 25
<212> TYPE: DNA
<213> ORGANISM: Artificial Sequence
<220> FEATURE:
<223> OTHER INFORMATION: miR-29b mimic second-sense-passenger strand
<220> FEATURE:
<221> NAME/KEY: MOD_RES
<222> LOCATION: (1)..(1)
<223> OTHER INFORMATION: May be O-methyl adenosine
<220> FEATURE:
<221> NAME/KEY: MOD_RES
<222> LOCATION: (2)..(2)
<223> OTHER INFORMATION: May be O-methyl adenosine
<220> FEATURE:
<221> NAME/KEY: MOD_RES
<222> LOCATION: (3)..(3)
<223> OTHER INFORMATION: May be O-methyl cytidine
<220> FEATURE:
<221> NAME/KEY: MOD_RES
<222> LOCATION: (4)..(4)
<223> OTHER INFORMATION: May be adenosine
<220> FEATURE:
<221> NAME/KEY: MOD_RES
<222> LOCATION: (5)..(5)
<223> OTHER INFORMATION: May be O-methyl cytidine
<220> FEATURE:
<221> NAME/KEY: MOD_RES
<222> LOCATION: (6)..(6)
<223> OTHER INFORMATION: May be O-methyl uridine
<220> FEATURE:
<221> NAME/KEY: MOD_RES
<222> LOCATION: (7)..(7)
<223> OTHER INFORMATION: May be guanosine
<220> FEATURE:
<221> NAME/KEY: MOD_RES
<222> LOCATION: (8)..(8)
<223> OTHER INFORMATION: May be O-methyl uridine
<220> FEATURE:
<221> NAME/KEY: MOD_RES
<222> LOCATION: (9)..(9)
<223> OTHER INFORMATION: May be O-methyl uridine
<220> FEATURE:
<221> NAME/KEY: MOD_RES
<222> LOCATION: (10)..(10)
<223> OTHER INFORMATION: May be O-methyl uridine
<220> FEATURE:
<221> NAME/KEY: MOD_RES
<222> LOCATION: (11)..(11)
<223> OTHER INFORMATION: May be adenosine
<220> FEATURE:
<221> NAME/KEY: MOD_RES
<222> LOCATION: (12)..(12)
<223> OTHER INFORMATION: May be O-methyl cytidine
<220> FEATURE:
<221> NAME/KEY: MOD_RES
<222> LOCATION: (13)..(13)
<223> OTHER INFORMATION: May be adenosine
<220> FEATURE:
<221> NAME/KEY: MOD_RES
<222> LOCATION: (14)..(14)
<223> OTHER INFORMATION: May be adenosine
<220> FEATURE:
<221> NAME/KEY: MOD_RES
<222> LOCATION: (15)..(15)
<223> OTHER INFORMATION: May be adenosine
<220> FEATURE:
<221> NAME/KEY: MOD_RES
<222> LOCATION: (16)..(16)
<223> OTHER INFORMATION: May be O-methyl uridine
<220> FEATURE:
<221> NAME/KEY: MOD_RES
<222> LOCATION: (17)..(17)
<223> OTHER INFORMATION: May be guanosine
<220> FEATURE:
<221> NAME/KEY: MOD_RES
<222> LOCATION: (18)..(18)
<223> OTHER INFORMATION: May be guanosine
<220> FEATURE:
<221> NAME/KEY: MOD_RES
<222> LOCATION: (19)..(19)
<223> OTHER INFORMATION: May be O-methyl uridine
<220> FEATURE:
<221> NAME/KEY: MOD_RES
<222> LOCATION: (20)..(20)
<223> OTHER INFORMATION: May be O-methyl cytidine
<220> FEATURE:
<221> NAME/KEY: MOD_RES
<222> LOCATION: (21)..(21)
<223> OTHER INFORMATION: May be O-methyl cytidine
<220> FEATURE:
<221> NAME/KEY: MOD_RES
<222> LOCATION: (22)..(22)
<223> OTHER INFORMATION: May be O-methyl uridine
<220> FEATURE:
<221> NAME/KEY: MOD_RES
<222> LOCATION: (23)..(23)
<223> OTHER INFORMATION: May be adenosine
<220> FEATURE:
<221> NAME/KEY: MISC_FEATURE
<222> LOCATION: (25)..(25)
<223> OTHER INFORMATION: May be modified with a cholesterol conjugate
with a 6 carbon linker

<400> SEQUENCE: 15
aacacuguuu acaaaugguc cuatt 25

<210> SEQ ID NO 16
<211> LENGTH: 25
<212> TYPE: DNA
<213> ORGANISM: Artificial Sequence
<220> FEATURE:
<223> OTHER INFORMATION: miR-29b mimic second-sense-passenger strand
<220> FEATURE:
<221> NAME/KEY: MISC_FEATURE
<222> LOCATION: (1)..(1)
<223> OTHER INFORMATION: May be modified with a cholesterol conjugate
with a 6 carbon linker
<220> FEATURE:
<221> NAME/KEY: MOD_RES
<222> LOCATION: (3)..(3)
<223> OTHER INFORMATION: May be O-methyl adenosine
<220> FEATURE:
<221> NAME/KEY: MOD_RES
<222> LOCATION: (4)..(4)
<223> OTHER INFORMATION: May be O-methyl adenosine
<220> FEATURE:
<221> NAME/KEY: MOD_RES
<222> LOCATION: (5)..(5)
<223> OTHER INFORMATION: May be O-methyl cytidine
<220> FEATURE:
<221> NAME/KEY: MOD_RES
<222> LOCATION: (6)..(6)
<223> OTHER INFORMATION: May be adenosine
<220> FEATURE:
<221> NAME/KEY: MOD_RES
<222> LOCATION: (7)..(7)

-continued

<223> OTHER INFORMATION: May be O-methyl cytidine
<220> FEATURE:
<221> NAME/KEY: MOD_RES
<222> LOCATION: (8)..(8)
<223> OTHER INFORMATION: May be O-methyl uridine
<220> FEATURE:
<221> NAME/KEY: MOD_RES
<222> LOCATION: (9)..(9)
<223> OTHER INFORMATION: May be guanosine
<220> FEATURE:
<221> NAME/KEY: MOD_RES
<222> LOCATION: (10)..(10)
<223> OTHER INFORMATION: May be O-methyl uridine
<220> FEATURE:
<221> NAME/KEY: MOD_RES
<222> LOCATION: (11)..(11)
<223> OTHER INFORMATION: May be O-methyl uridine
<220> FEATURE:
<221> NAME/KEY: MOD_RES
<222> LOCATION: (12)..(12)
<223> OTHER INFORMATION: May be O-methyl uridine
<220> FEATURE:
<221> NAME/KEY: MOD_RES
<222> LOCATION: (13)..(13)
<223> OTHER INFORMATION: May be adenosine
<220> FEATURE:
<221> NAME/KEY: MOD_RES
<222> LOCATION: (14)..(14)
<223> OTHER INFORMATION: May be O-methyl cytidine
<220> FEATURE:
<221> NAME/KEY: MOD_RES
<222> LOCATION: (15)..(15)
<223> OTHER INFORMATION: May be adenosine
<220> FEATURE:
<221> NAME/KEY: MOD_RES
<222> LOCATION: (16)..(16)
<223> OTHER INFORMATION: May be adenosine
<220> FEATURE:
<221> NAME/KEY: MOD_RES
<222> LOCATION: (17)..(17)
<223> OTHER INFORMATION: May be adenosine
<220> FEATURE:
<221> NAME/KEY: MOD_RES
<222> LOCATION: (18)..(18)
<223> OTHER INFORMATION: May be O-methyl uridine
<220> FEATURE:
<221> NAME/KEY: MOD_RES
<222> LOCATION: (19)..(19)
<223> OTHER INFORMATION: May be guanosine
<220> FEATURE:
<221> NAME/KEY: MOD_RES
<222> LOCATION: (20)..(20)
<223> OTHER INFORMATION: May be guanosine
<220> FEATURE:
<221> NAME/KEY: MOD_RES
<222> LOCATION: (21)..(21)
<223> OTHER INFORMATION: May be O-methyl uridine
<220> FEATURE:
<221> NAME/KEY: MOD_RES
<222> LOCATION: (22)..(22)
<223> OTHER INFORMATION: May be O-methyl cytidine
<220> FEATURE:
<221> NAME/KEY: MOD_RES
<222> LOCATION: (23)..(23)
<223> OTHER INFORMATION: May be O-methyl cytidine
<220> FEATURE:
<221> NAME/KEY: MOD_RES
<222> LOCATION: (24)..(24)
<223> OTHER INFORMATION: May be O-methyl uridine
<220> FEATURE:
<221> NAME/KEY: MOD_RES
<222> LOCATION: (25)..(25)
<223> OTHER INFORMATION: May be adenosine

<400> SEQUENCE: 16
ttaacacugu uuacaaaugg uccua 25

```
<210> SEQ ID NO 17
<211> LENGTH: 23
<212> TYPE: RNA
<213> ORGANISM: Artificial Sequence
<220> FEATURE:
<223> OTHER INFORMATION: miR-29b mimic second-sense-passenger strand
<220> FEATURE:
<221> NAME/KEY: MOD_RES
<222> LOCATION: (1)..(1)
<223> OTHER INFORMATION: May be O-methyl adenosine
<220> FEATURE:
<221> NAME/KEY: MOD_RES
<222> LOCATION: (2)..(2)
<223> OTHER INFORMATION: May be O-methyl adenosine
<220> FEATURE:
<221> NAME/KEY: MOD_RES
<222> LOCATION: (3)..(3)
<223> OTHER INFORMATION: May be O-methyl cytidine
<220> FEATURE:
<221> NAME/KEY: MOD_RES
<222> LOCATION: (5)..(5)
<223> OTHER INFORMATION: May be O-methyl cytidine
<220> FEATURE:
<221> NAME/KEY: MOD_RES
<222> LOCATION: (6)..(6)
<223> OTHER INFORMATION: May be O-methyl uridine
<220> FEATURE:
<221> NAME/KEY: MOD_RES
<222> LOCATION: (8)..(8)
<223> OTHER INFORMATION: May be O-methyl uridine
<220> FEATURE:
<221> NAME/KEY: MOD_RES
<222> LOCATION: (9)..(9)
<223> OTHER INFORMATION: May be O-methyl uridine
<220> FEATURE:
<221> NAME/KEY: MOD_RES
<222> LOCATION: (10)..(10)
<223> OTHER INFORMATION: May be O-methyl uridine
<220> FEATURE:
<221> NAME/KEY: MOD_RES
<222> LOCATION: (12)..(12)
<223> OTHER INFORMATION: May be O-methyl cytidine
<220> FEATURE:
<221> NAME/KEY: MOD_RES
<222> LOCATION: (16)..(16)
<223> OTHER INFORMATION: May be O-methyl uridine
<220> FEATURE:
<221> NAME/KEY: MOD_RES
<222> LOCATION: (19)..(19)
<223> OTHER INFORMATION: May be O-methyl uridine
<220> FEATURE:
<221> NAME/KEY: MOD_RES
<222> LOCATION: (20)..(20)
<223> OTHER INFORMATION: May be O-methyl cytidine
<220> FEATURE:
<221> NAME/KEY: MOD_RES
<222> LOCATION: (21)..(21)
<223> OTHER INFORMATION: May be O-methyl cytidine
<220> FEATURE:
<221> NAME/KEY: MOD_RES
<222> LOCATION: (22)..(22)
<223> OTHER INFORMATION: May be O-methyl uridine
<220> FEATURE:
<221> NAME/KEY: MISC_FEATURE
<222> LOCATION: (23)..(23)
<223> OTHER INFORMATION: May be modified with a cholesterol conjugate
      with a 9 carbon linker

<400> SEQUENCE: 17

aacacuguuu acaaaugguc cua                                             23


<210> SEQ ID NO 18
<211> LENGTH: 25
<212> TYPE: RNA
<213> ORGANISM: Artificial Sequence
<220> FEATURE:
<223> OTHER INFORMATION: miR-29b mimic first-antisense-guide strand
```

<220> FEATURE:
<221> NAME/KEY: MISC_FEATURE
<222> LOCATION: (1)..(1)
<223> OTHER INFORMATION: May be modified with a monophosphate moiety

<400> SEQUENCE: 18
uagcaccauu ugaaaucagu guuuu 25

<210> SEQ ID NO 19
<211> LENGTH: 25
<212> TYPE: RNA
<213> ORGANISM: Artificial Sequence
<220> FEATURE:
<223> OTHER INFORMATION: miR-29b mimic first-antisense-guide strand
<220> FEATURE:
<221> NAME/KEY: MOD_RES
<222> LOCATION: (1)..(1)
<223> OTHER INFORMATION: May be fluoro uridine
<220> FEATURE:
<221> NAME/KEY: MOD_RES
<222> LOCATION: (4)..(4)
<223> OTHER INFORMATION: May be fluoro cytidine
<220> FEATURE:
<221> NAME/KEY: MOD_RES
<222> LOCATION: (6)..(6)
<223> OTHER INFORMATION: May be fluoro cytidine
<220> FEATURE:
<221> NAME/KEY: MOD_RES
<222> LOCATION: (7)..(7)
<223> OTHER INFORMATION: May be fluoro cytidine
<220> FEATURE:
<221> NAME/KEY: MOD_RES
<222> LOCATION: (9)..(9)
<223> OTHER INFORMATION: May be fluoro uridine
<220> FEATURE:
<221> NAME/KEY: MOD_RES
<222> LOCATION: (10)..(10)
<223> OTHER INFORMATION: May be fluoro uridine
<220> FEATURE:
<221> NAME/KEY: MOD_RES
<222> LOCATION: (11)..(11)
<223> OTHER INFORMATION: May be fluoro uridine
<220> FEATURE:
<221> NAME/KEY: MOD_RES
<222> LOCATION: (16)..(16)
<223> OTHER INFORMATION: May be fluoro uridine
<220> FEATURE:
<221> NAME/KEY: MOD_RES
<222> LOCATION: (17)..(17)
<223> OTHER INFORMATION: May be fluoro cytidine
<220> FEATURE:
<221> NAME/KEY: MOD_RES
<222> LOCATION: (20)..(20)
<223> OTHER INFORMATION: May be fluoro uridine
<220> FEATURE:
<221> NAME/KEY: MOD_RES
<222> LOCATION: (22)..(22)
<223> OTHER INFORMATION: May be fluoro uridine
<220> FEATURE:
<221> NAME/KEY: MOD_RES
<222> LOCATION: (23)..(23)
<223> OTHER INFORMATION: May be fluoro uridine
<220> FEATURE:
<221> NAME/KEY: MISC_FEATURE
<222> LOCATION: (23)..(25)
<223> OTHER INFORMATION: May be joined through phosphorothioate bonds

<400> SEQUENCE: 19
uagcaccauu ugaaaucagu guuuu 25

<210> SEQ ID NO 20
<211> LENGTH: 25
<212> TYPE: RNA
<213> ORGANISM: Artificial Sequence
<220> FEATURE:

-continued

<223> OTHER INFORMATION: miR-29b mimic first-antisense-guide strand
<220> FEATURE:
<221> NAME/KEY: MISC_FEATURE
<222> LOCATION: (1)..(1)
<223> OTHER INFORMATION: May be modified with a monophosphate moiety
<220> FEATURE:
<221> NAME/KEY: MOD_RES
<222> LOCATION: (1)..(1)
<223> OTHER INFORMATION: May be fluoro uridine
<220> FEATURE:
<221> NAME/KEY: MOD_RES
<222> LOCATION: (4)..(4)
<223> OTHER INFORMATION: May be fluoro cytidine
<220> FEATURE:
<221> NAME/KEY: MOD_RES
<222> LOCATION: (6)..(6)
<223> OTHER INFORMATION: May be fluoro cytidine
<220> FEATURE:
<221> NAME/KEY: MOD_RES
<222> LOCATION: (7)..(7)
<223> OTHER INFORMATION: May be fluoro cytidine
<220> FEATURE:
<221> NAME/KEY: MOD_RES
<222> LOCATION: (9)..(9)
<223> OTHER INFORMATION: May be fluoro cytidine
<220> FEATURE:
<221> NAME/KEY: MOD_RES
<222> LOCATION: (10)..(10)
<223> OTHER INFORMATION: May be fluoro cytidine
<220> FEATURE:
<221> NAME/KEY: MOD_RES
<222> LOCATION: (11)..(11)
<223> OTHER INFORMATION: May be fluoro cytidine
<220> FEATURE:
<221> NAME/KEY: MOD_RES
<222> LOCATION: (16)..(16)
<223> OTHER INFORMATION: May be fluoro uridine
<220> FEATURE:
<221> NAME/KEY: MOD_RES
<222> LOCATION: (17)..(17)
<223> OTHER INFORMATION: May be fluoro cytidine
<220> FEATURE:
<221> NAME/KEY: MOD_RES
<222> LOCATION: (20)..(20)
<223> OTHER INFORMATION: May be fluoro uridine
<220> FEATURE:
<221> NAME/KEY: MOD_RES
<222> LOCATION: (22)..(22)
<223> OTHER INFORMATION: May be fluoro uridine
<220> FEATURE:
<221> NAME/KEY: MOD_RES
<222> LOCATION: (23)..(23)
<223> OTHER INFORMATION: May be fluoro uridine
<220> FEATURE:
<221> NAME/KEY: MISC_FEATURE
<222> LOCATION: (23)..(25)
<223> OTHER INFORMATION: May be joined through phosphorothioate bonds

<400> SEQUENCE: 20
uagcaccacc cgaaaucagu guuuu 25

<210> SEQ ID NO 21
<211> LENGTH: 25
<212> TYPE: RNA
<213> ORGANISM: Artificial Sequence
<220> FEATURE:
<223> OTHER INFORMATION: miR-29b mimic first-antisense-guide strand

<400> SEQUENCE: 21
uagcaccauu ugaaaucagu guuuu 25

<210> SEQ ID NO 22
<211> LENGTH: 24
<212> TYPE: RNA
<213> ORGANISM: Artificial Sequence -continued
<220> FEATURE:
<223> OTHER INFORMATION: miR-29c mimic second-sense-passenger strand
<220> FEATURE:
<221> NAME/KEY: MOD_RES
<222> LOCATION: (1)..(1)
<223> OTHER INFORMATION: May be O-methyl uridine
<220> FEATURE:
<221> NAME/KEY: MOD_RES
<222> LOCATION: (2)..(2)
<223> OTHER INFORMATION: May be O-methyl adenosine

<400> SEQUENCE: 22
uaaccgauuu caaauggugc uauu 24

<210> SEQ ID NO 23
<211> LENGTH: 22
<212> TYPE: RNA
<213> ORGANISM: Artificial Sequence
<220> FEATURE:
<223> OTHER INFORMATION: miR-29c mimic second-sense-passenger strand
<220> FEATURE:
<221> NAME/KEY: MOD_RES
<222> LOCATION: (1)..(1)
<223> OTHER INFORMATION: May be O-methyl uridine
<220> FEATURE:
<221> NAME/KEY: MOD_RES
<222> LOCATION: (2)..(2)
<223> OTHER INFORMATION: May be O-methyl adenosine
<220> FEATURE:
<221> NAME/KEY: MOD_RES
<222> LOCATION: (4)..(4)
<223> OTHER INFORMATION: May be O-methyl cytidine
<220> FEATURE:
<221> NAME/KEY: MOD_RES
<222> LOCATION: (5)..(5)
<223> OTHER INFORMATION: May be O-methyl cytidine
<220> FEATURE:
<221> NAME/KEY: MOD_RES
<222> LOCATION: (7)..(7)
<223> OTHER INFORMATION: May be O-methyl uridine
<220> FEATURE:
<221> NAME/KEY: MOD_RES
<222> LOCATION: (8)..(8)
<223> OTHER INFORMATION: May be O-methyl uridine
<220> FEATURE:
<221> NAME/KEY: MOD_RES
<222> LOCATION: (9)..(9)
<223> OTHER INFORMATION: May be O-methyl uridine
<220> FEATURE:
<221> NAME/KEY: MOD_RES
<222> LOCATION: (11)..(11)
<223> OTHER INFORMATION: May be O-methyl cytidine
<220> FEATURE:
<221> NAME/KEY: MOD_RES
<222> LOCATION: (15)..(15)
<223> OTHER INFORMATION: May be O-methyl uridine
<220> FEATURE:
<221> NAME/KEY: MOD_RES
<222> LOCATION: (18)..(18)
<223> OTHER INFORMATION: May be O-methyl uridine
<220> FEATURE:
<221> NAME/KEY: MOD_RES
<222> LOCATION: (19)..(19)
<223> OTHER INFORMATION: May be O-methyl cytidine
<220> FEATURE:
<221> NAME/KEY: MOD_RES
<222> LOCATION: (20)..(20)
<223> OTHER INFORMATION: May be O-methyl cytidine
<220> FEATURE:
<221> NAME/KEY: MOD_RES
<222> LOCATION: (21)..(21)
<223> OTHER INFORMATION: May be O-methyl uridine

<400> SEQUENCE: 23
uaaccguuua caaauggucc ua 22

-continued

<210> SEQ ID NO 24
<211> LENGTH: 22
<212> TYPE: RNA
<213> ORGANISM: Artificial Sequence
<220> FEATURE:
<223> OTHER INFORMATION: miR-29c mimic second-sense-passenger strand
<220> FEATURE:
<221> NAME/KEY: MOD_RES
<222> LOCATION: (1)..(1)
<223> OTHER INFORMATION: May be O-methyl uridine
<220> FEATURE:
<221> NAME/KEY: MOD_RES
<222> LOCATION: (2)..(2)
<223> OTHER INFORMATION: May be O-methyl adenosine
<220> FEATURE:
<221> NAME/KEY: MOD_RES
<222> LOCATION: (4)..(4)
<223> OTHER INFORMATION: May be O-methyl cytidine
<220> FEATURE:
<221> NAME/KEY: MOD_RES
<222> LOCATION: (5)..(5)
<223> OTHER INFORMATION: May be O-methyl cytidine
<220> FEATURE:
<221> NAME/KEY: MOD_RES
<222> LOCATION: (7)..(7)
<223> OTHER INFORMATION: May be O-methyl uridine
<220> FEATURE:
<221> NAME/KEY: MOD_RES
<222> LOCATION: (8)..(8)
<223> OTHER INFORMATION: May be O-methyl uridine
<220> FEATURE:
<221> NAME/KEY: MOD_RES
<222> LOCATION: (9)..(9)
<223> OTHER INFORMATION: May be O-methyl uridine
<220> FEATURE:
<221> NAME/KEY: MOD_RES
<222> LOCATION: (11)..(11)
<223> OTHER INFORMATION: May be O-methyl cytidine
<220> FEATURE:
<221> NAME/KEY: MOD_RES
<222> LOCATION: (15)..(15)
<223> OTHER INFORMATION: May be O-methyl uridine
<220> FEATURE:
<221> NAME/KEY: MOD_RES
<222> LOCATION: (18)..(18)
<223> OTHER INFORMATION: May be O-methyl uridine
<220> FEATURE:
<221> NAME/KEY: MOD_RES
<222> LOCATION: (19)..(19)
<223> OTHER INFORMATION: May be O-methyl cytidine
<220> FEATURE:
<221> NAME/KEY: MOD_RES
<222> LOCATION: (20)..(20)
<223> OTHER INFORMATION: May be O-methyl cytidine
<220> FEATURE:
<221> NAME/KEY: MOD_RES
<222> LOCATION: (21)..(21)
<223> OTHER INFORMATION: May be O-methyl uridine
<220> FEATURE:
<221> NAME/KEY: MISC_FEATURE
<222> LOCATION: (22)..(22)
<223> OTHER INFORMATION: May be modified with a cholesterol conjugate
with a 6 carbon linker

<400> SEQUENCE: 24
uaaccguuua caaauggucc ua 22

<210> SEQ ID NO 25
<211> LENGTH: 24
<212> TYPE: RNA
<213> ORGANISM: Artificial Sequence
<220> FEATURE:
<223> OTHER INFORMATION: miR-29c mimic first-antisense-guide strand
<220> FEATURE:
<221> NAME/KEY: MISC_FEATURE
<222> LOCATION: (1)..(1)

<223> OTHER INFORMATION: May be modified with a monophosphate moiety

<400> SEQUENCE: 25
uagcaccauu ugaaaucggu uauu 24

<210> SEQ ID NO 26
<211> LENGTH: 24
<212> TYPE: RNA
<213> ORGANISM: Artificial Sequence
<220> FEATURE:
<223> OTHER INFORMATION: miR-29c mimic first-antisense-guide strand
<220> FEATURE:
<221> NAME/KEY: MISC_FEATURE
<222> LOCATION: (1)..(1)
<223> OTHER INFORMATION: May be modified with a monophosphate moiety
<220> FEATURE:
<221> NAME/KEY: MOD_RES
<222> LOCATION: (1)..(1)
<223> OTHER INFORMATION: May be fluoro uridine
<220> FEATURE:
<221> NAME/KEY: MOD_RES
<222> LOCATION: (4)..(4)
<223> OTHER INFORMATION: May be fluoro cytidine
<220> FEATURE:
<221> NAME/KEY: MOD_RES
<222> LOCATION: (6)..(6)
<223> OTHER INFORMATION: May be fluoro cytidine
<220> FEATURE:
<221> NAME/KEY: MOD_RES
<222> LOCATION: (7)..(7)
<223> OTHER INFORMATION: May be fluoro cytidine
<220> FEATURE:
<221> NAME/KEY: MOD_RES
<222> LOCATION: (9)..(9)
<223> OTHER INFORMATION: May be fluoro uridine
<220> FEATURE:
<221> NAME/KEY: MOD_RES
<222> LOCATION: (10)..(10)
<223> OTHER INFORMATION: May be fluoro uridine
<220> FEATURE:
<221> NAME/KEY: MOD_RES
<222> LOCATION: (11)..(11)
<223> OTHER INFORMATION: May be fluoro uridine
<220> FEATURE:
<221> NAME/KEY: MOD_RES
<222> LOCATION: (16)..(16)
<223> OTHER INFORMATION: May be fluoro uridine
<220> FEATURE:
<221> NAME/KEY: MOD_RES
<222> LOCATION: (17)..(17)
<223> OTHER INFORMATION: May be fluoro cytidine
<220> FEATURE:
<221> NAME/KEY: MOD_RES
<222> LOCATION: (20)..(20)
<223> OTHER INFORMATION: May be fluoro uridine
<220> FEATURE:
<221> NAME/KEY: MOD_RES
<222> LOCATION: (21)..(21)
<223> OTHER INFORMATION: May be fluoro uridine
<220> FEATURE:
<221> NAME/KEY: MISC_FEATURE
<222> LOCATION: (22)..(24)
<223> OTHER INFORMATION: May be joined through phosphorothioate bonds

<400> SEQUENCE: 26
uagcaccauu ugaaaucggu uauu 24

<210> SEQ ID NO 27
<211> LENGTH: 24
<212> TYPE: RNA
<213> ORGANISM: Artificial Sequence
<220> FEATURE:
<223> OTHER INFORMATION: miR-29a mimic first-antisense-guide strand
<220> FEATURE:
<221> NAME/KEY: MOD_RES
<222> LOCATION: (1)..(1)
<223> OTHER INFORMATION: May be fluoro uridine
<220> FEATURE:
<221> NAME/KEY: MOD_RES
<222> LOCATION: (4)..(4)
<223> OTHER INFORMATION: May be fluoro cytidine
<220> FEATURE:
<221> NAME/KEY: MOD_RES
<222> LOCATION: (6)..(6)
<223> OTHER INFORMATION: May be fluoro cytidine
<220> FEATURE:
<221> NAME/KEY: MOD_RES
<222> LOCATION: (7)..(7)
<223> OTHER INFORMATION: May be fluoro cytidine
<220> FEATURE:
<221> NAME/KEY: MOD_RES
<222> LOCATION: (9)..(9)
<223> OTHER INFORMATION: May be fluoro uridine
<220> FEATURE:
<221> NAME/KEY: MOD_RES
<222> LOCATION: (10)..(10)
<223> OTHER INFORMATION: May be fluoro cytidine
<220> FEATURE:
<221> NAME/KEY: MOD_RES
<222> LOCATION: (11)..(11)
<223> OTHER INFORMATION: May be fluoro uridine
<220> FEATURE:
<221> NAME/KEY: MOD_RES
<222> LOCATION: (16)..(16)
<223> OTHER INFORMATION: May be fluoro uridine
<220> FEATURE:
<221> NAME/KEY: MOD_RES
<222> LOCATION: (17)..(17)
<223> OTHER INFORMATION: May be fluoro cytidine
<220> FEATURE:
<221> NAME/KEY: MOD_RES
<222> LOCATION: (20)..(20)
<223> OTHER INFORMATION: May be fluoro uridine
<220> FEATURE:
<221> NAME/KEY: MOD_RES
<222> LOCATION: (21)..(21)
<223> OTHER INFORMATION: May be fluoro uridine
<220> FEATURE:
<221> NAME/KEY: MISC_FEATURE
<222> LOCATION: (22)..(24)
<223> OTHER INFORMATION: May be joined through phosphorothioate bonds

<400> SEQUENCE: 27
uagcaccauc ugaaaucggu uauu 24

<210> SEQ ID NO 28
<211> LENGTH: 23
<212> TYPE: RNA
<213> ORGANISM: Artificial Sequence
<220> FEATURE:
<223> OTHER INFORMATION: miR-29b mimic second-sense-passenger strand
<220> FEATURE:
<221> NAME/KEY: MOD_RES
<222> LOCATION: (2)..(2)
<223> OTHER INFORMATION: May be O-methyl adenosine
<220> FEATURE:
<221> NAME/KEY: MOD_RES
<222> LOCATION: (4)..(4)
<223> OTHER INFORMATION: May be O-methyl adenosine
<220> FEATURE:
<221> NAME/KEY: MOD_RES
<222> LOCATION: (6)..(6)
<223> OTHER INFORMATION: May be O-methyl uridine
<220> FEATURE:
<221> NAME/KEY: MOD_RES
<222> LOCATION: (8)..(8)
<223> OTHER INFORMATION: May be O-methyl adenosine
<220> FEATURE:
<221> NAME/KEY: MOD_RES
<222> LOCATION: (10)..(10)
<223> OTHER INFORMATION: May be O-methyl uridine
<220> FEATURE:

<221> NAME/KEY: MOD_RES
<222> LOCATION: (12)..(12)
<223> OTHER INFORMATION: May be O-methyl cytidine
<220> FEATURE:
<221> NAME/KEY: MOD_RES
<222> LOCATION: (14)..(14)
<223> OTHER INFORMATION: May be O-methyl adenosine
<220> FEATURE:
<221> NAME/KEY: MOD_RES
<222> LOCATION: (16)..(16)
<223> OTHER INFORMATION: May be O-methyl uridine
<220> FEATURE:
<221> NAME/KEY: MOD_RES
<222> LOCATION: (18)..(18)
<223> OTHER INFORMATION: May be O-methyl guanosine
<220> FEATURE:
<221> NAME/KEY: MOD_RES
<222> LOCATION: (20)..(20)
<223> OTHER INFORMATION: May be O-methyl guanosine
<220> FEATURE:
<221> NAME/KEY: MOD_RES
<222> LOCATION: (22)..(22)
<223> OTHER INFORMATION: May be O-methyl uridine
<220> FEATURE:
<221> NAME/KEY: MISC_FEATURE
<222> LOCATION: (23)..(23)
<223> OTHER INFORMATION: May be modified with a cholesterol conjugate
with a 6 carbon linker

<400> SEQUENCE: 28
aacacugauu ucaaauggug cua 23

<210> SEQ ID NO 29
<211> LENGTH: 25
<212> TYPE: RNA
<213> ORGANISM: Artificial Sequence
<220> FEATURE:
<223> OTHER INFORMATION: miR-29b mimic second-sense-passenger strand
<220> FEATURE:
<221> NAME/KEY: MOD_RES
<222> LOCATION: (2)..(2)
<223> OTHER INFORMATION: May be O-methyl adenosine
<220> FEATURE:
<221> NAME/KEY: MOD_RES
<222> LOCATION: (4)..(4)
<223> OTHER INFORMATION: May be O-methyl adenosine
<220> FEATURE:
<221> NAME/KEY: MOD_RES
<222> LOCATION: (6)..(6)
<223> OTHER INFORMATION: May be O-methyl uridine
<220> FEATURE:
<221> NAME/KEY: MOD_RES
<222> LOCATION: (8)..(8)
<223> OTHER INFORMATION: May be O-methyl adenosine
<220> FEATURE:
<221> NAME/KEY: MOD_RES
<222> LOCATION: (10)..(10)
<223> OTHER INFORMATION: May be O-methyl uridine
<220> FEATURE:
<221> NAME/KEY: MOD_RES
<222> LOCATION: (12)..(12)
<223> OTHER INFORMATION: May be O-methyl cytidine
<220> FEATURE:
<221> NAME/KEY: MOD_RES
<222> LOCATION: (14)..(14)
<223> OTHER INFORMATION: May be O-methyl adenosine
<220> FEATURE:
<221> NAME/KEY: MOD_RES
<222> LOCATION: (16)..(16)
<223> OTHER INFORMATION: May be O-methyl uridine
<220> FEATURE:
<221> NAME/KEY: MOD_RES
<222> LOCATION: (18)..(18)
<223> OTHER INFORMATION: May be O-methyl guanosine
<220> FEATURE:
<221> NAME/KEY: MOD_RES
<222> LOCATION: (20)..(20)

<223> OTHER INFORMATION: May be O-methyl guanosine
<220> FEATURE:
<221> NAME/KEY: MOD_RES
<222> LOCATION: (22)..(22)
<223> OTHER INFORMATION: May be O-methyl uridine
<220> FEATURE:
<221> NAME/KEY: MISC_FEATURE
<222> LOCATION: (23)..(25)
<223> OTHER INFORMATION: May be joined through phosphorothioate bonds
<220> FEATURE:
<221> NAME/KEY: MISC_FEATURE
<222> LOCATION: (25)..(25)
<223> OTHER INFORMATION: May be modified with a cholesterol conjugate
with a 6 carbon linker

<400> SEQUENCE: 29
aacacugauu ucaaauggug cuauu 25

<210> SEQ ID NO 30
<211> LENGTH: 23
<212> TYPE: RNA
<213> ORGANISM: Artificial Sequence
<220> FEATURE:
<223> OTHER INFORMATION: miR-29b mimic second-sense-passenger strand
<220> FEATURE:
<221> NAME/KEY: MOD_RES
<222> LOCATION: (1)..(1)
<223> OTHER INFORMATION: May be O-methyl adenosine
<220> FEATURE:
<221> NAME/KEY: MOD_RES
<222> LOCATION: (2)..(2)
<223> OTHER INFORMATION: May be O-methyl adenosine
<220> FEATURE:
<221> NAME/KEY: MOD_RES
<222> LOCATION: (3)..(3)
<223> OTHER INFORMATION: May be O-methyl cytidine
<220> FEATURE:
<221> NAME/KEY: MOD_RES
<222> LOCATION: (5)..(5)
<223> OTHER INFORMATION: May be O-methyl cytidine
<220> FEATURE:
<221> NAME/KEY: MOD_RES
<222> LOCATION: (6)..(6)
<223> OTHER INFORMATION: May be O-methyl uridine
<220> FEATURE:
<221> NAME/KEY: MOD_RES
<222> LOCATION: (8)..(8)
<223> OTHER INFORMATION: May be O-methyl uridine
<220> FEATURE:
<221> NAME/KEY: MOD_RES
<222> LOCATION: (9)..(9)
<223> OTHER INFORMATION: May be O-methyl uridine
<220> FEATURE:
<221> NAME/KEY: MOD_RES
<222> LOCATION: (10)..(10)
<223> OTHER INFORMATION: May be O-methyl uridine
<220> FEATURE:
<221> NAME/KEY: MOD_RES
<222> LOCATION: (12)..(12)
<223> OTHER INFORMATION: May be O-methyl cytidine
<220> FEATURE:
<221> NAME/KEY: MOD_RES
<222> LOCATION: (16)..(16)
<223> OTHER INFORMATION: May be O-methyl uridine
<220> FEATURE:
<221> NAME/KEY: MOD_RES
<222> LOCATION: (19)..(19)
<223> OTHER INFORMATION: May be O-methyl uridine
<220> FEATURE:
<221> NAME/KEY: MOD_RES
<222> LOCATION: (20)..(20)
<223> OTHER INFORMATION: May be O-methyl cytidine
<220> FEATURE:
<221> NAME/KEY: MOD_RES
<222> LOCATION: (21)..(21)
<223> OTHER INFORMATION: May be O-methyl cytidine
<220> FEATURE:

-continued

<221> NAME/KEY: MOD_RES
<222> LOCATION: (22)..(22)
<223> OTHER INFORMATION: May be O-methyl uridine
<220> FEATURE:
<221> NAME/KEY: MOD_RES
<222> LOCATION: (23)..(23)
<223> OTHER INFORMATION: May be modified with a cholesterol conjugate
with a tetraethylene glycol moiety

<400> SEQUENCE: 30
aacacuguuu acaaaugguc cua 23

<210> SEQ ID NO 31
<211> LENGTH: 23
<212> TYPE: RNA
<213> ORGANISM: Artificial Sequence
<220> FEATURE:
<223> OTHER INFORMATION: miR-29b mimic first-antisense-guide strand
<220> FEATURE:
<221> NAME/KEY: MOD_RES
<222> LOCATION: (1)..(1)
<223> OTHER INFORMATION: May be O-methyl uridine
<220> FEATURE:
<221> NAME/KEY: MOD_RES
<222> LOCATION: (3)..(3)
<223> OTHER INFORMATION: May be O-methyl guanosine
<220> FEATURE:
<221> NAME/KEY: MOD_RES
<222> LOCATION: (5)..(5)
<223> OTHER INFORMATION: May be O-methyl adenosine
<220> FEATURE:
<221> NAME/KEY: MOD_RES
<222> LOCATION: (7)..(7)
<223> OTHER INFORMATION: May be O-methyl cytidine
<220> FEATURE:
<221> NAME/KEY: MOD_RES
<222> LOCATION: (9)..(9)
<223> OTHER INFORMATION: May be O-methyl uridine
<220> FEATURE:
<221> NAME/KEY: MOD_RES
<222> LOCATION: (11)..(11)
<223> OTHER INFORMATION: May be O-methyl uridine
<220> FEATURE:
<221> NAME/KEY: MOD_RES
<222> LOCATION: (13)..(13)
<223> OTHER INFORMATION: May be O-methyl adenosine
<220> FEATURE:
<221> NAME/KEY: MOD_RES
<222> LOCATION: (15)..(15)
<223> OTHER INFORMATION: May be O-methyl adenosine
<220> FEATURE:
<221> NAME/KEY: MOD_RES
<222> LOCATION: (17)..(17)
<223> OTHER INFORMATION: May be O-methyl cytidine
<220> FEATURE:
<221> NAME/KEY: MOD_RES
<222> LOCATION: (19)..(19)
<223> OTHER INFORMATION: May be O-methyl guanosine
<220> FEATURE:
<221> NAME/KEY: MOD_RES
<222> LOCATION: (21)..(21)
<223> OTHER INFORMATION: May be O-methyl guanosine
<220> FEATURE:
<221> NAME/KEY: MOD_RES
<222> LOCATION: (23)..(23)
<223> OTHER INFORMATION: May be O-methyl uridine

<400> SEQUENCE: 31
uagcaccauu ugaaaucagu guu 23

<210> SEQ ID NO 32
<211> LENGTH: 25
<212> TYPE: RNA
<213> ORGANISM: Artificial Sequence
<220> FEATURE:

<223> OTHER INFORMATION: miR-29b mimic first-antisense-guide strand
<220> FEATURE:
<221> NAME/KEY: MOD_RES
<222> LOCATION: (1)..(1)
<223> OTHER INFORMATION: May be O-methyl uridine
<220> FEATURE:
<221> NAME/KEY: MOD_RES
<222> LOCATION: (3)..(3)
<223> OTHER INFORMATION: May be O-methyl guanosine
<220> FEATURE:
<221> NAME/KEY: MOD_RES
<222> LOCATION: (5)..(5)
<223> OTHER INFORMATION: May be O-methyl adenosine
<220> FEATURE:
<221> NAME/KEY: MOD_RES
<222> LOCATION: (7)..(7)
<223> OTHER INFORMATION: May be O-methyl cytidine
<220> FEATURE:
<221> NAME/KEY: MOD_RES
<222> LOCATION: (9)..(9)
<223> OTHER INFORMATION: May be O-methyl uridine
<220> FEATURE:
<221> NAME/KEY: MOD_RES
<222> LOCATION: (11)..(11)
<223> OTHER INFORMATION: May be O-methyl uridine
<220> FEATURE:
<221> NAME/KEY: MOD_RES
<222> LOCATION: (13)..(13)
<223> OTHER INFORMATION: May be O-methyl adenosine
<220> FEATURE:
<221> NAME/KEY: MOD_RES
<222> LOCATION: (15)..(15)
<223> OTHER INFORMATION: May be O-methyl adenosine
<220> FEATURE:
<221> NAME/KEY: MOD_RES
<222> LOCATION: (17)..(17)
<223> OTHER INFORMATION: May be O-methyl cytidine
<220> FEATURE:
<221> NAME/KEY: MOD_RES
<222> LOCATION: (19)..(19)
<223> OTHER INFORMATION: May be O-methyl guanosine
<220> FEATURE:
<221> NAME/KEY: MOD_RES
<222> LOCATION: (21)..(21)
<223> OTHER INFORMATION: May be O-methyl guanosine
<220> FEATURE:
<221> NAME/KEY: MISC_FEATURE
<222> LOCATION: (23)..(25)
<223> OTHER INFORMATION: May be joined through phosphorothioate bonds
<220> FEATURE:
<221> NAME/KEY: MOD_RES
<222> LOCATION: (23)..(23)
<223> OTHER INFORMATION: May be O-methyl uridine

<400> SEQUENCE: 32
uagcaccauu ugaaaucagu guuuu 25

<210> SEQ ID NO 33
<211> LENGTH: 25
<212> TYPE: RNA
<213> ORGANISM: Artificial Sequence
<220> FEATURE:
<223> OTHER INFORMATION: miR-29b mimic first-antisense-guide strand
<220> FEATURE:
<221> NAME/KEY: MOD_RES
<222> LOCATION: (1)..(1)
<223> OTHER INFORMATION: May be O-methyl uridine
<220> FEATURE:
<221> NAME/KEY: MOD_RES
<222> LOCATION: (4)..(4)
<223> OTHER INFORMATION: May be O-methyl cytidine
<220> FEATURE:
<221> NAME/KEY: MOD_RES
<222> LOCATION: (6)..(6)
<223> OTHER INFORMATION: May be O-methyl cytidine
<220> FEATURE:
<221> NAME/KEY: MOD_RES -continued
<222> LOCATION: (7)..(7)
<223> OTHER INFORMATION: May be O-methyl cytidine
<220> FEATURE:
<221> NAME/KEY: MOD_RES
<222> LOCATION: (9)..(9)
<223> OTHER INFORMATION: May be O-methyl uridine
<220> FEATURE:
<221> NAME/KEY: MOD_RES
<222> LOCATION: (10)..(10)
<223> OTHER INFORMATION: May be O-methyl uridine
<220> FEATURE:
<221> NAME/KEY: MOD_RES
<222> LOCATION: (11)..(11)
<223> OTHER INFORMATION: May be O-methyl uridine
<220> FEATURE:
<221> NAME/KEY: MOD_RES
<222> LOCATION: (16)..(16)
<223> OTHER INFORMATION: May be O-methyl uridine
<220> FEATURE:
<221> NAME/KEY: MOD_RES
<222> LOCATION: (17)..(17)
<223> OTHER INFORMATION: May be O-methyl cytidine
<220> FEATURE:
<221> NAME/KEY: MOD_RES
<222> LOCATION: (20)..(20)
<223> OTHER INFORMATION: May be O-methyl uridine
<220> FEATURE:
<221> NAME/KEY: MOD_RES
<222> LOCATION: (22)..(22)
<223> OTHER INFORMATION: May be O-methyl uridine
<220> FEATURE:
<221> NAME/KEY: MISC_FEATURE
<222> LOCATION: (23)..(25)
<223> OTHER INFORMATION: May be joined through phosphorothioate bonds
<220> FEATURE:
<221> NAME/KEY: MOD_RES
<222> LOCATION: (23)..(23)
<223> OTHER INFORMATION: May be O-methyl uridine

<400> SEQUENCE: 33
uagcaccauu ugaaaucagu guuuu 25

<210> SEQ ID NO 34
<211> LENGTH: 23
<212> TYPE: RNA
<213> ORGANISM: Artificial Sequence
<220> FEATURE:
<223> OTHER INFORMATION: miR-29b mimic first-antisense-guide strand
<220> FEATURE:
<221> NAME/KEY: MOD_RES
<222> LOCATION: (1)..(1)
<223> OTHER INFORMATION: May be fluoro uridine
<220> FEATURE:
<221> NAME/KEY: MOD_RES
<222> LOCATION: (4)..(4)
<223> OTHER INFORMATION: May be fluoro cytidine
<220> FEATURE:
<221> NAME/KEY: MOD_RES
<222> LOCATION: (6)..(6)
<223> OTHER INFORMATION: May be fluoro cytidine
<220> FEATURE:
<221> NAME/KEY: MOD_RES
<222> LOCATION: (7)..(7)
<223> OTHER INFORMATION: May be fluoro cytidine
<220> FEATURE:
<221> NAME/KEY: MOD_RES
<222> LOCATION: (9)..(9)
<223> OTHER INFORMATION: May be fluoro uridine
<220> FEATURE:
<221> NAME/KEY: MOD_RES
<222> LOCATION: (10)..(10)
<223> OTHER INFORMATION: May be fluoro uridine
<220> FEATURE:
<221> NAME/KEY: MOD_RES
<222> LOCATION: (11)..(11)
<223> OTHER INFORMATION: May be fluoro uridine
<220> FEATURE:

<221> NAME/KEY: MOD_RES
<222> LOCATION: (16)..(16)
<223> OTHER INFORMATION: May be fluoro uridine
<220> FEATURE:
<221> NAME/KEY: MOD_RES
<222> LOCATION: (17)..(17)
<223> OTHER INFORMATION: May be fluoro cytidine
<220> FEATURE:
<221> NAME/KEY: MOD_RES
<222> LOCATION: (20)..(20)
<223> OTHER INFORMATION: May be fluoro uridine
<220> FEATURE:
<221> NAME/KEY: MOD_RES
<222> LOCATION: (22)..(22)
<223> OTHER INFORMATION: May be fluoro uridine
<220> FEATURE:
<221> NAME/KEY: MOD_RES
<222> LOCATION: (23)..(23)
<223> OTHER INFORMATION: May be fluoro uridine

<400> SEQUENCE: 34
uagcaccauu ugaaaucagu guu 23

<210> SEQ ID NO 35
<211> LENGTH: 24
<212> TYPE: RNA
<213> ORGANISM: Artificial Sequence
<220> FEATURE:
<223> OTHER INFORMATION: miR-29c mimic first-antisense-guide strand
<220> FEATURE:
<221> NAME/KEY: MOD_RES
<222> LOCATION: (1)..(1)
<223> OTHER INFORMATION: May be fluoro uridine
<220> FEATURE:
<221> NAME/KEY: MOD_RES
<222> LOCATION: (4)..(4)
<223> OTHER INFORMATION: May be fluoro cytidine
<220> FEATURE:
<221> NAME/KEY: MOD_RES
<222> LOCATION: (6)..(6)
<223> OTHER INFORMATION: May be fluoro cytidine
<220> FEATURE:
<221> NAME/KEY: MOD_RES
<222> LOCATION: (7)..(7)
<223> OTHER INFORMATION: May be fluoro cytidine
<220> FEATURE:
<221> NAME/KEY: MOD_RES
<222> LOCATION: (9)..(9)
<223> OTHER INFORMATION: May be fluoro uridine
<220> FEATURE:
<221> NAME/KEY: MOD_RES
<222> LOCATION: (10)..(10)
<223> OTHER INFORMATION: May be fluoro uridine
<220> FEATURE:
<221> NAME/KEY: MOD_RES
<222> LOCATION: (11)..(11)
<223> OTHER INFORMATION: May be fluoro uridine
<220> FEATURE:
<221> NAME/KEY: MOD_RES
<222> LOCATION: (16)..(16)
<223> OTHER INFORMATION: May be fluoro uridine
<220> FEATURE:
<221> NAME/KEY: MOD_RES
<222> LOCATION: (17)..(17)
<223> OTHER INFORMATION: May be fluoro cytidine
<220> FEATURE:
<221> NAME/KEY: MOD_RES
<222> LOCATION: (20)..(20)
<223> OTHER INFORMATION: May be fluoro uridine
<220> FEATURE:
<221> NAME/KEY: MOD_RES
<222> LOCATION: (21)..(21)
<223> OTHER INFORMATION: May be fluoro uridine
<220> FEATURE:
<221> NAME/KEY: MISC_FEATURE
<222> LOCATION: (22)..(24)
<223> OTHER INFORMATION: May be joined through phosphorothioate bonds

<400> SEQUENCE: 35
uagcaccauu ugaaaucggu uauu 24

<210> SEQ ID NO 36
<211> LENGTH: 16
<212> TYPE: DNA
<213> ORGANISM: Artificial Sequence
<220> FEATURE:
<223> OTHER INFORMATION: antimiR-29
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(1)
<223> OTHER INFORMATION: May be locked nucleic acid deoxyguanosine
<220> FEATURE:
<221> NAME/KEY: MOD_RES
<222> LOCATION: (5)..(5)
<223> OTHER INFORMATION: May be locked nucleic acid deoxythymidine
<220> FEATURE:
<221> NAME/KEY: MOD_RES
<222> LOCATION: (6)..(6)
<223> OTHER INFORMATION: May be locked nucleic acid deoxycytidine
<220> FEATURE:
<221> NAME/KEY: MOD_RES
<222> LOCATION: (8)..(8)
<223> OTHER INFORMATION: May be locked nucleic acid deoxyadenosine
<220> FEATURE:
<221> NAME/KEY: MOD_RES
<222> LOCATION: (10)..(10)
<223> OTHER INFORMATION: May be locked nucleic acid deoxythymidine
<220> FEATURE:
<221> NAME/KEY: MOD_RES
<222> LOCATION: (11)..(11)
<223> OTHER INFORMATION: May be locked nucleic acid deoxyguanosine
<220> FEATURE:
<221> NAME/KEY: MOD_RES
<222> LOCATION: (13)..(13)
<223> OTHER INFORMATION: May be locked nucleic acid deoxythymidine
<220> FEATURE:
<221> NAME/KEY: MOD_RES
<222> LOCATION: (15)..(15)
<223> OTHER INFORMATION: May be locked nucleic acid deoxycytidine
<220> FEATURE:
<221> NAME/KEY: MOD_RES
<222> LOCATION: (16)..(16)
<223> OTHER INFORMATION: May be locked nucleic acid deoxythymidine

<400> SEQUENCE: 36
gatttcaaat ggtgct 16

<210> SEQ ID NO 37
<211> LENGTH: 22
<212> TYPE: RNA
<213> ORGANISM: Artificial Sequence
<220> FEATURE:
<223> OTHER INFORMATION: miR-29a mimic second-sense-passenger strand
<220> FEATURE:
<221> NAME/KEY: MOD_RES
<222> LOCATION: (1)..(1)
<223> OTHER INFORMATION: May be O-methyl uridine
<220> FEATURE:
<221> NAME/KEY: MOD_RES
<222> LOCATION: (2)..(2)
<223> OTHER INFORMATION: May be O-methyl adenosine

<400> SEQUENCE: 37
uaaccgauuu cagauggugc ua 22

<210> SEQ ID NO 38

```
<211> LENGTH: 24
<212> TYPE: RNA
<213> ORGANISM: Artificial Sequence
<220> FEATURE:
<223> OTHER INFORMATION: miR-29a mimic first-antisense-guide strand

<400> SEQUENCE: 38

uagcaccauc ugaaaucggu uauu                                          24


<210> SEQ ID NO 39
<211> LENGTH: 23
<212> TYPE: RNA
<213> ORGANISM: Artificial Sequence
<220> FEATURE:
<223> OTHER INFORMATION: miR-29b mimic second-sense-passenger strand
<220> FEATURE:
<221> NAME/KEY: MOD_RES
<222> LOCATION: (1)..(1)
<223> OTHER INFORMATION: May be O-methyl adenosine
<220> FEATURE:
<221> NAME/KEY: MOD_RES
<222> LOCATION: (2)..(2)
<223> OTHER INFORMATION: May be O-methyl adenosine

<400> SEQUENCE: 39

aacacugauu ucaaauggug cua                                           23


<210> SEQ ID NO 40
<211> LENGTH: 25
<212> TYPE: RNA
<213> ORGANISM: Artificial Sequence
<220> FEATURE:
<223> OTHER INFORMATION: miR-29b mimic first-antisense-guide strand

<400> SEQUENCE: 40

uagcaccauu ugaaaucagu guuuu                                         25


<210> SEQ ID NO 41
<211> LENGTH: 22
<212> TYPE: RNA
<213> ORGANISM: Artificial Sequence
<220> FEATURE:
<223> OTHER INFORMATION: miR-29c mimic second-sense-passenger strand
<220> FEATURE:
<221> NAME/KEY: MOD_RES
<222> LOCATION: (1)..(1)
<223> OTHER INFORMATION: May be O-methyl uridine
<220> FEATURE:
<221> NAME/KEY: MOD_RES
<222> LOCATION: (2)..(2)
<223> OTHER INFORMATION: May be O-methyl adenosine

<400> SEQUENCE: 41

uaaccgauuu caaauggugc ua                                            22


<210> SEQ ID NO 42
<211> LENGTH: 24
<212> TYPE: RNA
<213> ORGANISM: Artificial Sequence
<220> FEATURE:
<223> OTHER INFORMATION: miR-29c mimic first-antisense-guide strand

<400> SEQUENCE: 42

uagcaccauu ugaaaucggu uauu                                          24
```

MIR-29 MIMICS AND USES THEREOF

CROSS REFERENCE TO RELATED APPLICATIONS

The present Application claims the benefit of priority to U.S. Provisional Application No. 62/047,562, filed on Sep. 8, 2014, the contents of which are hereby incorporated by reference in their entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: MIRG_047_01US_SeqList_ST25.txt, date recorded: Oct. 13, 2015, file size 41 kilobytes).

FIELD OF THE INVENTION

The present invention relates to synthetic miRNA mimics or promiRs that increase miRNA activity in vivo. In particular, the present invention relates to mimics of miR-29 and their use in reducing collagen deposition and associated conditions, such as fibrosis.

BACKGROUND OF THE INVENTION

Based on gain- or loss-of-function data collected in animal disease models using genetics or pharmacological modulation of microRNAs (miRNAs), it is now well accepted that miRNAs are important players during disease. These studies, combined with recent positive clinical efficacy data (Janssen et al, 2013), underscore the relevance of miRNAs and the viability for miRNAs to become the next class of therapeutics. Indeed, miRNAs have several advantages as therapeutic intervention points in that they are small and comprise a known sequence. Additionally, since a single miRNA can regulate numerous target mRNAs within biological pathways, modulation of a miRNA in principle allows for influencing an entire gene network and modifying complex disease phenotypes (van Rooij & Olson, 2012).

While many studies have shown therapeutic efficacy using single-stranded miRNA inhibitors called antimiRs, efforts to restore or increase the function of a miRNA have been lagging behind (van Rooij et al, 2012). Currently, miRNA function can be increased either by viral overexpression or by using synthetic double-stranded miRNAs. So far the use of adeno-associated viruses (AAV) to drive expression of a given miRNA for restoring its activity in vivo has shown to be effective in a mouse model of hepatocellular and lung carcinoma (Kasinski & Slack, 2012; Kola et al, 2009) and spinal and bulbar muscular atrophy (Miyazaki et al, 2012), while the use of unformulated synthetic oligonucleotide-based approaches to increase miRNA levels has not been well explored.

The microRNA-29 (miR-29) family is well characterized for their ability to regulate extracellular matrix proteins (He et al, 2013). The family consists of miR-29a, -29b and -29c, which are expressed as two bicistronic clusters (miR-29a/-29b-1 and miR-29b-2/-29c), and are largely homologous in sequence with only a few mismatches between the different members in the 3' regions of the mature miRNA (van Rooij et al, 2008). All three members are reduced in different types of tissue fibrosis and therapeutic benefit of increasing miR-29 levels has been shown for heart (van Rooij et al, 2008), kidney (Qin el al, 2011; Wang et al, 2012; Xiao et al, 2012), liver (Roderburg et al, 2011; Sekiya et al, 2011; Zhang et al, 2012), lung (Cushing et al, 2011; Xiao et al, 2012) and systemic sclerosis (Maurer et al, 2010).

There is a need in the art for synthetic oligonucleotide mimics of miR-29 that can effectively increase miR-29 activity in vivo. Such miR-29 mimics or miR-29 promiRs are useful for treating various tissue fibrotic conditions.

SUMMARY OF THE INVENTION

The present invention is based, in part, on the discovery that miRNA mimics with modifications for stability and cellular uptake can be used to replicate endogenous functions of miR-29. For instance, therapeutic treatment with a miR-29b mimic in the setting of pulmonary fibrosis restores the bleomycin-induced reduction of miR-29 and blocks and reverses pulmonary fibrosis, which coincides with a repression of miR-29 target genes that are induced during the disease process. Similarly, treatment of skin incisions with a miR-29b mimic down-regulates the expression of extracellular matrix genes and other genes involved in the fibrotic process. Accordingly, the present invention provides double-stranded RNA miR-29 mimetic compounds.

In some embodiments, the miR-29 mimetic compound comprises (a) a first strand of about 23 to about 26 ribonucleotides comprising a mature miR-29a, miR-29b, or miR-29c sequence; and (b) a second strand of about 22 to about 23 ribonucleotides comprising a sequence that is substantially complementary to the first strand, wherein the first strand has a 3' nucleotide overhang relative to the second strand. In certain embodiments, the first strand and second strand contain one or more modified nucleotides. The modified nucleotides may be 2' sugar modifications, such as 2'-alkyl (2'-O-methyl) or 2'-fluoro modifications. In one embodiment, the first strand has one or more 2'-fluoro modifications. In another embodiment, the second strand has one or more 2'-O-methyl modifications. In some embodiments, the second strand has one, two, three, or more mismatches relative to the first strand. In one embodiment, the second strand of a miR-29 mimetic compound contains mismatches at positions 4, 13, and/or 16 from the 3' end (of the second strand) relative to the first strand.

In one embodiment, the second strand of the miR-29 mimetic compound is linked to a cholesterol molecule at its 3' terminus. In certain embodiments, the cholesterol molecule is linked to the second strand through at least a six carbon linker. The linker may be a cleavable linker.

In one embodiment, the nucleotides comprising the 3' overhang in the first strand are linked by phosphorothioate linkages.

In one embodiment, the miR-29 mimetic compound comprises a first strand comprising the sequence of SEQ ID NO: 27 and a second strand comprising the sequence of SEQ ID NO: 5.

In another embodiment, the miR-29 mimetic compound comprises a first strand comprising the sequence of SEQ ID NO: 19 and a second strand comprising the sequence of SEQ ID NO: 1.

In yet another embodiment, the miR-29 mimetic compound comprises a first strand comprising the sequence of SEQ ID NO: 19 and a second strand comprising the sequence of SEQ ID NO: 15.

In yet another embodiment, the miR-29 mimetic compound comprises a first strand comprising the sequence of SEQ ID NO: 33 and a second strand comprising the sequence of SEQ ID NO: 1.

In yet another embodiment, the miR-29 mimetic compound comprises a first strand comprising the sequence of SEQ ID NO: 34 and a second strand comprising the sequence of SEQ ID NO: 1.

In yet another embodiment, the miR-29 mimetic compound comprises a first strand comprising the sequence of SEQ ID NO: 35 and a second strand comprising the sequence of SEQ ID NO: 24.

The present invention provides a pharmaceutical composition comprising an effective amount of the miR-29 mimetic compounds described herein or a pharmaceutically-acceptable salt thereof, and a pharmaceutically-acceptable carrier or diluent. In certain embodiments, the pharmaceutical composition is formulated for pulmonary, nasal, intranasal or ocular delivery and can be in the form of powders, aqueous solutions, aqueous aerosols, nasal drops, aerosols, and/or ocular drops. In some embodiments, the pharmaceutical composition is administered with an inhalation system such as a nebulizer, a metered dose inhaler, a dry powder inhaler, or a soft mist inhaler.

The present invention also includes a method of regulating an extracellular matrix gene in a cell comprising contacting the cell with the miR-29 mimetic compounds described herein. In one embodiment, the expression or activity of the extracellular matrix gene is reduced following contact with the miR-29 mimetic compound or composition. In some embodiments, the extracellular matrix gene is a collagen gene, such as Col1a1 and Col3a1. The cell may be in vitro, in vivo, or ex vivo.

The present invention provides a method of treating or preventing tissue fibrosis in a subject in need thereof. In one embodiment, the method comprises administering to the subject a miR-29 mimetic compound described herein. In certain embodiments, the tissue fibrosis is cardiac fibrosis, pulmonary fibrosis, renal fibrosis, hepatic fibrosis, ocular fibrosis, cutaneous fibrosis including hypertrophic scarring and keloids, hand, joint or tendon fibrosis, Peyronie's disease or scleroderma. In one embodiment, the tissue fibrosis is idiopathic pulmonary fibrosis (IPF).

In certain embodiments, the method for treating or preventing tissue fibrosis comprises administering a miR-29 mimetic compound or a composition described herein via the pulmonary, nasal, or intranasal route. In one embodiment, the miR-29 mimetic compound or the composition is delivered via inhalation.

The present invention also includes a method of regulating non-extracellular matrix genes in a cell comprising contacting the cell with the miR-29 mimetic compounds described herein. In one embodiment, the expression or activity of the non-extracellular matrix gene is increased following contact with the miR-29 mimetic compound or composition. In some embodiments, the non-extracellular matrix gene is a gene such as liga3 or Numb. The cell may be in vitro, in vivo, or ex vivo.

The present invention also provides a method for assessing the efficacy of a treatment with a miR-29 agonist or miR-29 antagonist, the method comprising determining a level of expression of one or more genes in cells or a fibrotic tissue of a subject prior to the treatment with the miR-29 agonist or miR-29 antagonist, wherein the one or more genes are selected from a set of genes modulated by miR-29; determining the level of expression of the same one or more genes in cells/fibrotic tissue of the subject after treatment with the miR-29 agonist or miR-29 antagonist; and determining the treatment to be effective, less effective, or not effective baaed on the expression levels prior to and after the treatment. In one embodiment, the one or more genes modulated by miR-29 are selected from Table 5.

Figure 13:
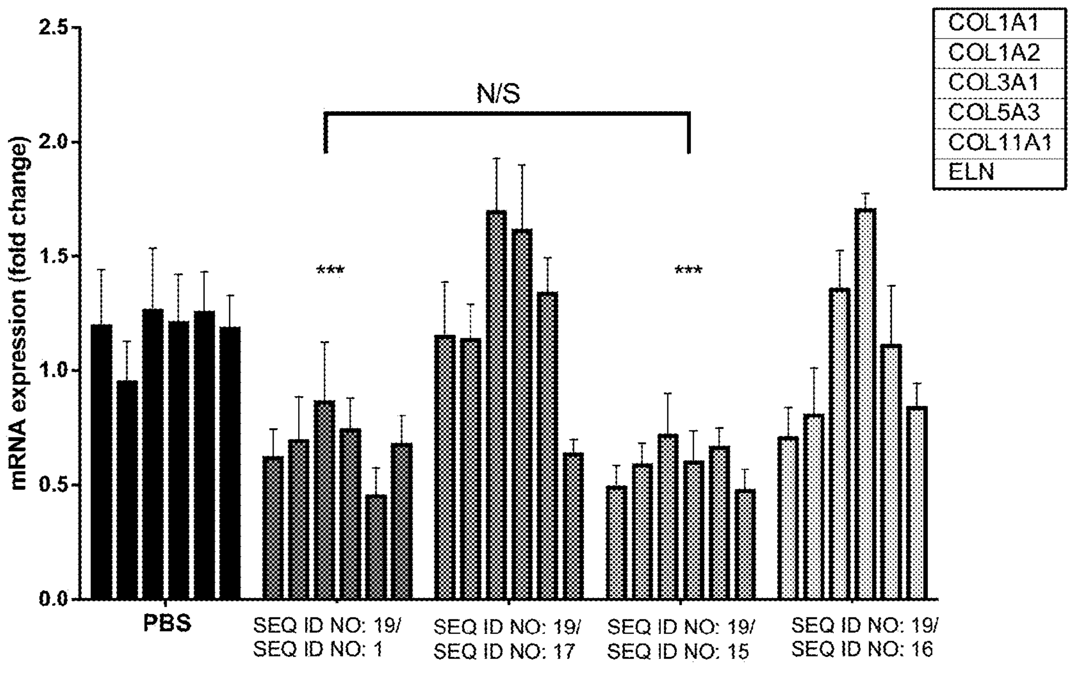

FIG. 13. In vivo activity of miR-29b mimics with linker modifications. Mice with incisional wounds were treated with 20 nmol of various miR-29b mimics that differ only in the linkage between the cholesterol moiety and the second/sense strand. Activity of the miR-29b mimics was determined by measuring the expression of five collagen synthesis genes.

Figure 14:
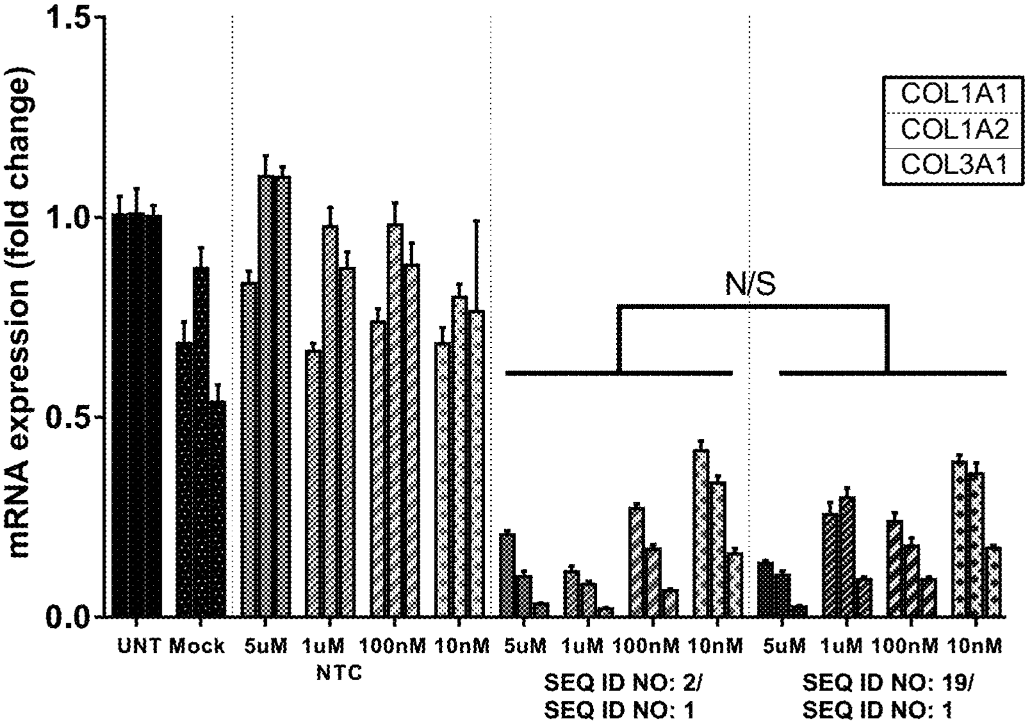

FIG. 14. Effect of 5' phosphorylation on the activity of miR-29b mimics. RAB-9 skin fibroblasts were transfected with varying concentrations of miR-29b mimics with (SEQ ID NO: 2/SEQ ID NO: 1) and without (SEQ ID NO: 19/SEQ ID NO: 1) 5' phosphorylation on the antisense strand. Activity of the miR-29b mimics was determined by measuring the expression of three collagen synthesis genes.

DETAILED DESCRIPTION OF THE INVENTION

Over the last decade great enthusiasm has evolved for microRNA (miRNA) therapeutics. Part of the excitement stems from the fact that a miRNA often regulates numerous related mRNAs. As such, modulation of a single miRNA allows for parallel regulation of multiple genes involved in a particular disease. While many studies have shown therapeutic efficacy using miRNA inhibitors, efforts to restore or increase the function of a miRNA have been lagging behind.

The miR-29 family has gained a lot of attention for its clear function in tissue fibrosis. This fibroblast-enriched miRNA family is downregulated in fibrotic diseases which induces a coordinate increase of many extracellular matrix genes. The present inventors have found that administration of synthetic RNA duplexes can increase miR-29 levels in vivo for several days. Moreover, therapeutic delivery of these miR-29 mimics during bleomycin-induced pulmonary fibrosis restores endogenous miR-29 function thereby decreasing collagen expression and blocking and reversing pulmonary fibrosis. Furthermore, administration of miR-29 mimics of the present invention to skin incisions downregulates extracellular matrix genes and other genes involved in the fibrotic process. These data support the feasibility of designing effective miRNA mimics to therapeutically increase miRNAs and indicate miR-29 to be a potent therapeutic miRNA for treating various fibrotic conditions and disorders involving increased collagen production. Accordingly, the present invention provides miR-29 mimics, compositions and uses thereof.

A microRNA mimetic compound according to the invention comprises a first strand and a second strand, wherein the first strand comprises a mature miR-29a, miR-29b, or miR-29c sequence and the second strand comprises a sequence that is substantially complementary to the first strand and has at least one modified nucleotide. Throughout the disclosure, the term "microRNA mimetic compound" may be used interchangeably with the terms "promiR-29," "miR-29 agonist," "microRNA agonist," "microRNA mimic," "miRNA mimic," or "miR-29 mimic;" the term "first strand" may be used interchangeably with the terms "antisense strand" or "guide strand"; the term "second strand" may be used interchangeably with the term "sense strand" or "passenger strand;" and the term "miR-29 antagonist" may be used interchangeably with the terms "oligonucleotide inhibitor," "antimiR-29," "antisense oligonucleotide," "miR-29 antagomir" or "anti-microRNA oligonucleotide."

In one embodiment, the first strand of the microRNA mimetic compound comprises from about 23 to about 26 nucleotides comprising a sequence of mature miR-29a, miR-29b, or miR-29c and the second strand comprises from about 22 to about 23 nucleotides comprising a sequence that is partially, substantially, or fully complementary to the first strand. In various embodiments, the first strand may comprise about 23, 24, 25, or 26 nucleotides and the second strand may comprise about 22 or 23 nucleotides.

The nucleotides that form the first and the second strand of the microRNA mimetic compounds may comprise ribonucleotides, deoxyribonucleotides, modified nucleotides, and combinations thereof. In certain embodiments, the first strand and the second strand of the microRNA mimetic compound comprise ribonucleotides and/or modified ribonucleotides. The term "modified nucleotide" means a nucleotide where the nucleobase and/or the sugar moiety is modified relative to unmodified nucleotides.

In certain embodiments, the microRNA mimetic compounds have a first strand or an antisense strand, whose sequence is identical to all or part of a mature miR-29a, miR-29b, or miR-29c sequence, and a second strand or a sense strand whose sequence is about 70% to about 100% complementary to the sequence of the first strand. In one embodiment, the first strand of the miRNA mimetic compound is at least about 75, 80, 85, 90, 95, or 100% identical, including all integers there between, to the entire sequence of a mature, naturally occurring miR-29a, miR-29b, or miR-29c sequence. In certain embodiments, the first strand is about or is at least about 90, 91, 92, 93, 94, 95, 96, 97, 98, 99, or 100% identical to the sequence of a mature, naturally-occurring miRNA, such as the mouse, human, or rat miR-29a, miR-29b, or miR-29c sequence. Alternatively, the first strand may comprise 20, 21, 22, or 23 nucleotide positions in common with a mature, naturally-occurring miRNA as compared by sequence alignment algorithms and methods well known in the art.

It is understood that the sequence of the first strand is considered to be identical to the sequence of a mature miR-29a, miR-29b, or miR-29c even if the first strand includes a modified nucleotide instead of a naturally-occurring nucleotide. For example, if a mature, naturally-occurring miRNA sequence comprises a cytidine nucleotide at a specific position, the first strand of the mimetic compound may comprise a modified cytidine nucleotide, such as 2'-fluoro-cytidine, at the corresponding position or if a mature, naturally-occurring miRNA sequence comprises a uridine nucleotide at a specific position, the miRNA region of the first strand of the mimetic compound may comprise a modified uridine nucleotide, such as 2'-fluoro-uridine, 2'-O-methyl-uridine, 5-fluorouracil, or 4-thiouracil at the corresponding position. Thus, as long as the modified nucleotide has the same base-pairing capability as the nucleotide present in the mature, naturally-occurring miRNA sequence, the sequence of the first strand is considered to be identical to the mature, naturally-occurring miRNA sequence. In some embodiments, the first strand may include a modification of the 5'-terminal residue. For example, the first strand may have a 5'-terminal monophosphate. In some other embodiments, the first strand does not contain a 5'-terminal monophosphate.

In some embodiments, the second strand of the microRNA mimic is partially complementary to the sequence of the first strand. For example, the sequence of the second strand is at least about 70%, 75%, 80%, 85%, 90%, 95%, 96%, 97%, 98%, or 99%, inclusive of all values therebetween, complementary to the sequence of the first strand. In some other embodiments, the second strand is substantially complementary to the sequence of the first strand. For example, the second strand is at least about 85%, 86%, 87%, 88%, 89%, 90%, 91%, 92%, 93%, 94%, 95%, 96%, 97%, 98%, or 99%, inclusive of all values therebetween, complementary to the sequence of the first strand. In yet some other embodiments, the sequence of the second strand may be fully complementary to the first strand. In certain embodiments, about 19, 20, 21, 22, or 23 nucleotides of the complementary region of the second strand may be complementary to the first strand.

It is understood that the sequence of the second strand is considered to be complementary to the first strand even if the second strand includes a modified nucleotide instead of a naturally-occurring nucleotide. For example, if the first strand sequence comprises a guanosine nucleotide at a specific position, the second strand may comprise a modified cytidine nucleotide, such as 2'-O-methyl-cytidine, at the corresponding position.

In some embodiments, the second strand comprises about 1, 2, 3, 4, 5, or 6 mismatches relative to the first strand. That is, up to 1, 2, 3, 4, 5, or 6 nucleotides between the first strand and the second strand may not be complementary. In one embodiment, the mismatches are not consecutive and are distributed throughout the second strand. In another embodiment, the mismatches are consecutive and may create a bulge. In one embodiment, the second strand contains 3 mismatches relative to the first strand. In certain embodiments, the second strand of a miR-29a mimic or a miR-29c mimic contains mismatches at positions 4, 13, and/or 16 from the 3' end (of the second strand) relative to the first strand. In one embodiment, the second strand of a miR-29b mimic contains mismatches at positions 4, 13, and/or 16 from the 3' end (of the second strand) relative to the first strand. In another embodiment, the second strand of a miR-29b mimic contains mismatches at positions 4, 9, 10, 11, 13 and/or 16 from the 3' end (of the second strand) relative to the first strand.

In some embodiments, the first and/or the second strand of the mimetic compound may comprise an overhang on the 5' or 3' end of the strands. In certain embodiments, the first strand comprises a 3' overhang, i.e., a single-stranded region that extends beyond the duplex region, relative to the second strand. The 3' overhang of the first strand may range from about one nucleotide to about four nucleotides. In certain embodiments, the 3' overhang of the first strand may comprise 1 or 2 nucleotides. In some embodiments, the nucleotides comprising the 3' overhang in the first strand are linked by phosphorothioate linkages. The nucleotides comprising the 3' overhang in the first strand may include ribonucleotides, deoxyribonucleotides, modified nucleotides, or combinations thereof. In certain embodiments, the 3' overhang in the first strand comprises two ribonucleotides. In one embodiment, the 3' overhang of the first strand comprises two uridine nucleotides linked through a phosphorothioate linkage. In some embodiments, the first strand may not contain an overhang.

In one embodiment, the nucleotides in the second/sense strand of miR-29 mimics of the invention are linked by phosphodiester linkages and the nucleotides in the first/antisense strand are linked by phosphodiester linkages except for the last three nucleotides at the 3' end which are linked to each other via phosphorothioate linkages.

In various embodiments, miR-29 mimics of the present invention comprise modified nucleotides. For instance, in one embodiment, the first strand of the mimic comprises one or more 2'-fluoro nucleotides. In another embodiment, the first strand may not include any modified nucleotide. In one embodiment, the second strand comprises one or more 2'-O-methyl modified nucleotides.

In various embodiments, miR-29 mimics according to the present invention comprise first and second strands listed in the Tables below. Definitions of the modifications are presented in Table 4. These miR-29 mimetic compounds are useful for regulating the expression of extracellular matrix genes in a cell and treating associated conditions, such as tissue fibrosis, dermal fibrosis, including the uses and conditions described in WO 2009/018493, which is hereby incorporated by reference in its entirety.

TABLE 1 miR-29a mimics

| Modified Sequence | SEQ ID NO. |
|---|---|
| **Second/sense/passenger strands** | |
| 5'-mU.mA.rA.rC.rC.rG.rA.rU.rU.rU.rC.rA.rG.rA.rU.rG.rG.rU.rG.rC.rU.rA.rU.rU-3' | 3 |
| 5'-mU.mA.rA.mC.mC.rG.mU.mU.mU.rA.mC.rA.rG.rA.mU.rG.rG.mU.mC.mC.mU.rA-3' | 4 |
| 5'-mU.mA.rA.mC.mC.rG.mU.mU.mU.rA.mC.rA.rG.rA.mU.rG.rG.mU.mC.mC.mU.rA.chol6-3' | 5 |
| 5'-mU.mA.rA.rC.rC.rG.rA.rU.rU.rU.rC.rA.rG.rA.rU.rG.rG.rU.rG.rC.rU.rAs.rUs.rUs.chol6-3' | 11 |
| 5'-mU.mA.rA.rC.rC.rG.rA.rU.rU.rU.rC.rA.rG.rA.rU.rG.rG.rU.rG.rC.rU.rA-3' | 37 |
| **First/antisense/guide strands** | |
| 5'-p.rU.rA.rG.rC.rA.rC.rC.rA.rU.rC.rU.rG.rA.rA.rA.rU.rC.rG.rG.rU.rU.rA.rU.rU-3' | 6 |
| 5'-p.fU.rA.rG.fC.rA.fC.fC.rA.fU.fC.fU.rG.rA.rA.rA.fU.fC.rG.rG.fU.fU.rAs.rUs.rU-3' | 7 |
| 5'-fU.rA.rG.fC.rA.fC.fC.rA.fU.fC.fU.rG.rA.rA.rA.fU.fC.rG.rG.fU.fU.rAs.rUs.rU-3' | 27 |
| 5'-rU.rA.rG.rC.rA.rC.rC.rA.rU.rC.rU.rG.rA.rA.rA.rU.rC.rG.rG.rU.rU.rA.rU.rU-3' | 38 |

TABLE 2 miR-29b mimics

| Modified Sequence | SEQ ID NO. |
|---|---|
| **Second/sense/passenger strands** | |
| 5'-mA.mA.rC.rA.rC.rU.rG.rA.rU.rU.rU.rC.rA.rA.rA.rU.rG.rG.rU.rG.rC.rU.rA.rU.rU-3' | 8 |
| 5'-mA.mA.mC.rA.mC.mU.rG.rA.mU.mU.mU.mC.rA.rA.rA.mU.rG.rG.mU.rG.mC.mU.rA.chol6-3' | 9 |
| 5'-mA.mA.rC.rA.rC.rU.rG.rA.rU.rU.rU.rC.rA.rA.rA.rU.rG.rG.rU.rG.rC.rU.rAs.rUs.rUs.chol6-3' | 10 |
| 5'-mA.mA.mC.rA.mC.mU.rG.mU.mU.mU.rA.mC.rG.rG.rG.mU.rG.rG.mU.mC.mC.mU.rA-3' | 13 |
| 5'-mA.mA.mC.rA.mC.mU.rG.mU.mU.mU.rA.mC.rG.rG.rG.mU.rG.rG.mU.mC.mC.mU.rA.chol6-3' | 14 |
| 5'-mA.mA.mC.rA.mC.mU.rG.mU.mU.mU.rA.mC.rA.rA.rA.mU.rG.rG.mU.mC.mC.mU.rA.chol6-3' | 1 |

TABLE 2-continued

| miR-29b mimics | |
|---|---|
| Modified Sequence | SEQ ID NO. |
| 5'-mA.mA.mC.rA.mC.mU.rG.mU.mU.mU.rA.mC.rA.rA.rA.mU.rG.rG.mU.mC.mC.mU.rA.dT.dT.chol6-3' | 15 |
| 5'-C6Chol.dT.dT.mA.mA.mC.rA.mC.mU.rG.mU.mU.mU.rA.mC.rA.rA.rA.mU.rG.rG.mU.mC.mC.mU.rA-3' | 16 |
| 5'mA.mA.mC.rA.mC.mU.rG.mU.mU.mU.rA.mC.rA.rA.rA.mU.rG.rG.mU.mC.mC.mU.rA.chol9-3' | 17 |
| 5'rA.mA.rC.mA.rC.mU.rG.mA.rU.mU.rU.mC.rA.mA.rA.mU.rG.mG.rU.mG.rC.mU.rA.chol6-3' | 28 |
| 5'rA.mA.rC.mA.rC.mU.rG.mA.rU.mU.rU.mC.rA.mA.rA.mU.rG.mG.rU.mG.rC.mU.rAs.rUs.rU.chol6-3' | 29 |
| 5'mA.mA.mC.rA.mC.mU.rG.mU.mU.mU.rA.mC.rA.rA.rA.mU.rG.rG.mU.mC.mC.mU.rA.cholTEG-3' | 30 |
| 5'-mA.mA.rC.rA.rC.rU.rG.rA.rU.rU.rU.rC.rA.rA.rA.rU.rG.rG.rU.rG.rC.rU.rA-3' | 39 |
| First/antisense/guide strands | |
| 5'-p.rU.rA.rG.rC.rA.rC.rC.rA.rU.rU.rU.rG.rA.rA.rA.rU.rC.rA.rG.rU.rG.rU.rU.rU.rU-3' | 18 |
| 5'-pfU.rA.rG.fC.rA.fC.fC.rA.fU.fU.fU.rG.rA.rA.rA.fU.fC.rA.rG.fU.rG.fU.fUs.rUs.rU-3' | 2 |
| 5'-fU.rA.rG.fC.rA.fC.fC.rA.fU.fU.fU.rG.rA.rA.rA.fU.fC.rA.rG.fU.rG.fU.fUs.rUs.rU-3' | 19 |
| 5'-pfU.rA.rG.fC.rA.fC.fC.rA.fC.fC.fC.rG.rA.rA.rA.fU.fC.rA.rG.fU.rG.fU.fUs.rUs.rU-3' | 20 |
| 5'-rU.rA.rG.rC.rA.rC.rC.rA.rU.rU.rU.rG.rA.rA.rA.rU.rC.rA.rG.rU.rG.rU.rU.rU.rU-3' | 21 |
| 5'-mU.rA.mG.rC.mA.rC.mC.rA.mU.rU.mU.rG.mA.rA.mA.rU.mC.rA.mG.rU.mG.rU.mU-3' | 31 |
| 5'-mU.rA.mG.rC.mA.rC.mC.rA.mU.rU.mU.rG.mA.rA.mA.rU.mC.rA.mG.rU.mG.rU.mUs.rUs.rU-3' | 32 |
| 5'-mU.rA.rG.mC.rA.mC.mC.rA.mU.mU.mU.rG.rA.rA.rA.mU.mC.rA.rG.mU.rG.mU.mUs.rUs.rU-3' | 33 |
| 5'-fU.rA.rG.fC.rA.fC.fC.rA.fU.fU.fU.rG.rA.rA.rA.fU.fC.rA.rG.fU.rG.fU.fU-3' | 34 |
| 5'-rU.rA.rG.rC.rA.rC.rC.rA.rU.rU.rU.rG.rA.rA.rA.rU.rC.rA.rG.rU.rG.rU.rU.rU.rU-3' | 40 |

TABLE 3

| miR-29c mimics | |
|---|---|
| Modified Sequence | SEQ ID NO. |
| Second/sense/passenger strands | |
| 5'-mU.mA.rA.rC.rC.rG.rA.rU.rU.rU.rC.rA.rA.rA.rU.rG.rG.rU.rG.rC.rU.rA.rU.rU-3' | 22 |
| 5'-mU.mA.rA.mC.mC.rG.mU.mU.mU.rA.mC.rA.rA.rA.mU.rG.rG.mU.mC.mC.mU.rA-3' | 23 |

TABLE 3-continued

| miR-29c mimics | |
|---|---|
| Modified Sequence | SEQ ID NO. |
| 5'-mU.mA.rA.mC.mC.rG.mU.mU.mU.rA.mC.rA.rA.rA.mU.rG.rG.mU.mC.mC.mU.rA.chol6-3' | 24 |
| 5'-mU.mA.rA.rC.rC.rG.rA.rU.rU.rU.rC.rA.rA.rA.rU.rG.rG.rU.rG.rC.rU.rAs.rUs.rUs.chol6-3' | 12 |
| 5'-mU.mA.rA.rC.rC.rG.rA.rU.rU.rU.rC.rA.rA.rA.rU.rG.rG.rU.rg.rC.rU.rA-3' | 41 |
| First/antisense/guide strands | |
| 5'-p.rU.rA.rG.rC.rA.rC.rC.rA.rU.rU.rU.rG.rA.rA.rA.rU.rC.rG.rG.rU.rU.rA.rU.rU-3' | 25 |
| 5'-p.fU.rA.rG.fC.rA.fC.fC.rA.fU.fU.fU.rG.rA.rA.rA.fU.fC.rG.rG.fU.fU.rAs.rUs.rU-3' | 26 |
| 5'-fU.rA.rG.fC.rA.fC.fC.rA.fU.fU.fU.rG.rA.rA.rA.fU.fC.rG.rG.fU.fU.rAs.rUs.rU-3' | 35 |
| 5'-rU.rA.rG.rC.rA.rC.rC.rA.rU.rU.rU.rG.rA.rA.rA.rU.rC.rG.rG.rU.rU.rA.rU.rU-3' | 42 |

TABLE 4

Definitions of Abbreviations

| Nucleotide unit or modification | Abbreviation | Nucleotide unit or modification | Abbreviation |
|---|---|---|---|
| ribo A | rA | ribo A P=S | rAs |
| ribo G | rG | ribo G P=S | rGs |
| ribo C | rC | ribo C P=S | rCs |
| ribo U | rU | ribo U P=S | rUs |
| O-methyl A | mA | O-methyl A P=S | mAs |
| O-methyl G | mG | O-methyl G P=S | mGs |
| O-methyl C | mC | O-methyl C P=S | mCs |
| O-methyl U | mU | O-methyl U P=S | mUs |
| fluoro C | fC | fluoro C P=S | fCs |
| fluoro U | fU | fluoro U P=S | fUs |
| deoxy A | dA | deoxy A P=S | dAs |
| deoxy G | dG | deoxy G P=S | dGs |
| deoxy C | dC | deoxy C P=S | dCs |
| deoxy T | dT | deoxy T P=S | dTs |
| monophosphate | P | | |
| Cholesterol conjugate with a 6 carbon linker | Chol6/C6 chol | | |
| Cholesterol conjugate with a 9 carbon linker | Chol9 | | |

In certain embodiments, a miR-29a mimic comprises a first strand comprising SEQ ID NO: 27 and a second strand comprising SEQ ID NO: 5. In other embodiments, a miR-29a mimic comprises a first strand comprising SEQ ID NO: 7 and a second strand comprising SEQ ID NO: 5.

In some embodiments, a miR-29b mimic comprises a first strand comprising SEQ ID NO: 19 and a second strand comprising SEQ ID NO: 1. In some other embodiments, a miR-29b mimic comprises a first strand comprising SEQ ID NO: 2 and a second strand comprising SEQ ID NO: 1. In yet some other embodiments, a miR-29b mimic comprises a first strand comprising SEQ ID NO: 19 and a second strand comprising SEQ ID NO: 15. In yet some other embodiments, a miR-29b mimic comprises a first strand comprising SEQ ID NO: 33 and a second strand comprising SEQ ID NO: 1. In yet some other embodiments, a miR-29b mimic comprises a first strand comprising SEQ ID NO: 34 and a second strand comprising SEQ ID NO: 1. In yet some other embodiments, a miR-29b mimic comprises a first strand comprising SEQ ID NO: 19 and a second strand comprising SEQ ID NO: 30.

In certain embodiments, a miR-29c mimic comprises a first strand comprising SEQ ID NO: 35 and a second strand comprising SEQ ID NO: 24. In other embodiments, a miR-29c mimic comprises a first strand comprising SEQ ID NO: 26 and a second strand comprising SEQ ID NO: 24.

The modified nucleotides that may be used in the microRNA mimetic compounds of the invention can include nucleotides with a base modification or substitution. The natural or unmodified bases in RNA are the purine bases adenine (A) and guanine (G), and the pyrimidine bases cytosine (C) and uracil (U) (DNA has thymine (T)). In contrast, modified bases, also referred to as heterocyclic base moieties, include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo (including 5-bromo, 5-trifluoromethyl and other 5-substituted uracils and cytosines), 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

In some embodiments, the microRNA mimetic compounds can have nucleotides with modified sugar moieties. Representative modified sugars include carbocyclic or acyclic sugars, sugars having substituent groups at one or more of their 2', 3' or 4' positions and sugars having substituents in place of one or more hydrogen atoms of the sugar. In certain embodiments, the sugar is modified by having a substituent group at the 2' position. In additional embodiments, the sugar is modified by having a substituent group at the 3' position. In other embodiments, the sugar is modified by having a substituent group at the 4' position. It is also contemplated that a sugar may have a modification at more than one of those positions, or that an RNA molecule may have one or more nucleotides with a sugar modification at one position and also one or more nucleotides with a sugar modification at a different position.

Sugar modifications contemplated in the miRNA mimetic compounds include, but are not limited to, a substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl.

In some embodiments, miRNA mimetic compounds have a sugar substituent group selected from the following: $C_1$ to $C_{10}$ lower alkyl, substituted lower alkyl, alkenyl, alkynyl, alkaryl, aralkyl, O-alkaryl or O-aralkyl, SH, $SCH_3$, Cl, Br, CN, OCN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, or similar substituents. In one embodiment, the modification includes 2'-methoxyethoxy (2'-O—$CH_2CH_2OCH_3$, which is also known as 2'-O-(2-methoxyethyl) or 2'-MOE), that is, an alkoxyalkoxy group. Another modification includes 2'-dimethylaminooxyethoxy, that is, a $O(CH_2)_2ON(CH_3)_2$ group, also known as 2'-DMAOE and 2'-dimethylaminoethoxyethoxy (also known in the art as 2'-O-dimethyl-amino-ethoxy-ethyl or 2'-DMAEOE), that is, 2'-O—$CH_2$—O—$CH_2$—$N(CH_3)_2$.

Sugar substituent groups on the 2' position (2'-) may be in the arabino (up) position or ribo (down) position. One 2'-arabino modification is 2'-F. Other similar modifications may also be made at other positions on the sugar moiety, particularly the 3' position of the sugar on the 3' terminal nucleoside or in 2'-5' linked oligonucleotides and the 5' position of 5' terminal nucleotide.

In certain embodiments, the sugar modification is a 2'-O-alkyl (e.g. 2'-O-methyl, 2'-O-methoxyethyl), 2'-halo (e.g., 2'-fluoro, 2'-chloro, 2'-bromo), and 4' thio modifications. For instance, in some embodiments, the first strand of the miR-29a, miR-29b, or miR-29c mimetic compound comprises one or more 2' fluoro nucleotides. In another embodiment, the first strand of the mimetic compounds has no modified nucleotides. In yet another embodiment, the second strand of miR-29a, miR-29b, or miR-29c mimetic compound comprises one or more 2'-O-methyl modified nucleotides.

The first and the second strand of microRNA mimetic compounds of the invention can also include backbone modifications, such as one or more phosphorothioate, morpholino, or phosphonocarboxylate linkages (see, for example, U.S. Pat. Nos. 6,693,187 and 7,067,641, which are herein incorporated by reference in their entireties). For example, in some embodiments, the nucleotides comprising the 3' overhang in the first strand are linked by phosphorothioate linkages.

In some embodiments, the microRNA mimetic compounds are conjugated to a carrier molecule such as a steroid (cholesterol), a vitamin, a fatty acid, a carbohydrate or glycoside, a peptide, or other small molecule ligand to facilitate in vivo delivery and stability. Preferably, the carrier molecule is attached to the second strand of the microRNA mimetic compound at its 3' or 5' end through a linker or a spacer group. In various embodiments, the carrier molecule is cholesterol, a cholesterol derivative, cholic acid or a cholic acid derivative. The use of carrier molecules disclosed in U.S. Pat. No. 7,202,227, which is incorporated by reference herein in its entirety, is also envisioned. In certain embodiments, the carrier molecule is cholesterol and it is attached to the 3' or 5' end of the second strand through at least a six carbon linker. In one embodiment, the carrier molecule is attached to the 3' end of the second strand through a six or nine carbon linker. In some embodiments, the linker is a cleavable linker. In various embodiments, the linker comprises a substantially linear hydrocarbon moiety. The hydrocarbon moiety may comprise from about 3 to about 15 carbon atoms and may be conjugated to cholesterol through a relatively non-polar group such as an ether or a thioether linkage. In certain embodiments, the hydrocarbon linker/spacer comprises an optionally substituted C2 to C15 saturated or unsaturated hydrocarbon chain (e.g. alkylene or alkenylene). A variety of linker/spacer groups described in U.S. Pre-grant Publication No. 2012/0128761, which is incorporated by reference herein in its entirety, can be used in the present invention.

In various embodiments, the present invention provides methods of treating, ameliorating, or preventing fibrotic conditions in a subject in need thereof comprising administering to the subject a therapeutically effective amount of at least one of a miR-29a, miR-29b, and/or miR-29c mimic described herein. Fibrotic conditions that may be treated using miR-29 mimics of the invention include, but are not limited to, tissue fibrosis such as pulmonary fibrosis, cardiac fibrosis, hepatic fibrosis, kidney fibrosis, diabetic fibrosis, skeletal muscle fibrosis, and ocular fibrosis; and dermal/cutaneous fibrosis such as keloids, cutaneous sclerosis, systemic sclerosis (scleroderma), hypertrophic scars, hand/joint/tendon fibrosis, and Peyronie's disease. In one embodiment, the fibrotic condition treated using the miR-29 mimics of the invention is idiopathic pulmonary fibrosis. Use of miR-29 agonists in treating certain fibrotic conditions is described in U.S. Pat. No. 8,440,636, which is hereby incorporated by reference herein.

In one embodiment, administration of miR-29 mimics of the present invention reduces the expression or activity one or more extracellular matrix genes in cells of the subject. In another embodiment, administration of miR-29 mimics of the present invention reduces the expression or activity one or more collagen synthesis genes in cells of the subject. In yet another embodiment, administration of miR-29 mimics up-regulates the expression or activity one or more genes involved in the skin development, epidermis development, ectoderm development and cellular homeostasis. Cells of the subject where the expression or activity of various genes is regulated by miR-29 mimics of the invention include fibroblasts and epidermal cells. In some embodiments, administration of miR-29 mimics down-regulates inflammatory responses associated with fibrosis. For example, administration of miR-29 mimics reduces the levels of pro-inflammatory cytokines such as IL-12, IL-4, GCSF, and TNF-$\alpha$ in fibrosis patients. Administration of miR-29 mimics may also reduce infiltration of immune effector cells such as neutrophils, lymphocytes, monocytes, and macrophages in fibrotic tissues or organs.

In certain embodiments, the present invention provides methods of regulating an extracellular matrix gene in a cell comprising contacting the cell with a miR-29 mimic of the present invention. In some embodiments, the invention provides methods of regulating a collagen synthesis gene in a cell comprising contacting the cell with a miR-29 mimic of the present invention. Upon treatment or contact, the miR-29 mimic reduces the expression or activity of the extracellular matrix gene or the collagen synthesis gene.

As used herein, the term "subject" or "patient" refers to any vertebrate including, without limitation, humans and other primates (e.g., chimpanzees and other apes and monkey species), farm animals (e.g., cattle, sheep, pigs, goats and horses), domestic mammals (e.g., dogs and cats), laboratory animals (e.g., rabbits, rodents such as mice, rats, and guinea pigs), and birds (e.g., domestic, wild and game birds such as chickens, turkeys and other gallinaceous birds, ducks, geese, and the like). In some embodiments, the subject is a mammal. In other embodiments, the subject is a human.

The invention also provides methods for assessing the efficacy of a treatment with miR-29 agonists (e.g. drugs or miR-29 mimics) or miR-29 antagonists (e.g. drugs or antimiR-29). For instance, in one embodiment, the method for assessing the treatment efficacy comprises determining a level of expression of one or more genes in cells or a fibrotic tissue of a subject prior to the treatment with miR-29 mimics or miR-29 antagonists, wherein the one or more genes are selected from a set of genes modulated by miR-29, e.g. genes listed in Table 5; determining the level of expression of the same one or more genes in cells/fibrotic tissue of the subject after treatment with miR-29 mimics or miR-29 antagonist; and determining the treatment to be effective, less effective, or not effective based on the expression levels prior to and after the treatment. That is, in one embodiment, the genes listed in Table 5 serve as a biomarker for clinical efficacy of the miR-29 mimic or miR-29 antagonist treatment. In one embodiment, a statistically significant difference in the expression of the genes prior to and after treatment indicates the treatment to be effective. In another embodiment, at least 1-fold, 1.5-fold, 2-fold, 2.5-fold, 3-fold, 3.5-fold, or 4-fold difference in the expression of the genes prior to and after treatment indicates the treatment to be effective.

The present invention also provides pharmaceutical compositions comprising a therapeutically effective amount of one or more microRNA mimetic compounds of miR-29a, miR-29b, and/or miR-29c according to the invention or a pharmaceutically acceptable salt thereof, and a pharmaceutically acceptable carrier or excipient.

In one embodiment, the pharmaceutical composition comprises a therapeutically effective amount of a miR-29a mimetic compound and a pharmaceutically acceptable carrier or excipient, wherein the first strand of the mimetic compound comprises a mature miR-29a sequence and the second strand is substantially complementary to the first strand. In another embodiment, the pharmaceutical composition comprises a therapeutically effective amount of a miR-29b mimetic compound and a pharmaceutically acceptable carrier or excipient, wherein the first strand of the mimetic compound comprises a mature miR-29b sequence and the second strand is substantially complementary to the first strand. In yet another embodiment, the pharmaceutical composition comprises a therapeutically effective amount of a miR-29c mimetic compound and a pharmaceutically acceptable carrier or excipient, wherein the first strand of the mimetic compound comprises a mature miR-29c sequence and the second strand is substantially complementary to the first strand.

In some embodiments, the pharmaceutical composition comprises a therapeutically effective amount of at least two microRNA mimetic compounds of the invention and a pharmaceutically acceptable carrier or excipient. For instance, a pharmaceutical composition may comprise a combination of a miR-29a and a miR-29b mimics; a miR-29a and a miR-29c mimics; or a miR-29b and a miR-29c mimics. Alternatively, the composition may comprise two mimics of the same microRNA. In yet some other embodiments, the invention provides pharmaceutical compositions comprising a therapeutically effective amount of three microRNA mimetic compounds of the invention and a pharmaceutically acceptable carrier or excipient. For instance, a pharmaceutical composition may comprise a combination of a miR-29a, a miR-29b and a miR-29c mimics.

Preferably, in the pharmaceutical compositions comprising at least two microRNA mimetic compounds according to the invention, the first and the second mimetic compounds or the first, second and the third mimetic compounds are present in equimolar concentrations. Other mixing ratios such as about 1:2, 1:3, 1:4, 1:5, 1:2:1, 1:3:1, 1:4:1, 1:2:3, 1:2:4 are also envisioned for preparing pharmaceutical compositions comprising at least two of the miR-29a, miR-29b, and miR-29c mimetic compounds.

In some embodiments, one or more microRNA mimetic compounds of the invention may be administered concurrently but in separate compositions, with concurrently referring to mimetic compounds given within a short period, for instance, within about 5, 10, 20, or 30 minutes of each other. In some other embodiments. miR-29a, miR-29b, and/or miR-29c mimetic compounds may be administered in separate compositions at different times.

The invention also encompasses embodiments where additional therapeutic agents may be administered along with miR-29a, miR-29b, and/or miR-29c mimetic compounds. In one embodiment, the additional therapeutic agent is a second anti-fibrotic agent. The additional therapeutic agents may be administered concurrently but in separate formulations or sequentially. In other embodiments, additional therapeutic agents may be administered at different times prior to after administration of miR-29a, miR-29b, and/or miR-29c mimetic compounds. Where clinical applications are contemplated, pharmaceutical compositions will be prepared in a form appropriate for the intended application. Generally, this will entail preparing compositions that are essentially free of pyrogens, as well as other impurities that could be harmful to humans or animals.

Colloidal dispersion systems, such as macromolecule complexes, nanocapsules, microspheres, beads, and lipid-based systems including oil-in-water emulsions, micelles, mixed micelles, liposomes and exosomes, may be used as delivery vehicles for miR-29a, miR-29b, and/or miR-29c mimetic compounds. In some embodiments, miR-29 mimics of the present invention may be formulated into liposome particles, which can then be aerosolized for inhaled delivery.

Commercially available fat emulsions that are suitable for delivering the nucleic acids of the invention to target tissues include Intralipid®, Liposyn®, Liposyn® II, Liposyn® III, Nutrilipid, and other similar lipid emulsions. A preferred colloidal system for use as a delivery vehicle in vivo is a liposome (i.e., an artificial membrane vesicle). The preparation and use of such systems is well known in the art. Exemplary formulations are also disclosed in U.S. Pat. Nos. 5,981,505; 6,217,900; 6,383,512; 5,783,565; 7,202,227; 6,379,965; 6,127,170; 5,837,533; 6,747,014; and WO03/093449, which are herein incorporated by reference in their entireties.

In certain embodiments, liposomes used for delivery are amphoteric liposomes such SMARTICLES® (Marina Biotech, Inc.) which are described in detail in U.S. Pre-grant Publication No. 20110076322. The surface charge on the SMARTICLES® is fully reversible which make them particularly suitable for the delivery of nucleic acids. SMARTICLES® can be delivered via injection, remain stable, and aggregate free and cross cell membranes to deliver the nucleic acids.

One will generally desire to employ appropriate salts and buffers to render delivery vehicles stable and allow for uptake by target cells. Aqueous compositions of the present invention comprise an effective amount of the delivery vehicle comprising the miR-29 mimic (e.g. liposomes or other complexes) dissolved or dispersed in a pharmaceutically acceptable carrier or aqueous medium. The phrases "pharmaceutically acceptable" or "pharmacologically acceptable" refers to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the polynucleotides of the compositions.

In one embodiment, pharmaceutical compositions of the invention are formulated for pulmonary, nasal, intranasal or ocular delivery and can be in the form of powders, aqueous solutions, aqueous aerosols, nasal drops, aerosols, and/or ocular drops. Solid formulations for nasal/intranasal administration may contain excipients such as lactose or dextran. Liquid formulations for nasal/intranasal administration may be aqueous or oily solutions for use in the form of aerosols, nasal drops or metered spray. Formulations for pulmonary/nasal/intranasal administration may also include surfactants such as, for example, glycocholic acid, cholic acid, taurocholic acid, ethocholic acid, deoxycholic acid, chenodeoxycholic acid, dehydrocholic acid, glycodeoxycholic acid, salts of these acids, and cyclodextrins.

In some embodiments, formulations for pulmonary/nasal/intranasal administration via inhalation include, but are not limited to a dry powder formulation, a liposomal formulation, a nano-suspension formulation, or a microsuspension formulation.

In some embodiments, pharmaceutical compositions for pulmonary/nasal/intranasal delivery are administered using an inhalation device. The term "inhalation device" refers to any device that is capable of administering a miR-29 mimic composition to the respiratory airways of the subject. Inhalation devices include devices such as metered dose inhalers (MDIs), dry powder inhalers (DPIs), jet nebulizers, ultrasonic wave nebulizers, heat vaporizers, soft mist inhalers, thermal aerosol inhalers, electrohydrodynamic-based solution misting inhaler. Inhalation devices also include high efficiency nebulizers. In some embodiments, a nebulizer is a jet nebulizer, an ultrasonic nebulizer, a pulsating membrane nebulizer, a nebulizer comprising a vibrating mesh or plate with multiple apertures, a nebulizer comprising a vibration generator and an aqueous chamber, or a nebulizer that uses controlled device features to assist inspiratory flow of the aerosolized aqueous solution to the lungs of the subject. Nebulizers, metered dose inhalers, and soft mist inhalers deliver pharmaceuticals by forming an aerosol which includes droplet sizes that can easily be inhaled.

In some embodiments, a composition administered with a high efficiency nebulizer comprises one or more miR-29 mimics and pharmaceutically acceptable excipients or carriers such as purified water, mannitol, surfactants, and salts such as sodium chloride and sodium EDTA, etc.

The active compositions of the present invention may include classic pharmaceutical preparations. Administration of these compositions according to the present invention may be via any common route so long as the target tissue is available via that route. This includes oral, nasal (e.g. inhalational), ocular, or buccal. Alternatively, administration may be by intravenous, intradermal, subcutaneous, intraocular or intramuscular injection, or by direct injection into pulmonary or cardiac tissue. Pharmaceutical compositions comprising miRNA mimics may also be administered by catheter systems or systems that isolate coronary circulation for delivering therapeutic agents to the heart. Various catheter systems for delivering therapeutic agents to the heart and coronary vasculature are known in the art. Some non-limiting examples of catheter-based delivery methods or coronary isolation methods suitable for use in the present invention are disclosed in U.S. Pat. Nos. 6,416,510; 6,716,196; 6,953,466, WO 2005/082440, WO 2006/089340, U.S. Patent Publication No. 2007/0203445, U.S. Patent Publication No. 2006/0148742, and U.S. Patent Publication No. 2007/0060907, which are all herein incorporated by reference in their entireties. Such compositions would normally be administered as pharmaceutically acceptable compositions as described herein.

In another embodiment of the invention, compositions comprising miR-29 mimics as described herein may be formulated as a coating for a medical device, such as a stent, balloon, or catheter. Particularly useful in methods of treating cardiac fibrosis in a subject, the miR-29 mimics can be used to coat a metal stent to produce a drug-eluting stent. A drug-eluting stent is a scaffold that holds open narrowed or diseased arteries and releases a compound to prevent cellular proliferation and/or inflammation. The mimetic compounds may be applied to a metal stent imbedded in a thin polymer for release of the agonists or inhibitors over time. Methods for device-based delivery and methods of coating devices are well known in the art, as are drug-eluting stents and other implantable devices. See, e.g., U.S. Pat. Nos. 7,294,329, 7,273,493, 7,247,313, 7,236,821, 7,232,573, 7,156,869, 7,144,422, 7,105,018, 7,087,263, 7,083,642, 7,055,237, 7,041,127, 6,716,242, and 6,589,286, and WO 2004/004602, which are herein incorporated by reference in their entireties. Thus, the present invention includes a medical device, such as a balloon, catheter, or stent, coated with a miR-29 mimic.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above.

The compositions of the present invention generally may be formulated in a neutral or salt form. Pharmaceutically-acceptable salts include, for example, acid addition salts (formed with the free amino groups of the protein) derived from inorganic acids (e.g., hydrochloric or phosphoric acids), or from organic acids (e.g., acetic, oxalic, tartaric, mandelic, and the like). Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like).

Upon formulation, solutions are preferably administered in a manner compatible with the dosage formulation and in such amount as is therapeutically effective. The formulations may easily be administered in a variety of dosage forms such as injectable solutions, drug release capsules, drug-eluting stents or other coated vascular devices, and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous, intradermal, intraocular, and intraperitoneal administration.

This invention is further illustrated by the following additional examples that should not be construed as limiting. Those of skill in the art should, in light of the present disclosure, appreciate that many changes can be made to the specific embodiments which are disclosed and still obtain a like or similar result without departing from the spirit and scope of the invention.

All patent and non-patent documents referenced throughout this disclosure are incorporated by reference herein in their entirety for all purposes.

EXAMPLES

Example 1

In Vitro Activity of MiR-29 Mimic

Figure 1A:
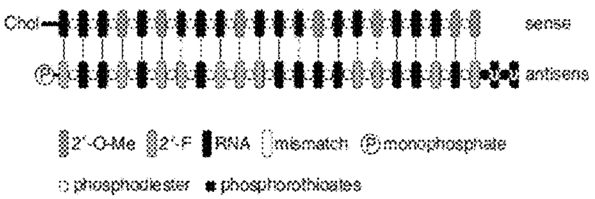
FIG. 1A. The double-stranded miR-29 mimics design contains a 'guide strand' or 'antisense strand' that is identical to the miR-29b, with a UU overhang on the 3' end, modified to increase stability, and chemically phosphorylated on the 5' end and a 'passenger strand' or 'sense strand' that contains 2'-O-Me modifications to prevent loading into RNA-induced silencing complex (RISC) as well as increase stability and is linked to cholesterol for enhanced cellular uptake. Several mismatches are introduced in the sense strand to prevent this strand from functioning as an antimiR.
Figure 1B:
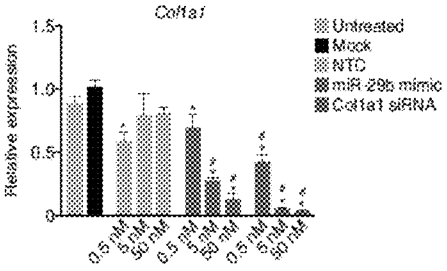
FIG. 1B. Transfection experiments in NIH 3T3 show a dose-dependent decrease in Col1a1 with increasing amount of miR-29b mimic compared to either untreated or mock treated cells. An siRNA directly targeting Col1a1 was taken along as a positive control. * $p<0.05$ versus mock, # $p<0.05$ versus untreated.

To test for functional efficacy, a miR-29b mimic containing SEQ ID NO: 2 as the first strand and SEQ ID NO: 1 as the second strand was transfected into a mouse fibroblast cell line (NIH 3T3) and the effect on Collagen1a1 (Col1a1) expression, a known direct target gene of miR-29 (van Rooij et al, 2008), was measured using qPCR. Increasing amount of miR-29b mimic showed a dose-dependent decrease in Col1a1, compared to untreated, mock transfected (without any oligo) or non-targeting control (NTC) oligo treated cells, indicating the miR-29b mimic to be functional. A siRNA directly targeting Col1a1 was used as a positive control (FIG. 1B).

Example 2

In Vivo Distribution, Stability and Clearance of MiR-29 Mimic

To explore the in vivo applicability and distribution of the miR-29 mimic, mice were injected intravenously with 10, 50, 100, or 125 mg per kg of the miR-29b mimic containing SEQ ID NO: 2 as the first strand and SEQ ID NO: 1 as the second strand and sacrificed four days later.

Total RNA was isolated from cardiac tissue samples by using TRIzol® reagent (solution of phenol and guanidine isothiocyanate) (Gibco/BRL). Northern blots to detect microRNAs were performed as previously described (van Rooij et al, 2008). A U6 probe served as a loading control (IDT). 10 μg of total RNA from the indicated tissues was loaded on 20% acrylamide denaturing gels and transferred to Zeta-probe GT genomic blotting membranes (Bio-Rad) by electrophoresis. After transfer, the blots were cross-linked and baked at 80° C. for 1 hr. To maximize the sensitivity of miRNA detection, oligonucleotide probes were labeled with the Starfire Oligos Kit (IDT, Coralville, Iowa) and $\alpha$-$^{32}$P dATP (Amersham or Perkin Elmer). Probes were hybridized to the membranes overnight at 39° C. in Rapid-hyb buffer (Amersham), after which they were washed twice for 10 minutes at 39° C. with 0.5× SSC containing 0.1% SDS. The blots were exposed and quantified by PhosphorImager analysis (GE HealthCare Life Sciences) and a U6 probe served as a loading control (ABI). The intensity of the radioactive signal was used to quantify the fold change in expression using a phosphorImager and ImageQuant (Bio-Rad).

For real-time PCR analysis, RNA was extracted from cardiac tissue using Trizol (Invitrogen) after which one to two μg RNA from each tissue sample was used to generate cDNA using Super Script II reverse transcriptase per manufacturer's specifications (Invitrogen). Taqman MicroRNA assay (Applied Biosystems, ABI) was used to detect changes in miRNAs or genes according the manufacturer's recommendations, using 10-100 ng of total RNA. U6 was used a control for miRNA analysis and GAPDH was used as a control for gene analysis.

Figure 1C:
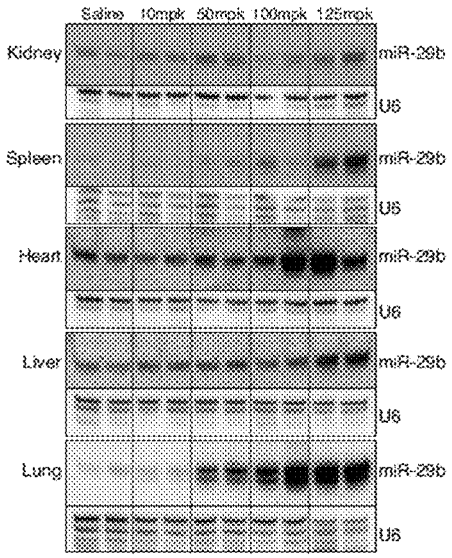
FIG. 1C. Northern blot analysis for miR-29b in different tissues 4 days after intravenous injection with 10, 50, 100, or 125 mpk miR-29b mimic indicates delivery to all tissues at the highest dose, with the most effective delivery taking place to the lungs and spleen compared to saline injected mice. U6 is used as a loading control.
Figure 1D:
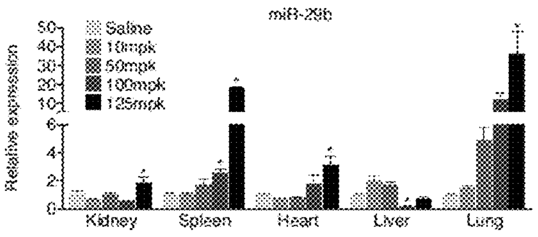
FIG. 1D. Real-time quantification of miR-29b mimicry indicates an increased level of miR-29b at the higher dose levels with the most efficient delivery to the lungs and spleen (d=4 per group). *$p<0.05$ versus Saline injected animals.
Figure 5:
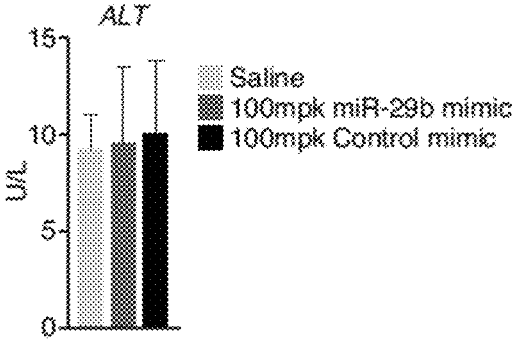
FIG. 5. miR-29b mimic does not induce general signs of toxicity. MiR-29b mimic treatment does not induce any overt signs of liver or kidney toxicity as indicated by the lack of change in aspartate or alanine transaminases (AST and ALT). n=4 per group.
Figure 6A:
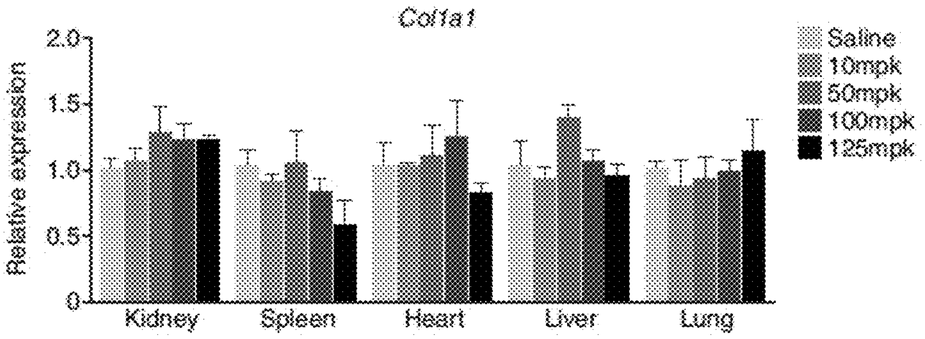
FIG. 6A. Increasing doses of miR-29b mimic fail to induce overt changes in gene expression under baseline conditions. Real-time PCR analysis indicates there to be no significant changes in expression in the different tissue 4 days after treatment with increasing doses of miR-29b mimic for Col1a1 compared to Saline injected mice. n=4 per group. * p<0.05 compared to Saline injected.
Figure 6B:
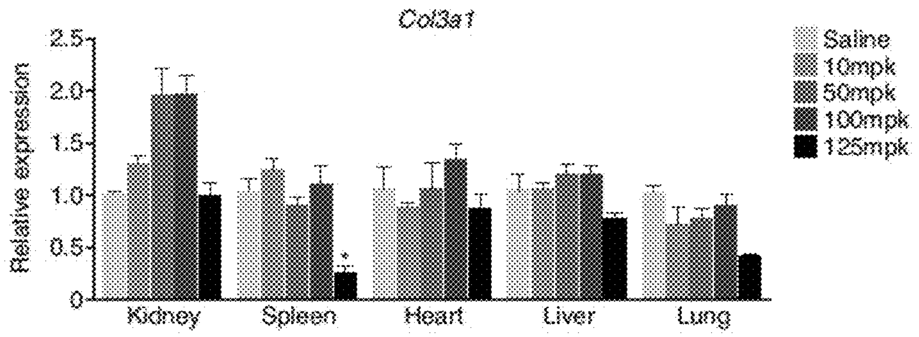
FIG. 6B. Increasing doses of miR-29b mimic fail to induce overt changes in gene expression under baseline conditions. Real-time PCR analysis indicates there to be no significant changes in expression in the different tissue 4 days after treatment with increasing doses of miR-29b mimic for Col3a1 compared to Saline injected mice. n=4 per group. * p<0.05 compared to Saline injected.

Northern blot analysis on multiple tissues indicated little to no increase in miR-29b in kidney or liver samples compared to saline control. Cardiac distribution was detected; however this appeared to be quite variable and spleen delivery could be observed at the highest dose only. However, delivery to the lungs could be observed at all 3 of the highest doses four days after injection (FIG. 1C). No effects on liver function (transaminase, ALT) were observed in the plasma, indicating that these miRNA mimics are well tolerated at these doses (FIG. 5). Real-time PCR demonstrated similar results with robust dose-dependent distribution of the miR-29b mimic to the lung compared to saline injected animals (FIG. 1D). Additionally, real-time PCR analysis of miR-29 targets showed no regulation at the mRNA level in the treated animals except for Col3a1 at the highest dose in the spleen (FIG. 6). This suggests that the target genes are either at steady-state in non-stressed animals and that mimics lower target genes when they are elevated, or that functional delivery was inadequate or insufficient.

Figure 1E:
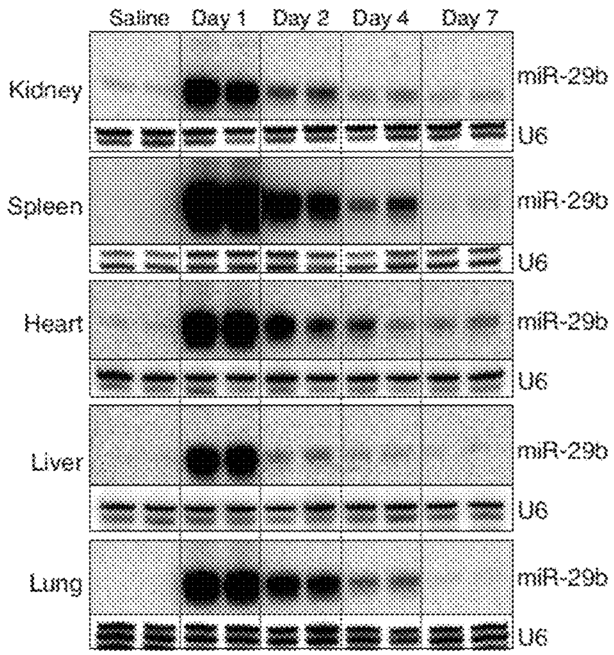
FIG. 1E. Northern blot analysis for miR-29b in different tissues 1, 2, 4 and 7 days after intravenous injection with 125 mpk of mimic indicates the presence of miR-29b mimic in all tissues examined, with a longer detection in lung and spleen. U6 is used as a loading control.
Figure 1F:
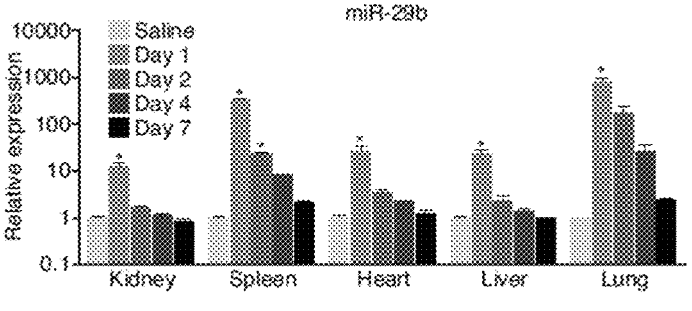
FIG. 1F. Real-time quantification of miR-29b mimicry indicates an increased level of miR-29b in all tissues measured which is maintained the longest in lungs and spleen (n=4 per group). *$p<0.05$ versus Saline injected animals.
Figure 7A:
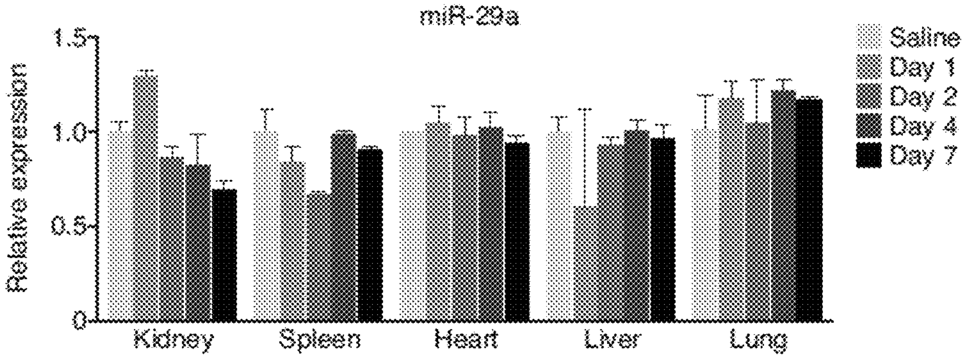
FIG. 7A. miR-29b mimic specifically increases miR-29b. MiR-29b mimicry specifically increases the level of miR-29b without affecting the level of miR-29a compared to Saline injected mice. n=4 per group.
Figure 7B:
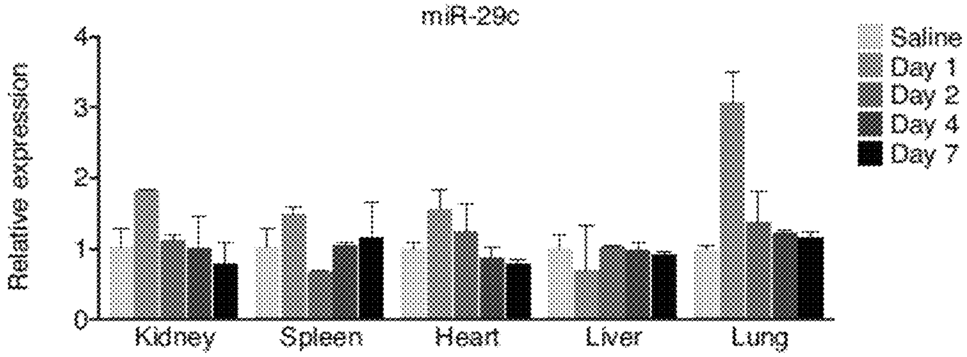
FIG. 7B. miR-29b mimic specifically increases miR-29b. MiR-29b mimicry specifically increases the level of miR-29b without affecting the level of miR-29c compared to Saline injected mice. The increase in miR-29c at day 1 might be due to some cross-reactivity of the real-time probe. n=4 per group.
Figure 8A:
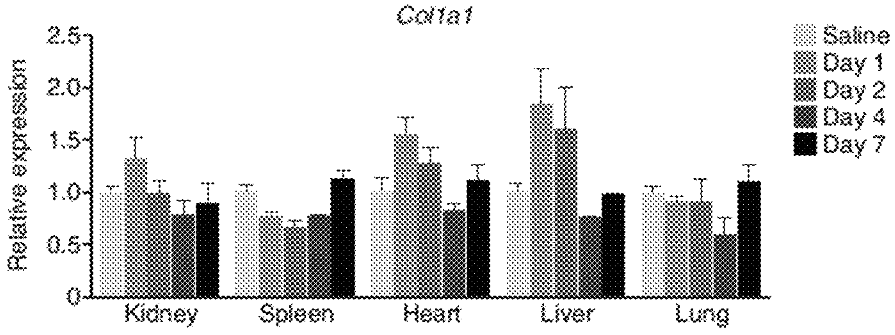
FIG. 8A. miR-29b mimic does not induce any target changes in baseline conditions. Real-time PCR analysis showed the absence of significant target changes at the indicated timepoints after injecting 125 mpk of miR-29b mimic for Col1a1 compared to Saline injected mice. n=4 per group.
Figure 8B:
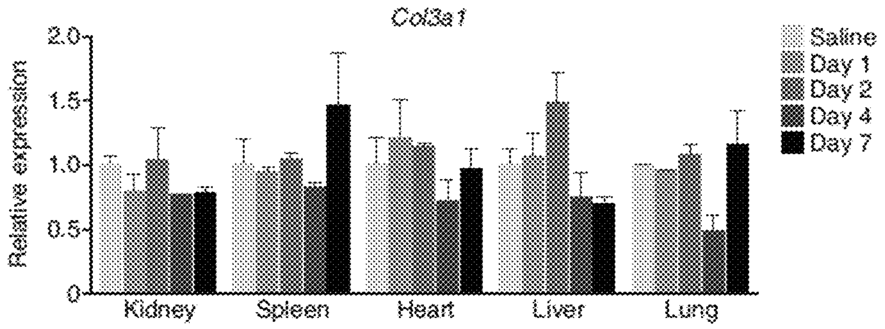
FIG. 8B. miR-29b mimic does not induce any target changes in baseline conditions. Real-time PCR analysis showed the absence of significant target changes at the indicated timepoints after injecting 125 mpk of miR-29b mimic for Col3a1 compared to Saline injected mice. n=4 per group.

To gain more insights into the in vivo stability of miRNA mimics, 125 mpk of the miR-29b mimic was injected into mice and they were sacrificed 1, 2, 4, or 7 days later. Robust presence of miR-29b mimic could be detected by both Northern blot and real-time PCR analysis one day after injection in all tissues examined, however tissue clearance greatly differed thereafter (FIGS. 1E and F). Liver and kidney rapidly cleared miR-29b mimic with minimal detection after day 1. Lung and spleen demonstrated the most pronounced detection of miR-29b mimic over time, which was sustained at least 4 days post-treatment (FIGS. 1E and 1F). The increase was specific for miR-29b without any effect on miR-29a and miR-29c levels as measured by real-time PCR (FIG. 7). Also here real-time PCR analysis of miR-29 targets showed no downregulation at the mRNA level in non-stressed animals (FIG. 8).

Together these data indicate that unformulated miR-29b mimic can increase the miRNA level with tissue-dependent clearance and delivery efficiency, without any clear effect on gene expression under baseline conditions.

Example 3

MiR-29b Mimic Blunts Bleomycin-Induced Pulmonary Fibrosis

Current treatments of tissue fibrosis mostly rely on targeting the inflammatory response; however these treatments are ultimately ineffective in preventing progression of the disease, underscoring the need for new mechanistic insights and therapeutic approaches (Friedman et al, 2013). Recent studies indicate the involvement of miRNAs in pulmonary fibrosis (Pandit et al, 2011).

Due to the preferential lung distribution of the miR-29b mimic, the question of whether stress and subsequent induction of target gene expression would allow for detectable changes in mRNA target genes and downstream therapeutic effects in response to treatment with miR-29b mimic was explored. To test this, the bleomycin-induced model of pulmonary fibrosis was used as previously described (Pandit et al, 2010). Specifically, mice were anesthetized by placing them in a chamber having paper towels soaked with 40% isoflurane solution. 0.0375 U of bleomycin (Hospira, Ill.) was administered intratracheally in 50 μl of 0.9% saline. To determine the effect of miR-29b mimicry on early fibrosis, control (saline-treated) and bleomycin-treated mice were injected with 100 mg per kg of the miR-29b mimiccontaining SEQ ID NO: 2 as the first strand and SEQ ID NO: 1 as the second strand, control mimic or a comparable volume of saline at two time-points: 3 and 10 days after bleomycin treatment; the animals were sacrificed and lungs harvested at day 14. To determine the effect of miR-29b mimicry on established fibrosis, the miR-29b mimic was administered at days 10, 14 and 17 after bleomycin or saline and the mice were sacrificed at day 21. In both protocols, the lungs were harvested for histological analysis, hydroxyproline assay and RNA extraction.

Figure 2A:
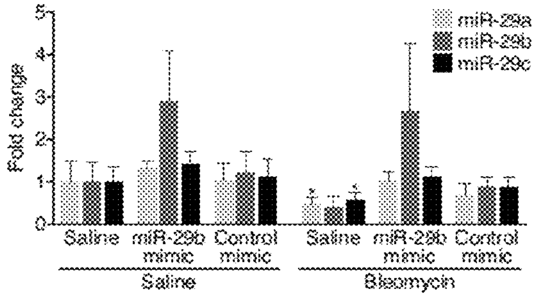
FIG. 2A. Real-time PCR analysis indicates a reduction in all miR-29 family members in response to bleomycin, while miR-29 mimic treatment resulted in the increased detection of miR-29b levels compared to either control or saline injected animals. *$p<0.05$ vs Saline/Saline FIG. 2B. Real-time PCR analysis indicated a comparable decline in miR-29 levels in pulmonary biopsies of patients with idiopathic pulmonary fibrosis (IPF) compared to normal controls. *$p<0.05$ vs Normal FIG. 2C. Histological examination by trichrome staining showing pronounced fibrotic and inflammatory response in response to bleomycin, which was blunted by miR-29b mimic treatment. Scale bar indicates 100 μm.
Figure 2B:
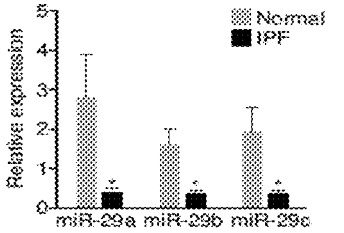
FIG. 2D. Hydroxyproline measurements to assay for total collagen content showed a significant increase following bleomycin treatment in both saline and control treated groups, while there was no statistical difference in the miR-29 mimic treated group between Saline and bleomycin treated mice.
FIG. 2E-G. Cytokine measurements on bronchoalveolar lavage (BAL) fluids indicated a significantly higher concentrations of IL-12, IL-4 and G-CSF were detectable in BAL fluids from lungs from bleomycin treated mice, which was reduced with miR-29b mimic (n=4), *$p<0.05$.
FIG. 2H. Bleomycin treatment increases the detection of immune cells in BAL fluids which was significantly reduced in the presence of miR-29b mimic while the Control mimic had no effect. (n=4), * p<0.05 vs Saline/Bleo, ^p<0.05 vs Control/Bleo FIG. 3A-B. Bleomycin treatment increases the expression of Col1a1 and Col3a1 and the presence of miR-29b mimic inhibits Col1a1 and Col3a1 as measured by real-time PCR. MiR-29b mimicry has no effect on target repression under baseline conditions. (n=6-8), * p<0.05

As expected, 14 days after bleomycin treatment, miR-29 levels were reduced, while miR-29b mimic treatment resulted in the increased detection of miR-29b levels compared to either control or saline injected animals as measured by real-time PCR, albeit with a high level of variation (FIG. 2A). To determine whether a similar decline in miR-29 levels is observed in humans, sixteen lung tissue samples were obtained from surgical remnants of biopsies or lungs explanted from patients with idiopathic pulmonary fibrosis (IPF) who underwent pulmonary transplantation. Samples were obtained from University of Pittsburgh Health Sciences Tissue Bank. A comparable decline in miR-29 levels was observed in pulmonary biopsies of patients with idiopathic pulmonary fibrosis (IPF) compared to normal controls (FIG. 2B).

Figure 2C:
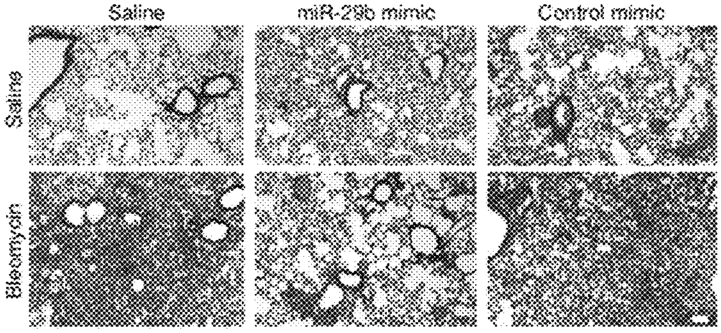

For histological examination, lung tissue sections (4 μm) were stained with Masson Trichrome (collagen/connective tissue), two slices per animal, two animals per group. Immune staining was performed after paraffin removal, hydration, and blocking, following the recommendation of the manufacturer (ABC detection system form Vector's lab, USA). Sections were incubated overnight at 4° C. with the primary antibody (Igf1, diluted 1:100 in PBS) and during 1 hour at room temperature with the secondary antibodies (Invitrogen, USA). The sections were counterstained with hematoxylin. The primary antibody was replaced by nonimmune serum for negative controls. Finally, sections were mounted with mounting medium (DAKO, USA) and analyzed using a Nikon microscope. Histological analysis showed a clear and robust fibrotic and inflammatory response to bleomycin treatment, which was blunted by miR-29b mimic treatment (FIG. 2C).

Additionally, lung hydroxyproline was analyzed for total collagen content with hydroxyproline colorimetric assay kit from Biovision (Milpitas, Calif.) following manufacturer's instruction. Briefly, the lungs from control and experimental mice were dried until constant weight and hydrolyzed in 12N HCl for 3 hours at 120° C. The digestions reacted with Chloramine T reagent and visualized in DMAB reagent. The absorbance was measured at 560 nm in a microplate reader. Data are expressed as μg of hydroxyproline/right lung.

Figure 2D:
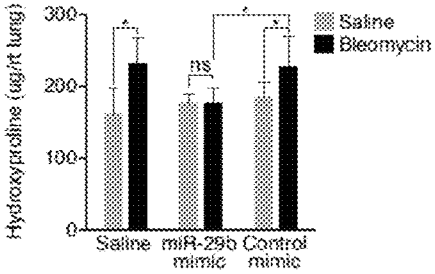

The hydroxyproline analysis indicated a significant increase following bleomycin treatment in both saline and control treated groups, while there was no statistical difference in the miR-29 mimic treated group between saline and bleomycin-treatcd mice, indicating that miR-29b mimic treatment blunts bleomycin-inducced pulmonary fibrosis (FIG. 2D).

Innate immune effector signaling pathways act as important drivers of myofibroblast transdifferentiation by provoking fibrosis. To further characterize the therapeutic effects of miR-29b mimic in the setting of bleomycin-induced pulmonary fibrosis, bronchoalveolar lavage (BAL) was performed on these mice and cytokine levels were assessed using a human Cytokine/Chemokine Panel from Bio-Rad. The entire procedure was performed following manufacturer's instruction. Briefly, BALs were diluted five-fold and assay was performed in 96-well filter plates. For the detection step, samples were incubated for 30 min with streptavidin conjugated to R-phycoerythrin and analyzed in the Bio-Plex suspension array system (Bio-Rad). Raw data was analyzed using Bioplex Manager software 6.0 (Bio-Rad). The cytokine standards supplied by the manufacturer were used to calculate the concentrations of the samples. The analytes that were below the detection range were not included in date interpretation. Also, samples that had a particular analyte below the detection range were excluded while calculating the median value.

Figure 2E:
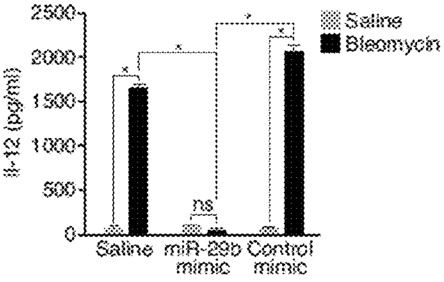
Figure 2F:
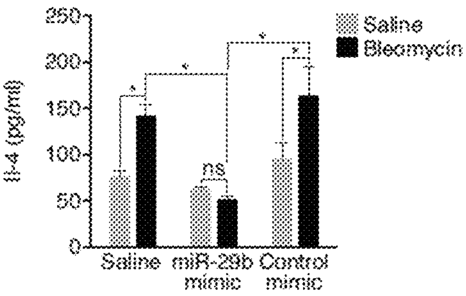
Figure 2G:
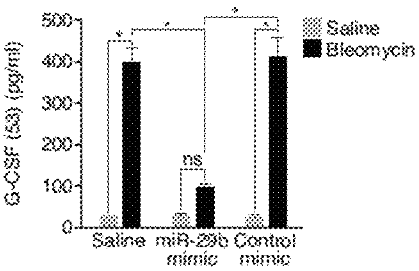
Figure 2H:
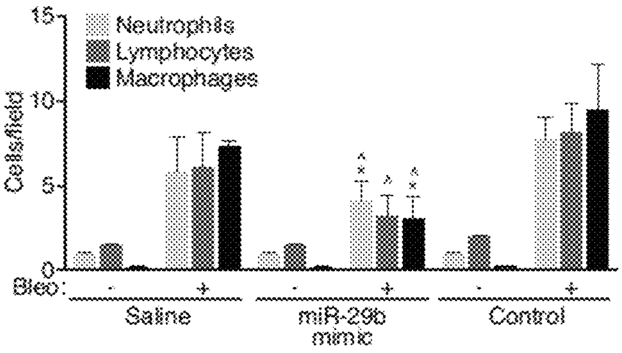
Figure 9:
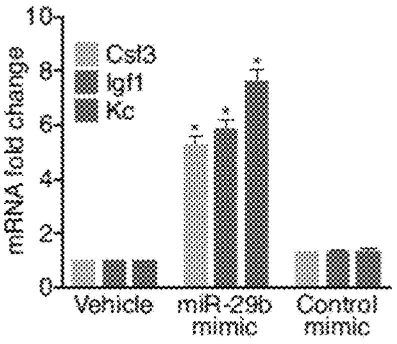
FIG. 9. miR-29b mimic effects on gene expression in RAW cells. Real-time PCR analysis showed significant increases in Csf3, Igf1, and Kc expression after miR-29b mimic treatment compared to vehicle or control mimic. * p<0.05 compared to Vehicle injected.

Significantly higher concentrations of IL-12, IL-4 and G-CSF were detectable in BAL fluids from lungs from bleomycin-treated mice, which were reduced with miR-29b mimic (FIGS. 2E to 2G). Additionally, the bleomycin-induced elevation of detectable immune cells in BAL fluids was significantly reduced in the presence of miR-29b mimic (FIG. 2H), indicating an inhibitory effect on the immune response by miR-29b, which is likely secondary to the antifibrotic-effect. To determine if miR-29 mimicry has a direct effect on macrophages, miR-29b mimic or control was transfected into macrophage cells, RAW 264.7, and the cell supernatant was harvested at 24 and 48 hours after transfection. IFN-r, IL-1B, IL-2, IL-4, IL-5, IL-6, KC, IL-10, IL-12P70, and TNF-α were assessed, with no significant differences observed between miR-29b mimic and control (data not shown). By real-time PCR analysis, there were no significant differences in Tgfb1, Ctgf, FGF1, or PDGF expression; however, a significant difference in Csf3, Igf1, and Kc expression was observed (FIG. 9 and data not shown).

Figure 3A:
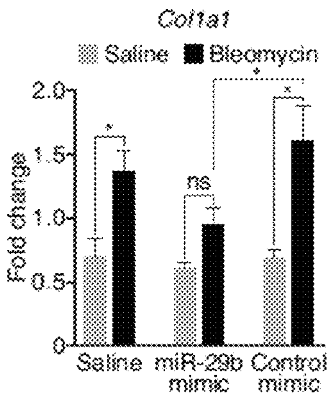
FIG. 3C. IGF1 levels in BAL fluids increase following bleomycin treatment which were significantly blunted in the presence of miR-29 mimic compared to both Saline and Control mimic treated mice. (n=4), * p=0.05.
FIG. 3D. Immunohistochemistry demonstrated robust detection of IGF1 after bleomycin treatment, which was reduced in the miR-29b mimic treated group compared to Saline or Control mimic treated mice. Scale bar indicates 50 μm.
Figure 3B:
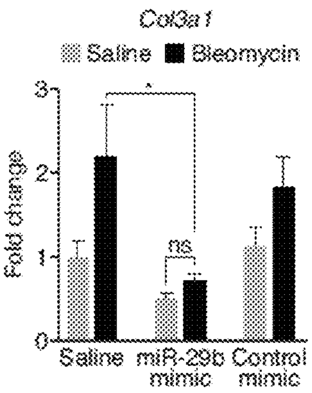
Figure 3C:
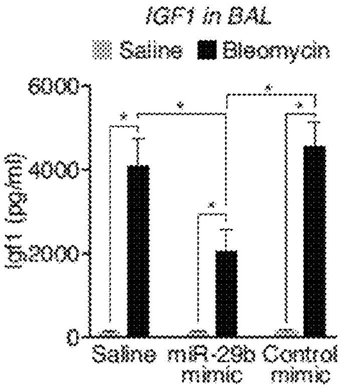
Figure 3D:
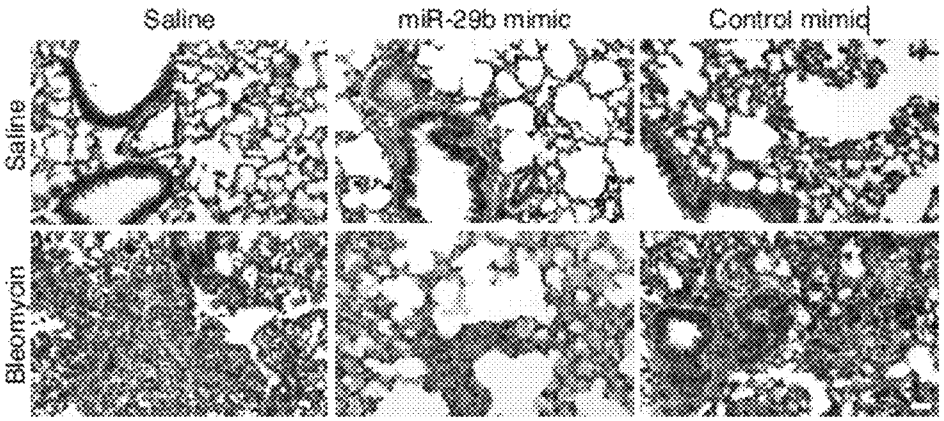

Since it has been well validated that miR-29 functions through the regulation of many different extracellular matrix related genes (van Rooij & Olson, 2012), the regulation of a subset of these target genes was confirmed. While a significant increase in Col1a1 and a trend increase in Col3a1 expression were observed with bleomycin treatment in both saline and control-treated groups, the detection of Col1a1 and Col3a1 was significantly blunted in the presence of miR-29b mimic in the bleomycin-treated mice (FIGS. 3A and 3B). Interestingly, the increase in Igf1 levels in BAL fluids following bleomycin treatment were significantly blunted in the presence of miR-29 mimic compared to both saline and control-treated mice (FIG. 3C). Furthermore, immunohistochemistry for Igf1 demonstrated robust reductions in Igf1 after bleomycin in miR-29b mimic-treated groups compared to saline or controls (FIG. 3D).

Figure 4A:
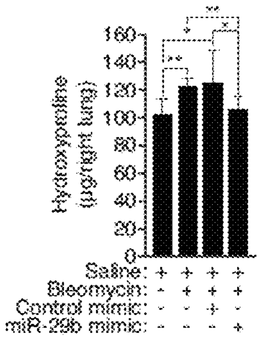
FIG. 4A. Hydroxyproline assessment showed a significant increase following bleomycin treatment in both saline and control treated groups, however, there was no statistical difference in the miR-29 mimic treated group between Saline and bleomycin treated mice. *P<0.05 (n=8)
Figure 4B:
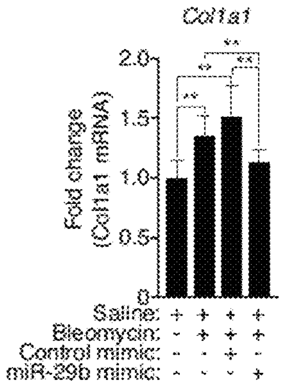
FIG. 4B-C. Real-time PCR analysis for Col1a1 (B) and Col3a1 (C) showed a significant increase with bleomycin treatment. miR-29b mimic treatment normalized both Col1a1 and Col3a1 to vehicle treated expression levels. *P<0.05 (n=8)
Figure 4C:
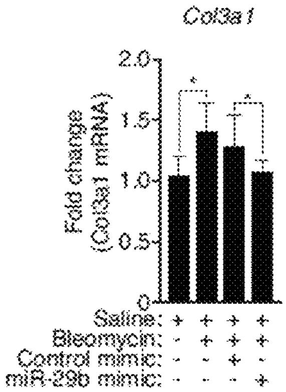
Figure 4D:
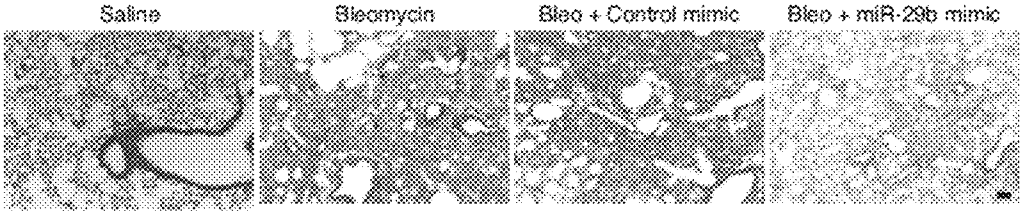
FIG. 4D. Histological examination by trichrome staining showing robust fibrosis in response to bleomycin, which was blunted by miR-29b mimic treatment.

After establishing that early (day 3 and day 10) miR-29 mimicry was sufficient to prevent bleomycin induced fibrosis, the ability of miR-29 mimicry to affect established fibrosis was investigated. For that purpose, the miR-29b mimic administration was started at day 10 post bleomycin, and the doses were repeated at days 14 and 17, after which the lungs were harvested at day 21. Hydroxyproline assessment of the right lung showed a significant increase with bleomycin in both saline and control-treated lungs; however miR-29b mimic treatment blunted this effect (FIG. 4A). Furthermore, bleomycin treatment resulted in significant increases in Col1a1 and Col3a1 expression, which was also normalized with miR-29b mimic treatment (FIGS. 4B and 4C). Histological assessment by trichrome staining corroborated this effect, whereby bleomycin induced significant fibrosis with saline or control treatment which was blunted with miR-29b mimicry (FIG. 4D).

Figure 4E:
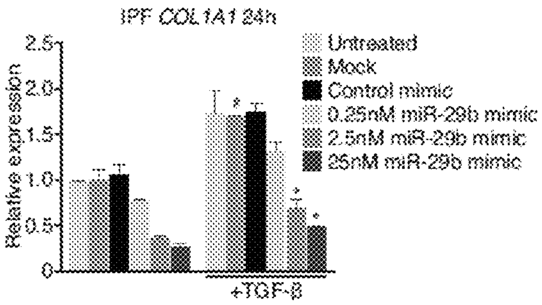
FIG. 4E-F. Primary pulmonary fibroblasts from patients with IPF were treated with vehicle or TGF-β and transfected with control mimic or miR-29b mimic. Real-time PCR was performed for Col1a1 (E) and Col3a1 (F), miR-29b mimic treatment showed a dose-dependent reduction in both collagens.
Figure 4F:
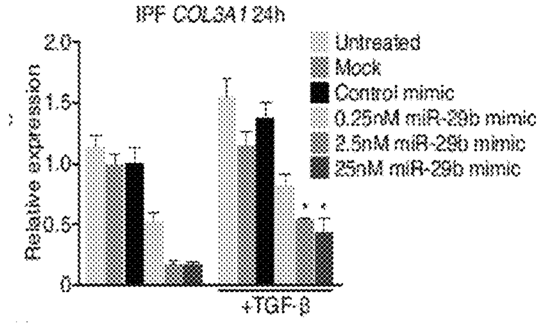
Figure 4G:
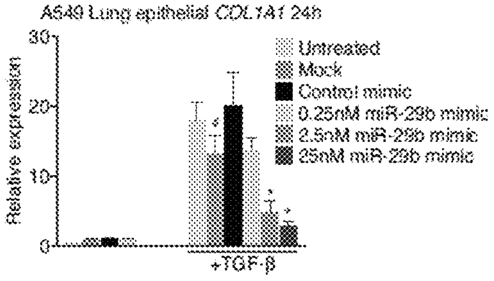
FIG. 4G-H. A549 cells were treated with vehicle or TGF-β and transfected with control mimic or miR-29b mimic. Real-time PCR was performed for Col1a1 (G) and Col3a1 (H), miR-29b mimic treatment showed a dose-dependent reduction in expression of both Col1a1 and Col3a1.
Figure 4H:
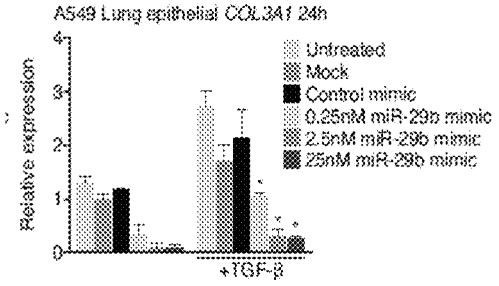

While it was believed that these observed effects were mediated through regulation of collagen production from lung fibroblasts, the effects from other collagen producing cells could not be ruled out. To address this issue, miR-29b mimic effects were assessed in vitro from different lung cells, including primary fibroblasts from IPF patients and A549 cells, a lung epithelial cell line. As expected, primary pulmonary fibroblasts from IPF patients show an increase in Col1a1 and Col3a1 in response to TGF-α (FIGS. 4E and 4F). This effect was dose-dependently blunted with miR-29b mimic treatment at both 24 and 48 hours (FIGS. 4E, 4F and data not shown). Similarly, A549 cells respond to TGF-α with robust increases in Col1a1 and Col3a1 expression (FIGS. 4G and 4H). Again, miR-29b mimic treatment is able to block collagen induction, in both TGF-α treated as well as baseline conditions (FIGS. 4G and 4H). The effects on collagen induction are much more robust in the A549 cells compared to primary IPF cells. However, this is likely due to the already high expression in primary fibroblasts from IPF patients. Additionally, miR-29 effects in the macrophage line, Thp-1, were also examined, but no collagen expression could be observed in the cells, regardless of stimulation (data not shown). These data suggest miR-29b mimicry is able to blunt collagen-induced expression in fibroblasts and epithelial cells. These data are in agreement with a paper by Xiao et al., in which they showed that gene transfer of miR-29 using a Sleeping Beauty-transposon system was capable of preventing and treating bleomycin-induced pulmonary fibrosis (Xiao et al, 2012), further underscoring the therapeutic potential for increasing miR-29.

The data described herein shows the feasibility of using microRNA mimics to restore the function of lost or down-regulated miRNAs. However, it is important to note that because RISC incorporation is required for appropriate miRNA function, careful design of the structural features of the synthetic oligonucleotide mimics is required. In addition, the data in the present application shows that delivery to the appropriate cell type or tissue provides effective miRNA mimicry. For instance, in the case of pulmonary fibrosis, direct delivery through the inhaled route provides better treatment efficacy compared to traditional routes of administration.

Example 4

MiR-29b Mimic Blunts Extracellular Matrix Production in the Skin

In addition to organ fibrosis, a number of studies have shown a role for miR-29 in dermal fibrosis such as in hypertrophic scars and keloids, and in cutaneous and other forms of systemic sclerosis (scleroderma). For example, fibroblasts and skin sections obtained from patients with systemic sclerosis showed a dramatic reduction in miR-29a levels compared to healthy controls (Maurer et al 2010). When overexpressed in systemic sclerosis fibroblasts, miR-29a was able to robustly reduce the expression of type I and III collagens, at both the RNA and protein level. Conversely, inhibition of miR-29 in normal fibroblasts resulted in an increase in these collagens. Further, bleomycin-treated skin showed a significant reduction in miR-29 as well, suggesting miR-29 down-regulation is broadly applicable in multiple indications of fibrosis (Maurer et al 2010). These results were further validated in another study where miR-29a transfection in healthy control dermal fibroblasts significantly down-regulated collagen expression. Additionally, miR-29a overexpression in dermal fibroblasts decreased secreted TIMP-1 and increased collagen gel degradation. These results were validated in fibroblasts from patients with systemic sclerosis as well (Ciechomska et al 2014). Collectively, these studies point to miR-29 mimicry as a therapeutic potential in local forms of fibrosis, including dermal fibrosis and systemic sclerosis.

To determine the effect of miR-29 agonism or antagonism in skin, a mouse incisional wound model was used. Specifically, male C57BL/6 mice were anesthetized with 2-5% inhaled isofluorane using an inhalation chamber and were maintained under 1% isofluorane on a nose cone for all procedures. Buprenorphine (0.1 mg/kg) was used as an analgesic for all surgical procedures. Animals were anesthetized, depilated by shaving and administration of Nair hair removal cream, and the skin site was prepared for incision by betadine and alcohol surgical scrub. One to two 1 cm long skin incisions were made on the backs of the mice. Incisions were closed with 2-5 interrupted sutures and were covered with Tegaderm transparent semi-occlusive dressing (3M). Mice with or without incisional skin wounds were treated with intradermal injection with vehicle (PBS), 100 nmol miR-29b mimic (comprising SEQ ID NO: 2 as the first strand and SEQ ID NO: 1 as the second strand) or 100 nmol antimiR-29, 3 days after incisional wound creation, by intradermal injection of oligonucleotide compounds or vehicle (PBS) in two 50 μL volumes located on either side of the incision midline, or by injection of a single 100 μL volume into adjacent, unwounded skin. The antimiR-29 has the sequence of 5'-lGs.dAs.dTs- .dTs.lTs.lCs.dAs.lAs.dAs.lTs.lGs.dGs.lTs.dGs.lCs.lTs-3' (SEQ ID NO: 36) where "l" represents a locked nucleotide, "d" represents a deoxyribonucleotides and "s" represents a phosphorothioate linkage. Mice were sacrificed 24 hours after administration of oligonucleotide compounds and skin at the treatment site(s) was harvested and snap frozen in liquid nitrogen for analysis of mRNA expression.

Total RNA was extracted from skin using Trizol (Invitrogen) and real-time PCR analysis was performed as described above except that GAPDH, B2M, HPRT1 and PPIB were used as controls for gene analysis of skin samples.

For microarray analysis, one μg total RNA per sample was sent to MOgene for microarray analysis as compared to a mouse universal reference RNA (Agilent) on an Agilent array (Mouse GE (V2), 4×44k-026655). Analysis was performed using ArrayStudio and heatmaps were generated using the R software program.

Figure 10A:
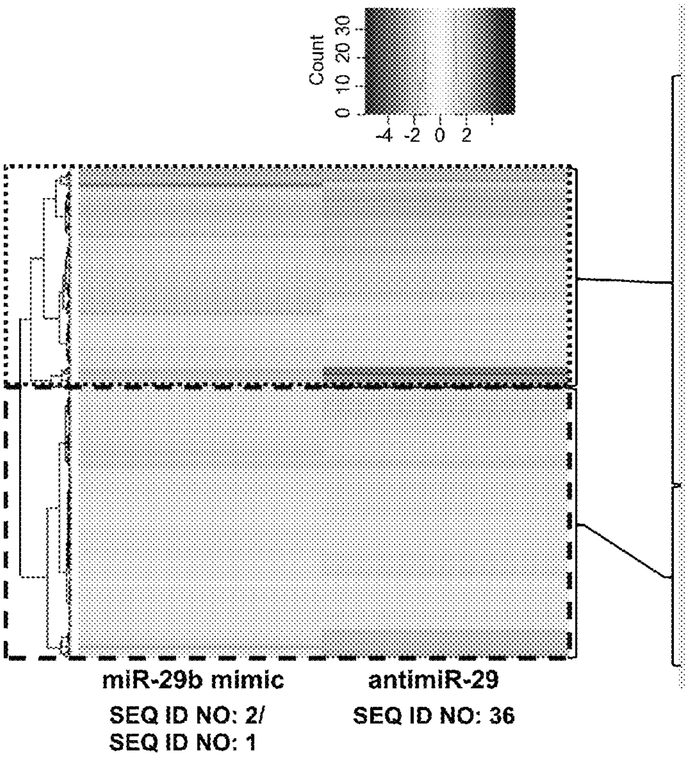
FIG. 10A. miR29b mimic and antimiR effects on gene expression in mouse skin. A heatmap of the microarray data is presented, where unregulated genes are represented in red and downregulated genes are represented in blue, and the intensity of the color is representative of the fold change relative to PBS control. The top portion of the heatmap (finely dashed box) contains genes which are repressed by miR-29b mimic treatment and upregulated by antimiR-29 treatment, and the bottom portion of the heatmap (wide dashed box) contains genes which are upregulated by miR-29b mimic treatment and repressed by antimiR-29 treatment. All fold change and significance values are presented in Table 5.

Using microarray analysis, positively and negatively regulated genes were identified relative to PBS controls. 228 genes were reciprocally regulated ($p<0.05$ or fold change >1.5) between the miR-29b mimic and antimiR-29 (FIG. 10 and Table 5). These miR-29 regulated genes and their orthologs in other species may be utilized as translational biomarkers to indicate response to treatment with a miR-29 agonist or miR-29 antagonist.

TABLE 5

| | miR-29b mimic | | antimiR-29 | |
|---|---|---|---|---|
| Gene | Fold change | p value | Fold change | p value |
| Cytl1 | −3.21 | 0.000 | 1.53 | 0.034 |
| Col3a1 | −2.68 | 0.074 | 1.61 | 0.352 |
| Col1a1 | −2.43 | 0.051 | 2.16 | 0.081 |
| Col1a2 | −2.38 | 0.028 | 2.26 | 0.036 |
| Fstl1 | −2.25 | 0.015 | 2.15 | 0.019 |
| Col5a2 | −2.19 | 0.005 | 1.95 | 0.012 |
| 4930543N07Rik | −2.13 | 0.005 | 3.10 | 0.000 |
| Faim2 | −2.13 | 0.083 | 2.42 | 0.049 |
| Tmem213 | −2.06 | 0.047 | 2.39 | 0.022 |
| Tgfb3 | −1.99 | 0.002 | −1.29 | 0.145 |
| Lzts1 | −1.97 | 0.001 | 1.43 | 0.017 |
| Eln | −1.95 | 0.004 | 1.14 | 0.472 |
| Slc5a2 | −1.94 | 0.018 | 2.09 | 0.010 |
| Tnp2 | −1.93 | 0.073 | 4.05 | 0.002 |
| Olfr1336 | −1.87 | 0.001 | 1.75 | 0.002 |
| Tdrd9 | −1.82 | 0.113 | 2.85 | 0.014 |
| Gm6602 | −1.81 | 0.194 | 2.83 | 0.038 |
| F830016B08Rik | −1.78 | 0.098 | 2.16 | 0.037 |
| Myo3b | −1.78 | 0.034 | 1.82 | 0.030 |
| Colec11 | −1.77 | 0.010 | 1.80 | 0.009 |
| Gm10428 | −1.75 | 0.010 | 1.94 | 0.005 |
| Vmn1r65 | −1.70 | 0.042 | 3.21 | 0.001 |
| Olfr67 | −1.69 | 0.003 | 1.37 | 0.034 |
| Bsnd | −1.69 | 0.107 | 2.05 | 0.038 |
| Slc10a5 | −1.69 | 0.038 | 1.65 | 0.045 |
| Defa26 | −1.68 | 0.076 | 2.06 | 0.022 |
| Serpinh1 | −1.68 | 0.124 | 2.01 | 0.049 |
| Gm5606 | −1.67 | 0.018 | 1.77 | 0.011 |
| Wfdc11 | −1.67 | 0.252 | 2.64 | 0.048 |
| Gimap7 | −1.65 | 0.091 | 1.92 | 0.036 |
| Nedd4l | −1.64 | 0.001 | 1.34 | 0.012 |
| Cacna1g | −1.63 | 0.094 | 1.81 | 0.049 |
| Prickle1 | −1.63 | 0.001 | 1.25 | 0.036 |
| 4931415C17Rik | −1.62 | 0.182 | 2.94 | 0.012 |
| D730005E14Rik | −1.61 | 0.156 | 2.30 | 0.025 |
| Ccr10 | −1.60 | 0.014 | 1.50 | 0.028 |
| Gm22 | −1.60 | 0.003 | 2.56 | 0.000 |
| Ngp | −1.60 | 0.075 | 1.83 | 0.030 |
| Ascl1 | −1.60 | 0.026 | 1.78 | 0.010 |
| Tgfb2 | −1.60 | 0.016 | 1.08 | 0.618 |
| Cyp2c29 | −1.59 | 0.009 | 1.42 | 0.030 |
| Gm5797 | −1.59 | 0.011 | 1.49 | 0.021 |
| Col5a3 | −1.59 | 0.035 | 1.05 | 0.779 |

TABLE 5-continued

| | miR-29b mimic | | antimiR-29 | |
|---|---|---|---|---|
| Gene | Fold change | p value | Fold change | p value |
| A730093L10Rik | −1.59 | 0.060 | 1.69 | 0.039 |
| Fkbp10 | −1.57 | 0.027 | 1.57 | 0.028 |
| Mfap2 | −1.56 | 0.032 | 1.83 | 0.008 |
| Gm5485 | −1.55 | 0.064 | 5.68 | 0.000 |
| Slamf9 | −1.54 | 0.204 | 2.08 | 0.048 |
| Mab21l3 | −1.54 | 0.005 | 1.53 | 0.006 |
| Fam57b | −1.53 | 0.008 | 1.50 | 0.010 |
| Pcolce | −1.53 | 0.091 | 1.62 | 0.060 |
| Gm6760 | −1.52 | 0.215 | 2.26 | 0.031 |
| Gng13 | −1.51 | 0.073 | 2.07 | 0.006 |
| 4933404M02Rik | −1.50 | 0.361 | 3.49 | 0.018 |
| C1qtnf6 | −1.50 | 0.032 | 1.50 | 0.031 |
| Tmem119 | −1.49 | 0.019 | 1.46 | 0.023 |
| Ubtd2 | −1.49 | 0.001 | 1.48 | 0.001 |
| Rasl11b | −1.48 | 0.045 | 1.77 | 0.009 |
| Nr5a2 | −1.47 | 0.011 | 1.36 | 0.031 |
| Gm3727 | −1.46 | 0.018 | 1.43 | 0.024 |
| Gprasp2 | −1.46 | 0.044 | 1.93 | 0.003 |
| Syt10 | −1.45 | 0.015 | 2.08 | 0.000 |
| Otog | −1.44 | 0.036 | 1.65 | 0.009 |
| Bdh2 | −1.43 | 0.011 | 1.81 | 0.001 |
| Sema3b | −1.42 | 0.045 | 1.56 | 0.017 |
| AI118078 | −1.42 | 0.032 | 1.69 | 0.005 |
| Npc1l1 | −1.41 | 0.032 | 1.40 | 0.036 |
| Dnmt3a | −1.41 | 0.015 | 1.30 | 0.046 |
| Cxcr6 | −1.40 | 0.024 | 1.99 | 0.000 |
| Sh3pxd2a | −1.37 | 0.044 | 1.42 | 0.029 |
| Scarf2 | −1.35 | 0.004 | 1.67 | 0.000 |
| LOC100862627 | −1.34 | 0.006 | 1.45 | 0.002 |
| Selm | −1.34 | 0.015 | 1.42 | 0.006 |
| Col11a1 | −1.34 | 0.509 | −1.02 | 0.958 |
| Slc12a5 | −1.34 | 0.007 | 1.29 | 0.013 |
| Pex11c | −1.33 | 0.000 | 1.24 | 0.002 |
| Gpr176 | −1.32 | 0.041 | 1.68 | 0.002 |
| Qprt | −1.32 | 0.037 | 1.29 | 0.050 |
| Phldb2 | −1.31 | 0.042 | 1.52 | 0.006 |
| Prl2c1 | −1.31 | 0.007 | 1.37 | 0.003 |
| Rab39 | −1.30 | 0.018 | 1.61 | 0.001 |
| Dact3 | −1.30 | 0.003 | 1.60 | 0.000 |
| Dlx3 | −1.26 | 0.010 | 1.19 | 0.037 |
| Sepw1 | −1.25 | 0.021 | 1.26 | 0.017 |
| Socs7 | −1.25 | 0.019 | 1.22 | 0.030 |
| Maged1 | −1.24 | 0.008 | 1.26 | 0.006 |
| Ckb | −1.22 | 0.035 | 1.24 | 0.026 |
| Mmp2 | −1.21 | 0.288 | 1.55 | 0.031 |
| Nfatc4 | −1.20 | 0.043 | 1.21 | 0.039 |
| Gm13623 | −1.20 | 0.032 | 1.51 | 0.000 |
| Trp53i13 | −1.19 | 0.025 | 1.32 | 0.002 |
| Lysmd4 | −1.17 | 0.015 | 1.23 | 0.004 |
| Polr2m | −1.17 | 0.000 | 1.12 | 0.002 |
| Pkd1 | −1.17 | 0.041 | 1.17 | 0.035 |
| Zdhhc1 | −1.16 | 0.034 | 1.25 | 0.005 |
| Nlgn2 | −1.15 | 0.043 | 1.22 | 0.009 |
| Gm9223 | −1.15 | 0.005 | 1.30 | 0.000 |
| Tox4 | −1.14 | 0.016 | 1.16 | 0.007 |
| Josd1 | −1.10 | 0.039 | 1.14 | 0.009 |
| Trip12 | −1.10 | 0.017 | 1.28 | 0.000 |
| Bet1l | −1.10 | 0.020 | 1.24 | 0.000 |
| Scaf1 | −1.09 | 0.039 | 1.16 | 0.003 |
| Dynlrb1 | −1.07 | 0.015 | 1.07 | 0.024 |
| Fam195b | −1.07 | 0.001 | 1.24 | 0.000 |
| Smarca5 | 1.05 | 0.013 | −1.05 | 0.023 |
| Rae1 | 1.07 | 0.016 | −1.17 | 0.000 |
| Nhp2l1 | 1.07 | 0.013 | −1.23 | 0.000 |
| Pin1-ps1 | 1.07 | 0.038 | −1.13 | 0.003 |
| Ppp1r7 | 1.08 | 0.011 | −1.16 | 0.000 |
| Lars | 1.08 | 0.012 | −1.11 | 0.002 |
| Wdsub1 | 1.09 | 0.031 | −1.13 | 0.006 |
| Fam120a | 1.09 | 0.043 | −1.10 | 0.032 |
| 3010027C24Rik | 1.10 | 0.032 | −1.15 | 0.005 |
| Eif4a3 | 1.10 | 0.021 | −1.14 | 0.004 |
| Vprbp | 1.10 | 0.042 | −1.38 | 0.000 |
| Naa20 | 1.10 | 0.008 | −1.07 | 0.037 |
| Smu1 | 1.11 | 0.006 | −1.17 | 0.001 |
| Tmed10 | 1.11 | 0.004 | −1.06 | 0.039 |
| Dus1l | 1.11 | 0.033 | −1.16 | 0.006 |

TABLE 5-continued

| | miR-29b mimic | | antimiR-29 | |
|---|---|---|---|---|
| Gene | Fold change | p value | Fold change | p value |
| Ecd | 1.11 | 0.026 | −1.24 | 0.001 |
| Naa10 | 1.11 | 0.015 | −1.10 | 0.026 |
| Ddx18 | 1.11 | 0.011 | −1.11 | 0.014 |
| Btbd9 | 1.11 | 0.002 | −1.06 | 0.037 |
| Ubap2l | 1.11 | 0.008 | −1.11 | 0.008 |
| Pnkp | 1.12 | 0.022 | −1.11 | 0.023 |
| Parl | 1.12 | 0.022 | −1.25 | 0.001 |
| Tle4 | 1.12 | 0.011 | −1.20 | 0.001 |
| Wbp11 | 1.12 | 0.027 | −1.12 | 0.026 |
| Nek4 | 1.12 | 0.027 | −1.26 | 0.001 |
| Poc5 | 1.13 | 0.039 | −1.12 | 0.046 |
| Uchl5 | 1.13 | 0.002 | −1.28 | 0.000 |
| Recql | 1.13 | 0.006 | −1.09 | 0.030 |
| Psmd3 | 1.13 | 0.011 | −1.10 | 0.028 |
| Asna1 | 1.13 | 0.033 | −1.31 | 0.000 |
| Polr1e | 1.13 | 0.048 | −1.20 | 0.009 |
| Csrp2bp | 1.13 | 0.023 | −1.18 | 0.006 |
| Parp1 | 1.13 | 0.049 | −1.14 | 0.043 |
| Abi1 | 1.13 | 0.003 | −1.48 | 0.000 |
| Tubgcp2 | 1.14 | 0.006 | −1.47 | 0.000 |
| Reps1 | 1.14 | 0.007 | −1.16 | 0.003 |
| Mon2 | 1.14 | 0.023 | −1.13 | 0.032 |
| Seh1l | 1.14 | 0.034 | −1.16 | 0.021 |
| Mri1 | 1.14 | 0.000 | −1.13 | 0.000 |
| Ddx20 | 1.14 | 0.002 | −2.18 | 0.000 |
| Nup133 | 1.14 | 0.001 | −1.09 | 0.006 |
| Ubr7 | 1.15 | 0.006 | −1.10 | 0.033 |
| Fam32a | 1.15 | 0.009 | −1.16 | 0.007 |
| Cct2 | 1.15 | 0.003 | −1.26 | 0.000 |
| Actl6a | 1.15 | 0.027 | −1.15 | 0.024 |
| Snrpb | 1.15 | 0.012 | −1.21 | 0.002 |
| Ino80 | 1.15 | 0.032 | −1.14 | 0.038 |
| 1500002O20Rik | 1.15 | 0.025 | −1.28 | 0.001 |
| Anxa7 | 1.15 | 0.008 | −1.18 | 0.003 |
| Wdr74 | 1.15 | 0.035 | −1.32 | 0.001 |
| Mrps27 | 1.16 | 0.015 | −1.22 | 0.003 |
| Trnau1ap | 1.16 | 0.007 | −1.18 | 0.004 |
| Usp39 | 1.16 | 0.031 | −1.19 | 0.015 |
| Mbd2 | 1.17 | 0.010 | −1.12 | 0.043 |
| Akap10 | 1.17 | 0.016 | −1.35 | 0.000 |
| Rps19bp1 | 1.17 | 0.031 | −1.23 | 0.008 |
| Faf1 | 1.17 | 0.026 | −1.25 | 0.004 |
| Wdr55 | 1.17 | 0.002 | −1.15 | 0.005 |
| Gorasp2 | 1.17 | 0.049 | −1.20 | 0.027 |
| Nfe2l2 | 1.17 | 0.011 | −1.23 | 0.002 |
| Nup54 | 1.17 | 0.048 | −1.70 | 0.000 |
| Med6 | 1.17 | 0.001 | −1.17 | 0.002 |
| Mapkap1 | 1.17 | 0.034 | −1.19 | 0.026 |
| Nsmce2 | 1.18 | 0.002 | −1.09 | 0.043 |
| Nsun2 | 1.18 | 0.011 | −1.17 | 0.016 |
| Map3k3 | 1.19 | 0.030 | −1.28 | 0.005 |
| Stat6 | 1.19 | 0.021 | −1.40 | 0.001 |
| Yrdc | 1.19 | 0.008 | −1.25 | 0.002 |
| Ap1m1 | 1.19 | 0.002 | −1.15 | 0.005 |
| Ccdc51 | 1.19 | 0.013 | −1.17 | 0.019 |
| Gins4 | 1.19 | 0.012 | −1.24 | 0.004 |
| Tmem165 | 1.19 | 0.027 | −1.21 | 0.018 |
| Txnl1 | 1.19 | 0.031 | −1.71 | 0.000 |
| Zfp608 | 1.19 | 0.000 | −1.30 | 0.000 |
| Mphosph10 | 1.19 | 0.019 | −1.29 | 0.003 |
| Spp1 | 1.20 | 0.014 | −1.16 | 0.029 |
| Wdr43 | 1.20 | 0.014 | −1.16 | 0.028 |
| Atpbd4 | 1.20 | 0.004 | −1.11 | 0.044 |
| Pafah1b2 | 1.20 | 0.050 | −1.20 | 0.049 |
| Exosc8 | 1.20 | 0.027 | −1.21 | 0.021 |
| Nop14 | 1.20 | 0.003 | −1.48 | 0.000 |
| Nop16 | 1.20 | 0.038 | −1.22 | 0.030 |
| Pdcd6ip | 1.20 | 0.011 | −1.90 | 0.000 |
| Cbl | 1.21 | 0.035 | −1.83 | 0.000 |
| Pcif1 | 1.21 | 0.020 | −1.24 | 0.011 |
| Rbm14 | 1.21 | 0.045 | −1.22 | 0.036 |
| Epb4.1l5 | 1.21 | 0.049 | −1.38 | 0.004 |
| Mtmr10 | 1.21 | 0.041 | −1.48 | 0.001 |
| Ttf2 | 1.21 | 0.030 | −1.42 | 0.001 |
| Cenpo | 1.22 | 0.009 | −1.31 | 0.002 |
| Rreb1 | 1.22 | 0.049 | −1.84 | 0.000 |

TABLE 5-continued

| | miR-29b mimic | | antimiR-29 | |
|---|---|---|---|---|
| Gene | Fold change | p value | Fold change | p value |
| Depdc5 | 1.22 | 0.002 | −1.39 | 0.000 |
| Umps | 1.23 | 0.012 | −1.16 | 0.046 |
| Zfp52 | 1.23 | 0.039 | −1.55 | 0.001 |
| BB070754 | 1.24 | 0.017 | −1.28 | 0.010 |
| Gnl3 | 1.24 | 0.036 | −1.34 | 0.010 |
| Rbbp5 | 1.25 | 0.003 | −1.34 | 0.001 |
| Fam178a | 1.26 | 0.048 | −1.35 | 0.015 |
| Etv5 | 1.27 | 0.035 | −1.55 | 0.002 |
| Gins1 | 1.27 | 0.034 | −1.32 | 0.019 |
| Lbr | 1.28 | 0.002 | −1.45 | 0.000 |
| Gm5039 | 1.29 | 0.030 | −1.57 | 0.002 |
| Pgam1 | 1.29 | 0.027 | −1.26 | 0.036 |
| Atg7 | 1.29 | 0.005 | −1.24 | 0.011 |
| 9030425P06Rik | 1.30 | 0.005 | −1.34 | 0.003 |
| Lyst | 1.30 | 0.028 | −2.43 | 0.000 |
| Rgs19 | 1.31 | 0.003 | −1.24 | 0.012 |
| Numb | 1.31 | 0.001 | −1.63 | 0.000 |
| Snx27 | 1.32 | 0.014 | −2.48 | 0.000 |
| Rnf130 | 1.32 | 0.021 | −1.31 | 0.026 |
| Pias3 | 1.33 | 0.014 | −1.90 | 0.000 |
| Pqlc3 | 1.33 | 0.009 | −1.30 | 0.013 |
| Chka | 1.33 | 0.005 | −1.44 | 0.001 |
| A430105D02Rik | 1.37 | 0.003 | −3.13 | 0.000 |
| Sdc4 | 1.38 | 0.004 | −2.05 | 0.000 |
| Rbm3 | 1.39 | 0.002 | −1.56 | 0.000 |
| 5830468K08Rik | 1.41 | 0.044 | −1.89 | 0.002 |
| Clcn5 | 1.41 | 0.026 | −1.49 | 0.014 |
| Fam65b | 1.41 | 0.049 | −1.50 | 0.026 |
| Tgfa | 1.46 | 0.004 | −1.34 | 0.015 |
| Fgd4 | 1.48 | 0.000 | −1.18 | 0.036 |
| 3930401B19Rik | 1.57 | 0.020 | −1.46 | 0.043 |
| Itga3 | 1.57 | 0.031 | −1.63 | 0.024 |
| 2410137M14Rik | 1.63 | 0.040 | −1.64 | 0.039 |
| Egr4 | 2.02 | 0.024 | −1.86 | 0.040 |
| Olfr663 | 2.06 | 0.022 | −2.08 | 0.020 |

Figure 10B:
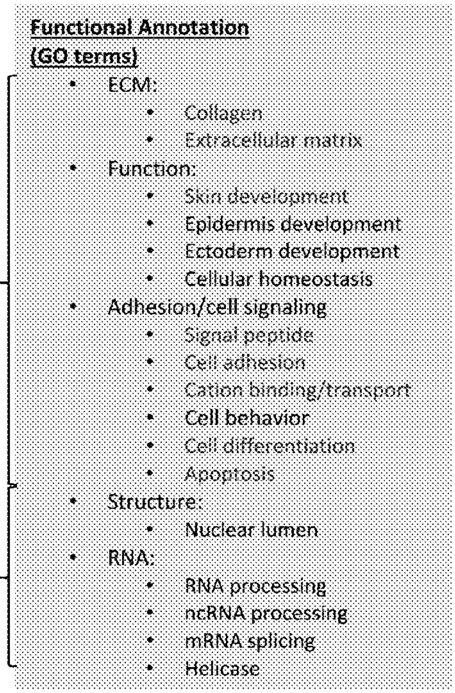
FIG. 10B. miR29b mimic and antimiR effects on gene expression in mouse skin. DAVID analysis (NCBI) of functional terms that are enriched in the two groups shown in FIG. 10A are presented Gene Ontology (GO) terms of Extracellular Matrix, (Skin) Function, Adhesion/Cell Signaling and Cell Differentiation/Apoptosis are the top negatively regulated pathways following miR-29b mimic treatment and Cellular (Nuclear) Structure and RNA Processing are the top positively regulated pathways following miR-29b mimic treatment. The microarray analysis of skin and acute skin wounds in C57BL/6 mice shows reciprocal regulation of 228 genes by intradermal treatment with a miR-29b mimic comprising SEQ ID NO: 2 and SEQ ID NO: 1, and antimiR-29 (SEQ ID NO: 36).

DAVID analysis (NCBI) of functional terms that are enriched in the two groups are presented in FIG. 10B. Not surprisingly, the Gene Ontology (GO) terms of Extracellular Matrix, (Skin) Function, Adhesion/Cell Signaling and Cell Differentiation/Apoptosis are the top negatively regulated pathways following miR-29b mimic treatment Cellular (Nuclear) Structure and RNA Processing are the top positively regulated pathways following miR-29b mimic treatment.

Figure 11A:
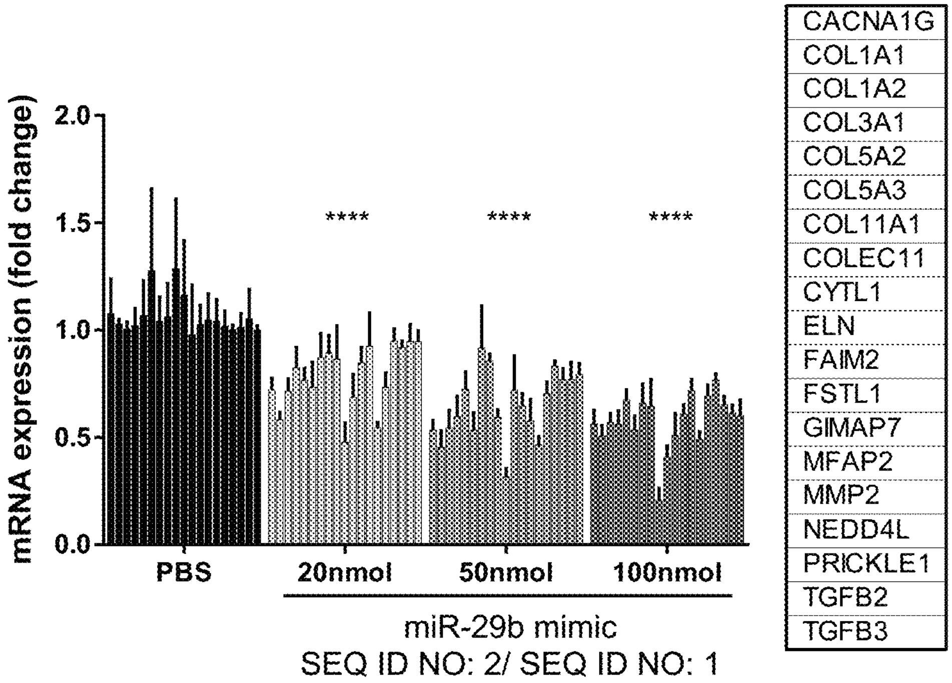
FIG. 11A. Quantitative real-time (RT)-PCR analysis of mouse incisional wounds treated with intradermal miR-29b mimic (SEQ ID NO: 2/SEQ ID NO: 1) or PBS control. Data are presented as a grouped bar graph where the first bar in each treatment group represents the expression level of the first gene in the list on the right, and so on. RT-PCR confirmed that collagens, other extracellular matrix genes and other direct and indirect target genes previously shown to be repressed by miR-29b mimic treatment (FIG. 10*a*, upper half of the heatmap) show a dose-dependent reduction in expression with miR-29b mimic treatment in acute skin wounds. **** p<0.0001 versus PBS treated incisions, using a 2-way ANOVA with treatment and gene as the two factors assessed.
Figure 11B:
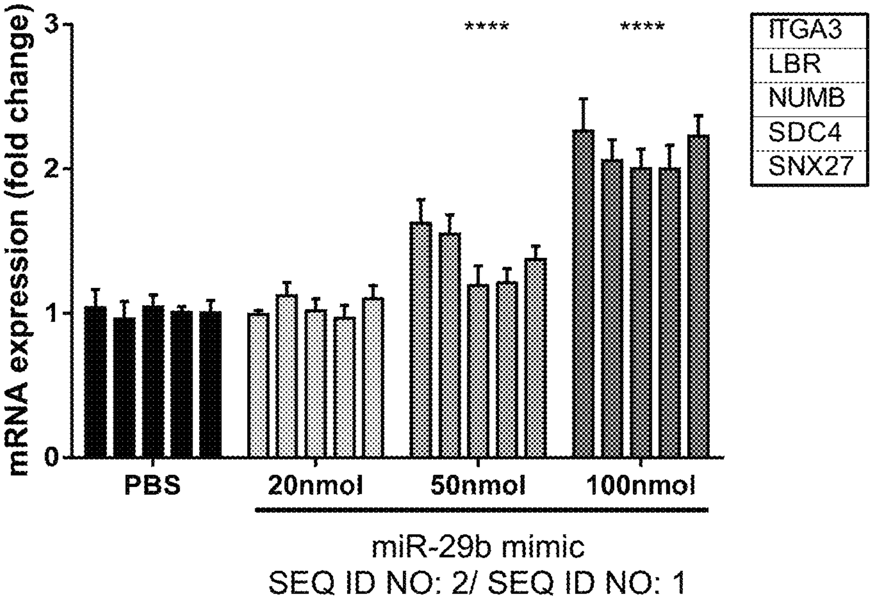
FIG. 11B. Genes previously identified as being de-repressed with miR-29b mimic treatment (FIG. 10A, lower half of the heatmap) show a dose-dependent increase in expression with miR-29b mimic treatment by quantitative RT-PCR. * p<0.001 and ** p<0.0001 versus PBS treated incisions, using a 2-way ANOVA with treatment and gene as the two factors assessed. The miR-29b mimic significantly affects the expression of miR-29 target genes in acute skin wounds.

To further confirm the effect of miR-29b mimic treatment in the skin, mice with acute incisional wounds were treated with intradermal injection of PBS, 20, 50, or 100 nmol of miR-29b mimic (comprising SEQ ID NO: 2 as the first strand and SEQ ID NO: 1 as the second strand). Quantitative reverse-transcriptase PCR analysis was performed on 24 genes identified as being direct or indirect targets of miR-29 modulation in the skin (19 repressed by miR-29b mimic and upregulated by antimiR-29, 5 upregulated by miR-29b mimic and repressed by antimiR-29). Extracellular matrix genes (collagens, ELN, etc.) and others involved in the fibrotic process (e.g. MMP2, TGFB2) were shown to be repressed by miR-29b mimic treatment in the skin (FIG. 11A), whereas selected cell surface receptors (ITGA3, LBR, NUMB, SDC4) and factors associated with receptor endocytosis (SNX27) were shown to be increased with miR-29b mimic treatment in the skin (FIG. 11B). These studies indicate that the miR-29b mimic is active when treated locally in the skin, and suggests that in addition to its effect on organ fibrosis, miR-29 mimicry could be an effective therapy for cutaneous fibrosis of various etiologies. These studies also identify the above-mentioned genes as translational biomarkers whose expression correlates with the activity of a miR-29b mimic in the skin. These translational biomarkers can be utilized in a clinical trial, testing the safety and efficacy of miR-29b mimics in normal healthy volunteers and patients with cutaneous scleroderma.

Example 5

Activity of MiR-29 Mimics and Effects of Nucleotide Modifications

Figure 12:
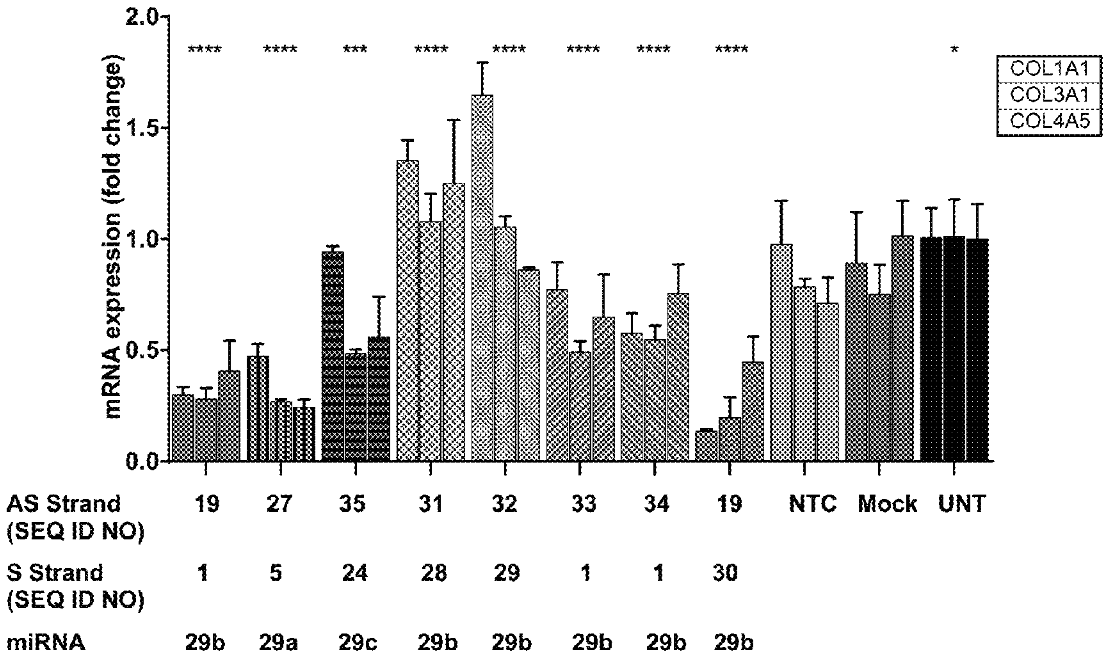
FIG. 12. Activity of miR-29 mimics and effects of nucleotide modifications. Transfection experiments in IMR-90 human lung fibroblasts show that different miR-29 mimics have different levels of activity as measured by repression of collagen gene expression. * $p<0.05$, * $p<0.001$ and ** $p<0.0001$ versus mock transfection, using a 2-way ANOVA with treatment and gene as the two factors assessed.

To determine the efficacy of miR-29a, b, and c mimics in regulating the expression of target genes, different miR-29a, b and c mimics were transfected into IMR-90 human lung fibroblasts at a concentration of 10 nM, and collagen expression was measured by quantitative RT-PCR. These studies demonstrate that a miR-29a mimic comprising SEQ ID NO: 27 as the first strand and SEQ ID NO: 5 as the second strand and a miR-29b mimic comprising SEQ ID NO: 19 as the first strand and SEQ ID NO: 1 as the second strand are the most effective at repressing expression of multiple collagen genes, whereas a miR-29c mimic comprising SEQ ID NO: 35 as the first strand and SEQ ID NO: 24 as the second strand is less effective (FIG. 12). These effects may be cell-type or target gene specific, but indicate that there are indeed differences in the ability of the three mimics to repress extracellular matrix gene expression.

In the same experiment, the effect of nucleotide modifications on the efficacy of miR-29b mimics was also tested. These studies indicate that the miR-29b mimic containing SEQ ID NO: 19 as the first strand and SEQ ID NO: 1 as the second strand performs similarly to a miR-29b mimic comprising SEQ ID NO: 19 as the first strand and SEQ ID NO: 30 as the second strand which has the same first and second sequence and pattern, but a different chemical linker between the sense (passenger) strand and cholesterol. A checkerboard pattern of 2' O-Methyl modifications makes miR-29 mimics (a mimic comprising SEQ ID NO: 31 as the first strand and SEQ ID NO: 28 as the second strand and a mimic comprising SEQ ID NO: 32 as the first strand and SEQ ID NO: 29 as the second strand) completely ineffective. Modifications of all C and U residues on the antisense (first/guide) strand (a mimic comprising SEQ ID NO: 33 as the first strand and SEQ ID NO: 1 as the second strand) partially reduces the mimic activity. Similarly, removal of the 3' overhang on the antisense strand (a mimic comprising SEQ ID NO: 24 as the first strand and SEQ ID NO: 1 as the second strand) partially reduces the mimic activity. See FIG. 12.

These studies have allowed the stratification of miR-29 mimic compounds on the basis of in vitro activity in a specific cell line (IMR-90) and using particular target genes (COL1A1, COL3A1, COL4A5) as the readout for efficacy, independent on compound uptake, and can be used as the basis for selecting compounds to test via passive delivery in vitro or to test in vivo.

Example 6

In Vivo Activity of MiR-29b Mimics with Linker Modifications

Mice with incisional wounds were treated with 20 nmol of various miR-29b mimics that differ only in the linkage between the cholesterol moiety and the second/sense strand. The mimetic compound that contained a six carbon linker between cholesterol and the sense strand (the mimic comprising SEQ ID NO: 19 as the first strand and SEQ ID NO: 1 as the second strand) and the compound that contained the same six carbon linker between cholesterol and the sense strand but connected through a cleavable moiety (dT.dT) (SEQ ID NO: 19/SEQ ID NO: 15) showed similar activity in repressing target genes (FIG. 13). N/S in FIG. 13 represents no significant difference was observed in the activities of the miR-29b mimic comprising SEQ ID NO: 19 as the first strand and SEQ ID NO: 1 as the second strand and the mimic comprising SEQ ID NO: 19 as the first strand and SEQ ID NO: 15 as the second strand, miR-29b mimics containing a nine carbon linker (SEQ ID NO: 19/SEQ ID NO: 17) and a linker at the 5' end (SEQ ID NO: 19/SEQ ID NO: 16) were not effective in repressing target genes (FIG. 13).

Example 7

Effect of 5' Phosphorylation on the Activity of MiR-29b Mimics

RAB-9 skin fibroblast cells (ATCC CRL-1414) were transfected with varying concentrations of miR-29b mimics with (the mimic containing SEQ ID NO: 2 as the first strand and SEQ ID NO: 1 as the second strand) and without (the mimic containing SEQ ID NO: 19 as the first strand and SEQ ID NO: 1 as the second strand) 5' phosphorylation on the antisense strand. No significant differences in target gene repression as measured by Col1a1, Col1a2 or Col3a1 expression was observed in the activity of the two mimics (represented as N/S in FIG. 14). Both miR-29b mimics significantly ($p<0.0001$) repressed the expression of target genes compared to vehicle, mock transfection or control mimic treatment. See FIG. 14.

REFERENCES

Bouchie A (2013) First microRNA mimic enters clinic. *Nature biotechnology* 31: 577

Cashing L, Kuang P P, Qian J, Shao F, Wu J, Little F, Thannickal V J, Cardoso W V, Lu J (2011) miR-29 is a major regulator of genes associated with pulmonary fibrosis. *American journal of respiratory cell and molecular biology* 45: 287-294

Friedman S L, Sheppard D, Duffield J S, Violette S (2013) Therapy for fibrotic diseases: nearing the starting line. *Sci Transl Med* 5: 167sr161

He Y, Huang C, Lin X, Li J (2013) MicroRNA-29 family, a crucial therapeutic target for fibrosis diseases. *Biochimie* 95: 1355-1359

Janssen H L, Reesink H W, Lawitz E J, Zeuzem S, Rodriguez-Torres M, Patel K, van der Meer A J, Patick A K, Chen A, Zhou Y, Persson R, King B D, Kauppinen S, Levin A A, Hodges M R (2013) Treatment of HCV infection by targeting microRNA. *The New England journal of medicine* 368: 1685-1694

Kasinski A L, Slack F J (2012) miRNA-34 prevents cancer initiation and progression in a therapeutically resistant K-ras and p53-induced mouse model of lung adenocarcinoma. *Cancer Res* 72: 5576-5587

Kota J, Chivukula R R, O'Donnell K A, Wentzel E A, Montgomery C L, Hwang H W, Chang T C, Vivekanandan P, Torbenson M, Clark K R, Mendell J R, Mendell J T (2009) Therapeutic microRNA delivery suppresses tumorigenesis in a murine liver cancer model. *Cell* 137: 1005-1017

Maurer B, Stanczyk J, Jungel A, Akhmetshina A, Trenkmann M, Brock M, Kowal-Bielecka O, Gay R E, Michel B A, Distler J H, Gay S, Distler O (2010) MicroRNA-29, a key regulator of collagen expression in systemic sclerosis. *Arthritis and rheumatism* 62: 1733-1743

Miyazaki Y, Adachi H, Katsuno M, Minamiyama M, Jiang Y M, Huang Z, Doi H, Matsumoto S, Kondo N, Iida M, Tohnai G, Tanaka F, Muramatsu S I, Sobue G (2012) Viral delivery of miR-196a ameliorates the SBMA phenotype via the silencing of CELF2. *Nature medicine*

Pandit K V, Corcoran D, Yousef H, Yarlagadda M, Tzouvelekis A, Gibson K F, Konishi K, Yousem S A, Singh M, Handley D, Richards T, Selman M, Walkins S C, Pardo A, Ben-Yehudah A, Bouros D, Eickelberg O, Ray P, Benos P V, Kaminski N (2010) Inhibition and role of let-7d in idiopathic pulmonary fibrosis. *Am J Respir Crit Care Med* 182: 220-229

Pandit K V, Milosevic J, Kaminski N (2011) MicroRNAs in idiopathic pulmonary fibrosis. *Transl Res* 157: 191-199

Peacock H, Kannan A, Beal P A, Burrows C J (2011) Chemical modification of siRNA bases to probe and enhance RNA interference. *The Journal of organic chemistry* 76: 7295-7300

Qin W, Chung A C, Huang X R, Meng X M, Hui D S , Yu C M, Sung J J, Lan H Y (2011) TGF-beta/Smad3 signaling promotes renal fibrosis by inhibiting miR-29. *Journal of the American Society of Nephrology: JASN* 22: 1462-1474

Roderburg C, Urban G W, Bettermann K, Vucur M, Zimmermann H, Schmidt S, Janssen J, Koppe C, Knolle P, Castoldi M, Tacke F, Trautwein C, Luedde T (2011) Micro-RNA profiling reveals a role for miR-29 in human and murine liver fibrosis. *Hepatology* 53: 209-218

Sekiya Y, Ogawa T, Yoshizato K, Ikeda K, Kawada N (2011) Suppression of hepatic stellate cell activation by microRNA-29b. *Biochemical and biophysical research communications* 412: 74-79 van Rooij E, Olson E N (2012) MicroRNA therapeutics for cardiovascular disease: opportunities and obstacles. *Nature reviews Drug discovery* 11: 860-872 van Rooij E, Purcell A L, Levin A A (2012) Developing microRNA therapeutics. *Circ Res* 110: 496-507 van Rooij E, Sutherland L B, Thatcher J E, DiMaio J M, Naseem R H, Marshall W S, Hill J A, Olson E N (2008) Dysregulation of microRNAs after myocardial infarction reveals a role of miR-29 in cardiac fibrosis. *Proc Natl Acad Sci USA* 105: 13027-13032

Wang B, Komers R, Carew R, Winbanks C E, Xu B, Herman-Edelstein M, Koh P, Thomas M, Jandeleit-Dahm K, Gregorevic P, Cooper M E, Kantharidis P (2012) Suppression of microRNA-29 expression by TGF-beta1 promotes collagen expression and renal fibrosis. *Journal of the American Society of Nephrology : JASN* 23: 252-265

Xiao J, Meng X M, Huang X R, Chung A C, Feng Y L, Hui D S, Yu C M, Sung J J, Lan H Y (2012) miR-29 inhibits bleomycin-induced pulmonary fibrosis in mice. *Molecular therapy: the journal of the American Society of Gene Therapy* 20: 1251-1260

Zhang Y, Wu L, Wang Y, Zhang M, Li L, Zhu D, Li X, Gu H, Zhang C Y, Zen K (2012) Protective role of estrogen-induced miRNA-29 expression in carbon tetrachloride-induced mouse liver injury. *The Journal of biological chemistry* 287: 14851-14862

The invention claimed is:

1. A miR-29 mimetic compound comprising:

a first strand of about 25 to about 26 ribonucleotides that comprises the sequence of SEQ ID NO: 19; and a second strand of about 23 ribonucleotides that comprises the sequence of SEQ ID NO: 1, wherein the first strand has a 3' nucleotide overhang relative to the second strand, and wherein the second strain contains mismatches from the 3' end at positions 4, 13, and 16 relative to the first strand.

2. A pharmaceutical composition comprising an effective amount of the miR-29 mimetic compound of claim 1, or a pharmaceutically-acceptable salt thereof, and a pharmaceutically-acceptable carrier or diluent.

3. The pharmaceutical composition of claim 2, wherein the composition is an inhalation composition.

4. A method of regulating an extracellular matrix gene in a cell comprising contacting the cell with the miR-29 mimetic compound of claim 1.

5. The method of claim 4, wherein the cell is a mammalian cell.

6. The method of claim 5, wherein the cell is a fibroblast or epithelial cell.

7. The method of claim 4, wherein the cell is in vivo or ex vivo.

8. A method of treating or preventing tissue fibrosis in a subject in need thereof comprising administering to the subject the miR-29 mimetic compound of claim 1.

9. The method of claim 8, wherein the tissue fibrosis is cardiac fibrosis, pulmonary fibrosis, renal fibrosis, hepatic fibrosis, scleroderma, ocular fibrosis, cutaneous fibrosis.

10. The method of claim 9, wherein the cutaneous fibrosis is selected from the group consisting of hypertrophic scarring, keloids, fibrosis of hands, joints or tendons and Peyronie's disease.

11. The method of claim 8, wherein the administration is via inhalation.

12. The method of claim 8, wherein the miR-29 mimetic compound or the pharmaceutical composition is administered via a metered dose inhaler, dry powder inhaler, nebulizer, heat vaporizer, soft mist inhaler, thermal aerosol inhaler, or an electrohydrodynamic-based solution misting inhaler.

* * * * *